United States Patent
Kim et al.

(10) Patent No.: US 9,481,684 B2
(45) Date of Patent: Nov. 1, 2016

(54) GONADOTROPIN RELEASING HORMONE RECEPTOR ANTAGONISTS, METHOD FOR THE PREPARATION THEREOF AND PHARMACEUTICAL COMPOSITION COMPRISING THE SAME

(71) Applicant: SK CHEMICALS CO., LTD., Seongnam-si, Gyeonggi-do (KR)

(72) Inventors: Seon-Mi Kim, Suwon-si (KR); Jae-Sun Kim, Suwon-si (KR); Minhee Lee, Yongin-si (KR); So-young Lee, Suwon-si (KR); Bong-yong Lee, Seoul (KR); Young-Ah Shin, Yongin-si (KR); Euisun Park, Yongin-si (KR); Jung A Lee, Uiwang-si (KR); Min-Young Han, Seongnam-si (KR); Jaeseung Ahn, Seoul (KR); Taekyung Yoo, Uiwang-si (KR); Hun-Taek Kim, Seoul (KR)

(73) Assignee: SK CHEMICALS CO., LTD., Seongnam-si (KR)

( * ) Notice: Subject to any disclaimer, the term of this patent is extended or adjusted under 35 U.S.C. 154(b) by 0 days.

(21) Appl. No.: 14/381,371

(22) PCT Filed: Feb. 28, 2013

(86) PCT No.: PCT/KR2013/001660
§ 371 (c)(1),
(2) Date: Aug. 27, 2014

(87) PCT Pub. No.: WO2013/129879
PCT Pub. Date: Sep. 6, 2013

(65) Prior Publication Data
US 2015/0166558 A1    Jun. 18, 2015

(30) Foreign Application Priority Data

Feb. 28, 2012  (KR) .................. 10-2012-0020479

(51) Int. Cl.
| | | |
|---|---|---|
| *C07D 491/20* | (2006.01) | |
| *C07D 471/10* | (2006.01) | |
| *A61P 15/18* | (2006.01) | |
| *A61P 5/04* | (2006.01) | |
| *A61P 5/24* | (2006.01) | |
| *C07D 491/10* | (2006.01) | |
| *A61P 35/00* | (2006.01) | |

(52) U.S. Cl.
CPC ............ *C07D 491/20* (2013.01); *C07D 471/10* (2013.01); *C07D 491/10* (2013.01)

(58) Field of Classification Search
CPC . C07D 471/10; C07D 491/10; C07D 491/20
See application file for complete search history.

(56) References Cited

U.S. PATENT DOCUMENTS

| 5,633,248 A | 5/1997 | Kato et al. |
| 6,156,772 A | 12/2000 | Goulet et al. |
| 2005/0250846 A1 | 11/2005 | Anderson et al. |

OTHER PUBLICATIONS

Banker, G.S. et al, "Modern Pharmaceutics, 3ed.", Marcel Dekker, New York, 1996, p. 596.*
Wolff, Manfred E. "Burger's Medicinal Chemistry, 5ed, Part I", John Wiley & Sons, 1995, pp. 975-977.*
R.P. Millar et al., "Progress towards the development of non-peptide orally-active gonadotropin-releasing hormone (GnRH) antagonists: therapeutic implications", Br. Med. Bull., 2000, vol. 56, pp. 761-772.
The International Searching Authority, Written Opinion for PCT/KR2013/001660 dated Jun. 27, 2013.
The International Searching Authority, International Search Report for PCT/KR2013/001660 dated Jun. 27, 2013.
Pontillo et al.: "Efficient synthesis of bicyclic oxazolino- and thiazolino[3,2-c] pyrimidine-5,7-diones and its application to the synthesis of GnRH antagonists", Bioorg. Med. Chem. Lett., vol. 15, No. 5, Mar. 1, 2005, pp. 1407-1411.
Sarma et al.: "Peptidomimetic GnRH receptor antagonists for the treatment of reproductive and proliferative diseases", Expert Opin. Ther. Patents, vol. 16, No. 6, Jun. 1, 2006, pp. 733-751.
European Patent Office; Communication dated Sep. 22, 2015 in counterpart application No. 13754960.6.

* cited by examiner

*Primary Examiner* — Susanna Moore
(74) *Attorney, Agent, or Firm* — Sughrue Mion, PLLC

(57) ABSTRACT

Disclosed are a gonadotropin releasing hormone receptor antagonist and a pharmaceutical composition including the same, which can be useful in preventing or treating a sex hormone-related disease such as endometriosis, amenorrhea, irregular menstruation, uterine myoma, uterine fibroids, polycystic ovarian disease, lupus erythematous, hypertrichosis, precocious puberty, short stature, acne, alopecia, gonadal steroid-dependent neoplasms, gonadotropin-producing pituitary adenoma, sleep apnea, irritable bowel syndrome, premenstrual syndrome, benign prostatic hyperplasia, contraception, and infertility, as well as Alzheimer disease.

9 Claims, No Drawings

GONADOTROPIN RELEASING HORMONE RECEPTOR ANTAGONISTS, METHOD FOR THE PREPARATION THEREOF AND PHARMACEUTICAL COMPOSITION COMPRISING THE SAME

CROSS REFERENCE TO RELATED APPLICATIONS

This application is a National Stage of International Application No. PCT/KR2013/001660 filed Feb. 28, 2013, claiming priority based on Korean Patent Application No. 10-2012-0020479, filed Feb. 28, 2012, the contents of all of which are incorporated herein by reference in their entirety.

FIELD OF THE INVENTION

The present invention relates to a gonadotropin releasing hormone (GnRH) receptor antagonist, a method for the preparation thereof and a pharmaceutical composition comprising the same.

BACKGROUND OF THE INVENTION

Gonadotropin releasing hormone (known as a luteinizing hormone releasing hormone) is a decapeptide which is secreted from the hypothalamus and affects receptors located in the anterior pituitary gland to stimulate biosynthesis and secretion of luteinizing hormones (LH) and follicle-stimulating hormones (FSH). Luteinizing hormone modulates the synthesis of steroids from genital glands in both males and females. It participates in the development of spermatogenesis in males and follicle in females. Thus, much attention has been given to GnRH receptor agonists or antagonists as a therapeutic agent for hormone-related diseases, especially, prostate cancer, breast cancer, endometriosis, uterine myoma, precocious puberty and the like, as well as infertility.

There are two different modes of action for the therapeutic agents that are currently being used. In one mode of action, the therapeutic agent acts as a GnRH antagonist that requires continuous administration which depletes gonadotropins and downregulates the receptors, thereby causing suppression of steroidal hormones approximately after 2 to 3 weeks following the initiation of continuous administration. However, it is inevitable to undergo superagonism in the beginning, thus there is an inconvenience that patients must go through initial side effects in this mode.

In the other mode of action, it directly acts as a GnRH antagonist so that it can suppress gonadotropins from the onset. This mechanism may reduce the level of gonadotropin directly without causing initial side effects. However, it was found in clinical studies that GnRH antagonists showed relatively low bioavailability and adverse side effects caused by histamine release. Although, there have been reported peptidic antagonist having low histamine release properties, they still must be delivered via parental administration routes (e.g., intravenous, subcutaneous and intramuscular injection) due to limited bioavailability.

Accordingly, there has been suggested a nonpeptide antagonist to overcome the limitations associated with peptidic GnRH antagonists (Sarma, P K S, *Expert Opin. Ther. Patents* 16(6): 733-751, 2006). However, there still remains a need for a low-molecular GnRH receptor antagonist having good bioavailability despite intensive research studies in this field.

SUMMARY OF THE INVENTION

Accordingly, it is an object of the present invention to provide a compound useful as a GnRH receptor antagonist.

It is another object of the present invention to provide a pharmaceutical composition comprising the same.

It is further object of the present invention to provide a method for preventing or treating a sex hormone-related disease using the compound.

It is a still further object of the present invention to provide a use of the compound for the manufacture of a medicament for preventing or treating a sex hormone-related disease.

MEANS FOR SOLVING THE PROBLEM

In accordance with one aspect of the present invention, there is provided a compound of formula (I), or a stereoisomer, a prodrug or a pharmaceutically acceptable salt thereof:

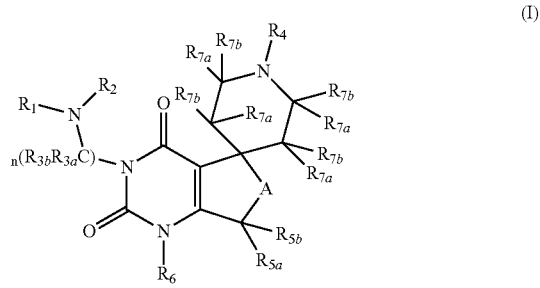

(I)

wherein,

A is $CR_{8a}R_{8b}$, O, S or $NR_9$;

$R_1$ and $R_2$, which may be the same or different, being each independently hydrogen, $(C_1-C_{10})$alkyl, substituted $(C_1-C_{10})$alkyl, $(C_3-C_{10})$cycloalkyl, substituted $(C_3-C_{10})$cycloalkyl, $(C_6-C_{12})$aryl, substituted $(C_6-C_{10})$aryl, $(C_6-C_{12})$aryl$(C_1-C_{10})$alkyl, substituted $(C_6-C_{12})$aryl$(C_1-C_{10})$alkyl, $(C_1-C_{20})$heteroaryl, substituted $(C_1-C_{20})$heteroaryl, $(C_1-C_{20})$heteroaryl$(C_1-C_{10})$alkyl, substituted $(C_1-C_{20})$heteroaryl$(C_1-C_{10})$alkyl, $(C_1-C_{20})$heterocycle, substituted $(C_1-C_{20})$heterocycle, $(C_1-C_{20})$heterocyclyl$(C_1-C_{10})$alkyl, substituted $(C_1-C_{20})$heterocyclyl$(C_1-C_{10})$alkyl, or $-(CR_{1a}R_{1b})_s-R_{12}$;

$R_{3a}$ and $R_{3b}$, which may be the same or different, being each independently hydrogen, $(C_1-C_{10})$alkyl, substituted $(C_1-C_{10})$alkyl, $(C_3-C_{10})$cycloalkyl, substituted $(C_3-C_{10})$cycloalkyl, $(C_1-C_{10})$alkoxy, $(C_1-C_{10})$alkylthio, $(C_1-C_{10})$alkylamino, $(C_6-C_{12})$aryl, substituted $(C_6-C_{12})$aryl, $(C_6-C_{12})$aryl$(C_1-C_{10})$alkyl, substituted $(C_6-C_{12})$aryl$(C_1-C_{10})$alkyl, $(C_1-C_{20})$heteroaryl, substituted $(C_1-C_{20})$heteroaryl, $(C_1-C_{20})$heteroaryl$(C_1-C_{10})$alkyl, substituted $(C_1-C_{20})$heteroaryl$(C_1-C_{10})$alkyl, $(C_1-C_{20})$heterocycle, substituted $(C_1-C_{20})$heterocycle, $(C_1-C_{20})$heterocyclyl$(C_1-C_{10})$alkyl, substituted $(C_1-C_{20})$heterocyclyl$(C_1-C_{10})$alkyl, $-COOR_{13}$ or $-CONR_{13}R_{14}$;

$R_{3a}$ and $R_{3b}$, together with the carbon atom attached thereto form a homocyclic ring, a substituted homocyclic ring, a heterocyclic ring, or a substituted heterocyclic ring; or $R_{3a}$ and a carbon bonded thereto, together with $R_1$ and a nitrogen atom bonded thereto, form a heterocyclic ring or a substituted heterocyclic ring;

$R_4$ is $-(CR_{9a}R_{9b})_r-Z-Y$;

n is an integer of 2, 3 or 4;

s is an integer of 1, 2, 3 or 4;

r is an integer of 0, 1 or 2;

Z represents a direct bond, or —O—, —S—, —$NR_{11}$—, —SO—, —$SO_2$—, —$OSO_2$—, —$SO_2$—, —$SO_2NR_{11}$—, —$NR_{11}SO_2$—, —CO—, —COO—, —OCO—, —$CONR_{11}$—, —$NR_{11}CO$—, —$NR_{11}CONR_{11a}$—, —$OCONR_{11}$— or —$NR_{11}COO$—;

Y is hydrogen, halogen, $(C_1\text{-}C_{10})$alkyl, substituted $(C_1\text{-}C_{10})$alkyl, $(C_3\text{-}C_{10})$cycloalkyl, substituted $(C_3\text{-}C_{10})$cycloalkyl, $(C_6\text{-}C_{12})$aryl, substituted $(C_6\text{-}C_{12})$aryl, $(C_6\text{-}C_{12})$aryl$(C_1\text{-}C_{10})$alkyl, substituted $(C_6\text{-}C_{12})$aryl$(C_1\text{-}C_{10})$alkyl, $(C_1\text{-}C_{20})$heteroaryl, substituted $(C_1\text{-}C_{20})$heteroaryl, $(C_1\text{-}C_{20})$heteroaryl$(C_1\text{-}C_{10})$alkyl or substituted $(C_1\text{-}C_{20})$heteroaryl$(C_1\text{-}C_{10})$alkyl;

$R_6$ is hydrogen, $(C_1\text{-}C_{10})$alkyl, substituted $(C_1\text{-}C_{10})$alkyl, $(C_3\text{-}C_{10})$cycloalkyl, substituted $(C_3\text{-}C_{10})$cycloalkyl, $(C_6\text{-}C_{12})$aryl, substituted $(C_6\text{-}C_{12})$aryl, $(C_6\text{-}C_{12})$aryl$(C_1\text{-}C_{10})$alkyl, substituted $(C_6\text{-}C_{12})$aryl$(C_1\text{-}C_{10})$alkyl, $(C_1\text{-}C_{20})$heteroaryl, substituted $(C_1\text{-}C_{20})$heteroaryl, $(C_1\text{-}C_{20})$heteroaryl$(C_1\text{-}C_{10})$alkyl or substituted $(C_1\text{-}C_{20})$heteroaryl$(C_1\text{-}C_{10})$alkyl;

$R_9$ is hydrogen, $(C_1\text{-}C_{10})$alkyl or $(C_1\text{-}C_{10})$acyl;

$R_{12}$ is —$CO_2R_{13}$, —COOH or an acid isostere;

$R_{1a}$ and $R_{1b}$, which may be the same or different, being each independently hydrogen, $(C_1\text{-}C_{10})$acyl, hydroxyl, halogen, cyano, $(C_1\text{-}C_{10})$alkyl, substituted $(C_1\text{-}C_{10})$alkyl, $(C_3\text{-}C_{10})$cycloalkyl, substituted $(C_3\text{-}C_{10})$cycloalkyl, $(C_1\text{-}C_{10})$alkoxy, $(C_1\text{-}C_{10})$alkylthio, $(C_1\text{-}C_{10})$alkylamino, —$COOR_{13}$— or $CONR_{13}R_{14}$—; or $R_{1a}$ and $R_{1b}$, together with the atom(s) to which they are attached independently from a homocyclic ring, a substituted homocyclic ring, a heterocyclic ring or a substituted heterocyclic ring;

$R_{5a}$, $R_{5b}$, $R_{7a}$, $R_{7b}$, $R_{8a}$ and $R_{8b}$, which may be the same or different, being each independently hydrogen, $(C_1\text{-}C_{10})$acyl, hydroxyl, amino, halogen, cyano, $(C_1\text{-}C_{10})$alkyl, substituted $(C_1\text{-}C_{10})$alkyl, $(C_3\text{-}C_{10})$cycloalkyl, substituted $(C_3\text{-}C_{10})$cycloalkyl, $(C_1\text{-}C_{10})$aryl, substitute $(C_1\text{-}C_{10})$aryl, $(C_1\text{-}C_{10})$alkoxy, $(C_1\text{-}C_{10})$alkylthio, $(C_1\text{-}C_{10})$alkylamino, —$COOR_{13}$, or —$CONR_{14}R_{15}$; and $R_{9a}$, $R_{9b}$, $R_{11}$, $R_{11b}$, $R_{13}$, $R_{14}$ and $R_{15}$, which may be the same of different, being each independently hydrogen, $(C_1\text{-}C_{10})$alkyl, $(C_6\text{-}C_{12})$aryl or $(C_6\text{-}C_{12})$aryl$(C_1\text{-}C_{10})$alkyl;

wherein, the heterocyclic ring, the hetercycle, the heterocyclylalkyl, heteroaryl and heteroarylalkyl contain at least one heteroatoms selected from the group consisting of N, O and S; and "substituted" being intended to mean replacement with at least one substituent selected from the group consisting of halogen, acetylene, vinyl, hydroxy, cyano, nitro, amino, $(C_1\text{-}C_{10})$alkylamino, di$(C_1\text{-}C_{10})$alkylamino, $(C_1\text{-}C_{10})$alkyl, $(C_3\text{-}C_{10})$cycloalkyl, $(C_1\text{-}C_{10})$alkoxy, $(C_1\text{-}C_{10})$alkylthio, halo$(C_1\text{-}C_{10})$alkyl, $(C_6\text{-}C_{12})$aryl, $(C_6\text{-}C_{12})$aryl$(C_1\text{-}C_{10})$alkyl, $(C_1\text{-}C_{20})$heteroaryl, $(C_1\text{-}C_{20})$heteroaryl$(C_1\text{-}C_{10})$alkyl, $(C_1\text{-}C_{20})$heterocycle, $(C_1\text{-}C_{20})$heterocyclyl$(C_1\text{-}C_{10})$alkyl, —$NR_aR_b$, —$NR_aC(=O)R_b$, —$NR_aC(=O)NR_aOR_b$, —$NR_aC(=O)NR_aR_b$, —$NR_aC(=O)OR_b$, —$NR_aSO_2R_b$, —$C(=O)R_a$, —$C(O)OR_a$, —$OC(=O)R_a$, —$C(=O)NR_aR_b$, —$OC(=O)NR_aR_b$, —$OR_a$, —$SR_a$, —$SOR_a$, —$S(=O)_2R_a$, —$OS(=O)_2R_a$ and —$S(=O)_2OR_a$, wherein $R_a$ and $R_b$, which may be the same or different, being each independently hydrogen, $(C_1\text{-}C_{10})$alkyl, halo$(C_1\text{-}C_{10})$alkyl, $(C_3\text{-}C_{10})$cycloalkyl, $(C_6\text{-}C_{12})$aryl, $(C_6\text{-}C_{12})$aryl$(C_1\text{-}C_{10})$alkyl, $(C_1\text{-}C_{20})$heteroaryl, $(C_1\text{-}C_{20})$heteroaryl$(C_1\text{-}C_{10})$alkyl, $(C_1\text{-}C_{20})$heterocycle, $(C_1\text{-}C_{20})$heterocycyl$(C_1\text{-}C_{10})$alkyl or —$(CH_2)_zC(=O)R_c$, z is an integer of 1, 2, 3 or 4, and $R_c$ is hydroxyl, $(C_1\text{-}C_{10})$alkyl, $(C_3\text{-}C_{10})$cycloalkyl or $(C_1\text{-}C_{10})$alkoxy.

In accordance with another aspect of the present invention, there is provided a pharmaceutical composition for preventing or treating a sex hormone-related disease comprising the compound of formula (I), or a stereoisomer, a prodrug or a pharmaceutically acceptable salt thereof.

In accordance with a further aspect of the present invention, there is provided a method of preventing or treating a sex hormone-related disease in a subject comprising the step of administering to the subject in need thereof an effective amount of the compound, or a stereoisomer, a prodrug or a pharmaceutically acceptable salt of formula (I).

In accordance with a still further aspect of the present invention, there is provided a use of the compound, or a stereoisomer, a prodrug or a pharmaceutically acceptable salt of formula (I) for the manufacture of a medicament for preventing or treating a sex hormone-related disease.

The compound of the present invention can effectively inhibit GnRH receptor, and thus can be useful in preventing or treating sex hormone-related diseases such as endometriosis, amenorrhea, irregular menstruation, uterine myoma, uterine fibroids, polycystic ovarian disease, lupus erythematous, hypertrichosis, precocious puberty, short stature, acne, alopecia, gonadal steroid-dependent neoplasms (e.g., prostate cancer, breast cancer, ovarian cancer, uterine cancer, pituitary cancer, etc.), gonadotropin-producing pituitary adenoma, sleep apnea, irritable bowel syndrome, premenstrual syndrome, benign prostatic hyperplasia, contraception, and infertility, as well as Alzheimer disease.

DETAILED DESCRIPTION OF THE INVENTION

Hereinafter, a detailed description of the present invention is given.

As used herein, the term "non-aromatic" refers to a chemical group that does not contain an aromatic character that 4n+2 electrons are conjugated or that is saturated.

As used herein, the term "alkyl" refers to a straight or branched chain, non-cyclic aliphatic hydrocarbon unsaturated or saturated, which contains 1 to 10 carbon atoms. The term "lower alkyl" has the same meaning as "alkyl" except for containing 1 to 6 carbon atoms. The term "higher alkyl" has the same meaning as "alkyl" except for containing 2 to 10 carbon atoms. Representative examples of the saturated straight alkyls include methyl, ethyl, n-propyl, n-butyl, n-pentyl, n-hexyl and the like; and representative examples of the saturated branched alkyls include isopropyl, sec-butyl, isobutyl, tert-butyl, isopentyl and the like. Unsaturated alkyl comprises at least one double or triple bonds between adjacent carbon atoms (also referred to as "alkenyl" or "alkynyl", respectively). Representative examples of the straight or branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl and the like; and representative examples of the straight or branched alkynyl include acetylenyl, propynyl, 1-butynyl, 2-butynyl, 1-pentynyl, 2-pentynyl, 3-methyl-1-butynyl and the like.

As used herein, the term "cycloalkyl" refers to a saturated or unsaturated non-aromatic carbocyclic ring system which contains 3 to 10 carbon atoms. Representative examples of the saturated cycloalkyl include cyclopropyl, cyclobutyl, cyclopentyl, cyclohexyl and the like; representative examples of the unsaturated cyclic alkyl include cyclopentenyl, cyclohexenyl and the like. Cycloalkyl is also alternatively called "homocycle" or "homocyclic ring" in the specification of the present invention.

As used herein, the term "aryl" refers to an aromatic carbocyclic group, such as phenyl or naphthyl.

As used herein, the term "arylalkyl" refers to a substituted alkyl whose at least one hydrogen atom is replaced with aryl group, such as benzyl, —(CH$_2$)$_2$phenyl, —(CH$_2$)$_3$phenyl, —CH(phenyl)$_2$ and the like.

As used herein, the term "heteroaryl" refers to a 5- to 10-membered aromatic heterocyclic ring which comprises at least one heteroatom selected from nitrogen, oxygen and sulfur atoms, and at least one carbon atom, and it comprises a mono- or bicyclic ring system. Representative examples of the heteroaryl include furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl and quinazolinyl.

As used herein, the term "heteroarylalkyl" refers to a substituted alkyl whose at least one hydrogen atom is substituted with heteroaryl group, such as —CH$_2$ pyridinyl, —CH$_2$ pyrimidinyl and the like.

As used herein, the term "heterocycle" (also referred to as "heterocyclic ring") refers to a 4- to 7-membered monocylic- or 7- to 10-membered bicyclic-heterocyclic ring which is either saturated, unsaturated, or aromatic, and which comprises 1 to 4 heteroatoms independently selected from nitrogen, oxygen and sulfur atoms (wherein the nitrogen and sulfur heteroatoms may be optionally oxidized, and the nitrogen heteroatom may be optionally quaternized). Any one of the above heterocycles includes bicyclic rings fused to a benzene ring. Heterocycle may be bonded via any heteroatom or carbon atom. Heterocycles include heteroaryls as defined above. Thus, in addition to the heteroaryls listed above, the heterocycles also include morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyridinyl, tetrahydropyrimidinyl, tetrahydrothiophenyl, tetrahydrothiopyranyl, and the like.

As used herein, the term "heterocycloalkyl" refers to a substituted alkyl whose at least one hydrogen atom is substituted with heterocycles, such as —CH$_2$morpholinyl and the like.

As used herein, the term "homocycle" (also referred to as "homocyclic ring") refers to a saturated or unsaturated (exclusive of aromatic group) carbocyclic ring containing 3 to 7 carbon atoms, such as cyclopropane, cyclobutane, cyclopentane, cyclohexane, cycloheptane, cyclohexene, and the like.

As used herein the term "substituted" refers to any groups (i.e., alkyl, aryl, arylalkyl, heteroaryl, heteroarylalkyl, homocycle, heterocycle and/or heterocyclylalkyl), wherein at least one hydrogen atom of the any group is replaced with a substituent. In the case of a keto substituent (—C(=O)—), two hydrogen atoms are replaced with the substituent.

When at least one group is substituted with the substituent, within the scope of the present invention, the "substituents" may include halogen, acetylene, vinyl, hydroxyl, cyano, nitro, amino, (C$_1$-C$_{10}$)alkylamino, di(C$_1$-C$_{10}$)alkylamino, (C$_1$-C$_{10}$)alkyl, (C$_3$-C$_{10}$)cycloalkyl, (C$_1$-C$_{10}$)alkoxy, (C$_1$-C$_{10}$)alkylthio, halo(C$_1$-C$_{10}$)alkyl, (C$_6$-C$_{12}$)aryl, (C$_6$-C$_{12}$)aryl(C$_1$-C$_{10}$)alkyl, (C$_1$-C$_{20}$)heteroaryl, (C$_1$-C$_{20}$)heteroaryl(C$_1$-C$_{10}$)alkyl, (C$_1$-C$_{20}$)heterocycle, (C$_1$-C$_{20}$)heterocycle(C$_1$-C$_{10}$)alkyl, —NR$_a$R$_b$, —NR$_a$C(=O)R$_b$, —NR$_a$C(=O)NR$_a$OR$_b$, —NR$_a$C(=O)NR$_a$R$_b$, —NR$_a$C(=O)OR$_b$, —NR$_a$SO$_2$R$_b$, —C(=O)R$_a$, —C(=O)OR$_a$, —OC(=O)R$_a$, —C(=O)NR$_a$R$_b$, —OC(=O)NR$_a$R$_b$, —OR$_a$, —SR$_a$, —SOR$_a$, —S(=O)$_2$R$_a$, —OS(=O)$_2$R$_a$, and —S(=O)$_2$OR$_a$.

Also, the substituents may be further replaced with at least one of the substituents, thus they include substituted alkyl, substituted aryl, substituted arylalkyl, substituted heterocycle and substituted heterocyclylalkyl.

In the above, R$_a$ and R$_b$, which may be the same or different, being each independently hydrogen, (C$_1$-C$_{10}$)alkyl, halo(C$_1$-C$_{10}$)alkyl, (C$_3$-C$_{10}$)cycloalkyl, (C$_6$-C$_{12}$)aryl, (C$_6$-C$_{12}$)aryl(C$_1$-C$_{10}$)alkyl, (C$_1$-C$_{20}$)heteroaryl, (C$_1$-C$_{20}$)heteroaryl(C$_1$-C$_{10}$)alkyl, (C$_1$-C$_{20}$)heterocycle, (C$_1$-C$_{20}$)heterocyclyl(C$_1$-C$_{10}$)alkyl or —(CH$_2$)$_z$C(=O)R$_c$ (in which z is an integer 1, 2, 3 or 4; and R$_c$ is hydroxyl, (C$_1$-C$_{10}$)alkyl, (C$_3$-C$_{10}$)cycloalkyl or (C$_1$-C$_{10}$)alkoxy).

As used herein, the term "halogen" refers to fluorine, chlorine, bromine or iodine.

As used herein, the term "haloalkyl" refers to a substituted alkyl whose at least one hydrogen atom is replaced with a halogen, such as trifluoromethyl and the like.

As used herein, the term "alkoxy" refers to an alkyl group bonded via an oxygen bridge (i.e., —O-alkyl), such as methoxy, ethoxy and the like.

As used herein, the term "akylthio" refers to an alkyl group bonded via a sulfur bridge (i.e., —S-alkyl), such as methylthio, ethylthio and the like.

As used herein, the term "alkylsulfonyl" refers to an alkyl group bonded via a sulfonyl bridge (i.e., —SO$_2$-alkyl), such as methylsulfonyl, ethylsulfonyl and the like.

As used herein, the term "alkylamino" and "dialkylamino" refer to one and two alkyl groups, respectively, bonded via a nitrogen bridge (i.e., —N-alkyl), such as methylamino, ethylamino, dimethylamino, diethylamino and the like.

In accordance with one embodiment of the present invention, the compound of formula (I) wherein A is O, CH$_2$, NR$_9$ or S may be represented by the structure selected from the group consisting of formulas (Ia) to (Id):

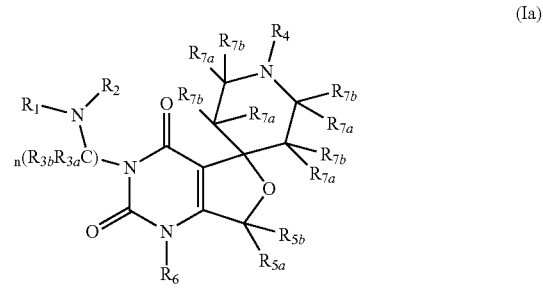
(Ia)

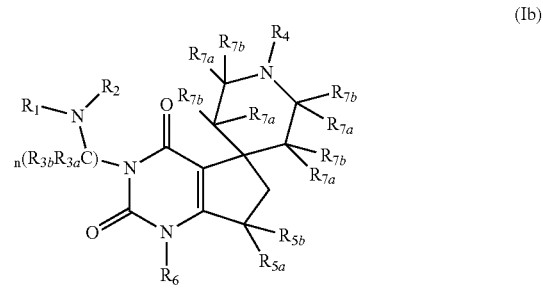
(Ib)

-continued (Ic)

(Id)

wherein, $R_1$, $R_2$, $R_{3a}$, $R_{3b}$, $R_4$, $R_{5a}$, $R_{5b}$, $R_6$, $R_{7a}$, $R_{7b}$, $R_9$ and n have the same meanings as defined in formula (I).

In accordance with one embodiment of the present invention, the compound of formula (I) wherein $R_6$ is substituted benzyl may be represented by the structure of formula (Ie):

(Ie)

wherein,

A is O, $CH_2$, $NR_9$ or S;

$R_9$ is hydrogen or $(C_1-C_{10})$alkyl;

$R_1$, $R_2$, $R_{3a}$, $R_{3b}$, $R_4$, $R_{5a}$, $R_{5b}$, $R_6$, $R_{7a}$, $R_{7b}$ and n have the same meanings as defined formula (I); and X is at least one substituent selected from the group consisting of halogen, acetylene, vinyl, hydroxy, cyano, nitro, amino, $(C_1-C_{10})$alkylamino, di$(C_1-C_{10})$alkylamino, $(C_1-C_{10})$alkyl, $(C_3-C_{10})$cycloalkyl, $(C_1-C_{10})$alkoxy, $(C_1-C_{10})$alkylthio, halo$(C_1-C_{10})$alkyl, $(C_6-C_{12})$aryl, $(C_6-C_{12})$aryl$(C_1-C_{10})$alkyl, $(C_1-C_{20})$heteroaryl, $(C_1-C_{20})$heteroaryl$(C_1-C_{10})$alkyl, $(C_1-C_{20})$heterocycle, $(C_1-C_{20})$heterocyclyl$(C_1-C_{10})$alkyl, —$NR_aR_b$, —$NR_aC(\!=\!O)R_b$, —$NR_aC(\!=\!O)NR_aR_b$, —$NR_aC(\!=\!O)NR_aR_b$, —$NR_aC(\!=\!O)OR_b$, —$NR_aSO_2R_b$, —$C(\!=\!O)R_a$, —$C(\!=\!O)OR_a$, —$OC(\!=\!O)R_a$, —$C(\!=\!O)NR_aR_b$, —$OC(\!=\!O)NR_aR_b$, —$OR_a$, —$SR_a$, —$SOR_a$, —$S(\!=\!O)_2R_a$, —$OS(\!=\!O)_2R_a$ and —$S(\!=\!O)_2OR_a$;

wherein $R_a$ and $R_b$, which may be the same or different, being each independently hydrogen, $(C_1-C_{10})$alkyl, halo$(C_1-C_{10})$alkyl, $(C_3-C_{10})$cycloalkyl, $(C_6-C_{12})$aryl, $(C_6-C_{12})$aryl$(C_1-C_{10})$alkyl, $(C_1-C_{20})$heteroaryl, $(C_1-C_{20})$heteroaryl$(C_1-C_{10})$alkyl, $(C_1-C_{20})$heterocycle, $(C_1-C_{20})$heterocyclyl$(C_1-C_{10})$alkyl or —$(CH_2)_zC(\!=\!O)R_c$, z is an integer of 1, 2, 3 or 4, and $R_c$ is hydroxyl, $(C_1-C_{10})$alkyl, $(C_3-C_{10})$cycloalkyl or $(C_1-C_{10})$alkoxy.

In accordance with preferred embodiment of the present invention, the compound of formula (I) may be selected from the group consisting of formulas (II) to (VI):

(II)

(III)

(IV)

(V)

-continued

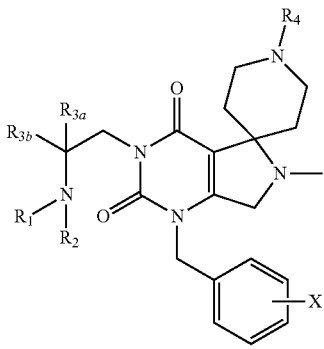
(VI)

wherein, $R_1$, $R_2$, $R_{3a}$, $R_{3b}$ and $R_4$ have the same meanings as defined in formula (I); and X has the same meaning as defined in formula (Ie).

In accordance with one embodiment of the present invention, the compound of formula (I) wherein n is 2, $R_{3a}$ is H, $R_{3b}$ is aromatic ring or substituted aromatic ring and $R_6$ is substituted benzyl may be represented by the structure of the following formula (VII):

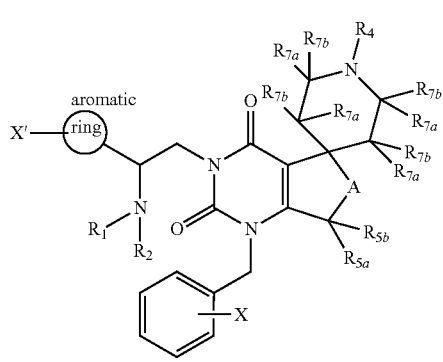
(VII)

wherein,

A is O, S, $CH_2$ or $NR_9$;

$R_9$ is H or $(C_1-C_{10})$alkyl;

$R_1$, $R_2$, $R_4$, $R_{5a}$, $R_{5b}$, $R_{7a}$ and $R_{7b}$ have the same meanings as defined in formula (I); and X and X' are each independently at least one substituent selected from the group consisting of halogen, acetylene, vinyl, hydroxy, cyano, nitro, amino, $(C_1-C_{10})$alkylamino, di$(C_1-C_{10})$alkylamino, $(C_1-C_{10})$alkyl, $(C_3-C_{10})$cycloalkyl, $(C_1-C_{10})$alkoxy, $(C_1-C_{10})$alkylthio, halo$(C_1-C_{10})$alkyl, $(C_6-C_{12})$aryl, $(C_6-C_{12})$aryl$(C_1-C_{10})$alkyl, $(C_1-C_{20})$heteroaryl, $(C_1-C_{20})$heteroaryl$(C_1-C_{10})$alkyl, $(C_1-C_{20})$heterocycle, $(C_1-C_{20})$heterocyclyl$(C_1-C_{10})$alkyl, $-NR_aR_b$, $-NR_aC(=O)R_b$, $-NR_aC(=O)NR_aOR_b$, $-NR_aC(=O)NR_aR_b$, $-NR_aC(=O)OR_b$, $-NR_aSO_2R_b$, $-C(=O)R_a$, $-C(=O)OR_a$, $-OC(=O)R_a$, $-C(=O)NR_aR_b$, $-OC(=O)NR_aR_b$, $-OR_a$, $-SR_a$, $-SOR_a$, $-S(=O)_2R_a$, $-OS(=O)_2R_a$ and $-S(=O)_2OR_a$;

wherein $R_a$ and $R_b$, which may be the same or different, being each independently hydrogen, $(C_1-C_{10})$alkyl, halo$(C_1-C_{10})$alkyl, $(C_3-C_{10})$cycloalkyl, $(C_6-C_{12})$aryl, $(C_6-C_{12})$aryl$(C_1-C_{10})$alkyl, $(C_1-C_{20})$heteroaryl, $(C_1-C_{20})$heteroaryl$(C_1-C_{10})$alkyl, $(C_1-C_{20})$heterocycle, $(C_1-C_{20})$heterocyclyl$(C_1-C_{10})$alkyl or $-(CH_2)_zC(=O)R_c$, z is an integer of 1, 2, 3 or 4, and $R_c$ is hydroxyl, $(C_1-C_{10})$alkyl, $(C_3-C_{10})$cycloalkyl or $(C_1-C_{10})$alkoxy.

In a preferred embodiment of the compound of formula (I),

A is $CH_2$, O, S or $NR_9$ wherein $R_9$ is hydrogen or methyl;

n is an integer of 2;

$R_1$ and $R_2$ being each independently hydrogen, $(C_6-C_{12})$aryl$(C_1-C_{10})$alkyl, substituted $(C_6-C_{12})$aryl$(C_1-C_{10})$alkyl, $(C_1-C_{20})$heteroaryl$(C_1-C_{10})$alkyl, substituted $(C_1-C_{20})$heteroaryl$(C_1-C_{10})$alkyl or $-(CH_2)_s-R_{12}$;

s is an integer of 1, 2, 3 or 4;

$R_{3a}$ and $R_{3b}$ being each independently hydrogen, $(C_6-C_{12})$aryl, substituted $(C_6-C_{12})$aryl, $(C_1-C_{20})$heteroaryl or substituted $(C_1-C_{20})$heteroaryl;

$R_4$ is hydrogen, $(C_6-C_{12})$aryl, substituted $(C_6-C_{12})$aryl, $(C_1-C_{20})$heteroaryl, substituted $(C_1-C_{10})$heteroaryl, $(C_6-C_{12})$aryl$(C_1-C_{10})$alkyl, substituted $(C_6-C_{12})$aryl$(C_1-C_{10})$alkyl, $(C_1-C_{20})$heteroaryl$(C_1-C_{10})$alkyl, substituted $(C_1-C_{20})$heteroaryl$(C_1-C_{10})$alkyl, $(C_1-C_{10})$alkyl, substituted $(C_1-C_{10})$alkyl, $-C(=O)R_{11}$, $-SO_2R_{11}$ or $-C(=O)OR_{11}$;

$R_6$ is $(C_6-C_{12})$aryl$(C_1-C_{10})$alkyl, substituted $(C_6-C_{12})$aryl$(C_1-C_{10})$alkyl, $(C_1-C_{20})$heteroaryl$(C_1-C_{10})$alkyl or substituted $(C_1-C_{20})$heteroaryl$(C_1-C_{10})$alkyl;

$R_{5a}$, $R_{5b}$, $R_{7a}$, $R_{7b}$, $R_{8a}$ and $R_{8b}$ being each independently hydrogen;

$R_{11}$ is hydrogen, $(C_1-C_{10})$alkyl, $(C_6-C_{12})$aryl, or $(C_6-C_{12})$aryl$(C_1-C_{10})$alkyl; and $R_{12}$ is $-COOH$ or an acid isostere selected from the group consisting of:

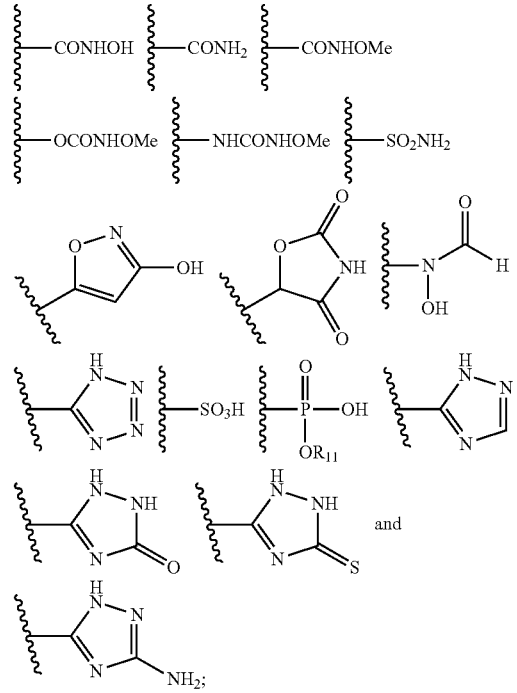

wherein, "substituted" being intended to mean replacement with at least one substituent selected from the group consisting of halogen, acetylene, vinyl, hydroxy, cyano, nitro, amino, $(C_1-C_{10})$alkylamino, di$(C_1-C_{10})$alkylamino, $(C_1-C_{10})$alkyl, $(C_3-C_{10})$cycloalkyl, $(C_1-C_{10})$alkoxy, $(C_1-C_{10})$alkylthio, halo$(C_1-C_{10})$alkyl, $-NR_aR_b$, $-NR_aC(=O)R_b$, $-NR_aC(=O)NR_aOR_b$, $-NR_aC(=O)NR_aR_b$, $-NR_aC$ (=O)OR$_b$, —NR$_a$SO$_2$R$_b$, —C(=O)R$_a$, —C(=O)OR$_a$, —OC(=O)R$_a$, —C(=O)NR$_a$R$_b$, —OC(=O)NR$_a$R$_b$, —OR$_a$, —SR$_a$, and —S(=O)$_2$R$_a$, wherein R$_a$ and R$_b$ being each independently hydrogen, (C$_1$-C$_{10}$)alkyl, halo(C$_1$-C$_{10}$)alkyl, (C$_3$-C$_{10}$)cycloalkyl, (C$_6$-C$_{12}$)aryl, (C$_6$-C$_{12}$)aryl(C$_1$-C$_{10}$)alkyl, (C$_1$-C$_{20}$)heteroaryl, (C$_1$-C$_{20}$)heteroaryl(C$_1$-C$_{10}$)alkyl, (C$_1$-C$_{20}$)heterocycle, (C$_1$-C$_{20}$)heterocyclyl(C$_1$-C$_{10}$)alkyl or —(CH$_2$)$_z$C(=O)R$_c$, z is an integer of 1, 2, 3 or 4, and R$_c$ is hydroxyl, (C$_1$-C$_{10}$)alkyl, (C$_3$-C$_{10}$)cycloalkyl or (C$_1$-C$_{10}$)alkoxy.

The compound of formula (I) of the present invention may be selected from the group consisting of:

(R)-3-(2-amino-2-phenylethyl)-1-(2-fluoro-6-(trifluoromethyl)benzyl)-1'-((5-(trifluoromethyl)furan-2-yl)methyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(3-fluorobenzyl)-1H-spiro[furo[3,4-d]pyrimidine-5,4'-piperidine]-2,4(3H,7H)-dione;

(R)-4-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-phenylethyl)amino)butanoic acid;

(R)-3-(2-amino-2-phenylethyl)-1-(2-fluoro-6-(trifluoromethyl)benzyl)-1'-methyl-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(2-methoxyethyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-neopentyl-1H-spiro[furo[3,4-d]pyrimidine-5,4'-piperidine]-2,4(3H,7H)-dione;

3-((R)-2-amino-2-phenylethyl)-1-(2-fluoro-6-(trifluoromethyl)benzyl)-1'-(2-(1-methylpyrrolidin-2-yl)ethyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(pyridin-2-ylmethyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(pyridin-3-ylmethyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(pyridin-4-ylmethyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-((5-fluoropyridin-3-yl)methyl)-1H-spiro[furo[3,4-d]pyrimidine-5,4'-piperidine]-2,4(3H,7H)-dione;

(R)-3-(2-amino-2-phenylethyl)-1'-((2-chloropyridin-3-yl)methyl)-1-(2-fluoro-6-(trifluoromethyl)benzyl)-1H-spiro[furo[3,4-d]pyrimidine-5,4'-piperidine]-2,4(3H,7H)-dione;

(R)-3-(2-amino-2-phenylethyl)-1'-((6-chloropyridin-3-yl)methyl)-1-(2-fluoro-6-(trifluoromethyl)benzyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-((5-methylpyridin-3-yl)methyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-((6-(trifluoromethyl)pyridin-2-yl)methyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(3-methylbenzyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(3-methoxybenzyl)-1H-spiro[furo[3,4-d]pyrimidine-5,4'-piperidine]-2,4(3H,7H)-dione;

(R)-3-((3-(2-amino-2-phenylethyl)-1-(2-fluoro-6-(trifluoromethyl)benzyl)-2,4-dioxo-2,3,4,7-tetrahydro-1H-spiro[furo[3,4-d]pyrimidine-5,4'-piperidine]-1'-yl)methyl)benzonitrile;

(R)-3-(2-amino-2-phenylethyl)-1'-(3-chlorobenzyl)-1-(2-fluoro-6-(trifluoromethyl)benzyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(3-(trifluoromethyl)benzyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(3-(trifluoromethoxy)benzyl)-1H-spiro[furo[3,4-d]pyrimidine-5,4'-piperidine]-2,4(3H,7H)-dione;

(R)-methyl 3-((3-(2-amino-2-phenylethyl)-1-(2-fluoro-6-(trifluoromethyl)benzyl)-2,4-dioxo-2,3,4,7-tetrahydro-1H-spiro[furo[3,4-d]pyrimidine-5,4'-piperidin]-1'-yl)methyl)benzoate;

(R)-3-((3-(2-amino-2-phenylethyl)-1-(2-fluoro-6-(trifluoromethyl)benzyl)-2,4-dioxo-2,3,4,7-tetrahydro-1H-spiro[furo[3,4-d]pyrimidine-5,4'-piperidin]-1'-yl)methyl)-N-methylbenzamide;

(R)-3-(2-amino-2-phenylethyl)-1-(2-fluoro-6-(trifluoromethyl)benzyl)-1'-(3-(methylthio)benzyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(3-hydroxybenzyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(3-(methylsulfonyl)benzyl)-1H-spiro[furo[3,4-d]pyrimidine-5,4'-piperidine]-2,4(3H,7H)-dione;

(R)-3-(2-amino-2-phenylethyl)-1'-(benzo[b]thiophen-7-ylmethyl)-1-(2-fluoro-6-(trifluoromethyl)benzyl)-1H-spiro[furo[3,4-d]pyrimidine-5,4'-piperidine]-2,4(3H,7H)-dione;

(R)-3-(2-amino-2-phenylethyl)-1'-(benzo[c][1,2,5]oxadiazol-4-ylmethyl)-1-(2-fluoro-6-(trifluoromethyl)benzyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(2-methylbenzyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(2-methoxybenzyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(2-hydroxybenzyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(2-fluorobenzyl)-1H-spiro[furo[3,4-d]pyrimidine-5,4'-piperidine]-2,4(3H,7H)-dione;

(R)-2-((3-(2-amino-2-phenylethyl)-1-(2-fluoro-6-(trifluoromethyl)benzyl)-2,4-dioxo-2,3,4,7-tetrahydro-1H-spiro[furo[3,4-d]pyrimidine-5,4'-piperidin]-1'-yl)methyl)benzonitrile;

(R)-3-(2-amino-2-phenylethyl)-1'-(2,3-difluorobenzyl)-1-(2-fluoro-6-(trifluoromethyl)benzyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(2-(trifluoromethyl)benzyl)-1H-spiro[furo[3,4-d]pyrimidine-5,4'-piperidine]-2,4(3H,7H)-dione;

(R)-2-((3-(2-amino-2-phenylethyl)-1-(2-fluoro-6-(trifluoromethyl)benzyl)-2,4-dioxo-2,3,4,7-tetrahydro-1H-spiro[furo[3,4-d]pyrimidine-5,4'-piperidin]-1'-yl)methyl)-6-fluorobenzonitrile;

(R)-3-((3-(2-amino-2-phenylethyl)-1-(2-fluoro-6-(trifluoromethyl)benzyl)-2,4-dioxo-2,3,4,7-tetrahydro-1H-spiro[furo[3,4-d]pyrimidine-5,4'-piperidine]-1'-yl)methyl)-2-fluorobenzonitrile;

(R)-3-(2-amino-2-phenylethyl)-1-(2,6-difluorobenzyl)-1'-(3-(trifluoromethyl)benzyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(2-(trifluoromethoxy)benzyl)-1H-spiro[furo[3,4-d]pyrimidine-5,4'-piperidine]-2,4(3H,7H)-dione;

(R)-methyl 2-((3-(2-amino-2-phenylethyl)-1-(2-fluoro-6-(trifluoromethyl)benzyl)-2,4-dioxo-2,3,4,7-tetrahydro-1H-spiro[furo[3,4-d]pyrimidine-5,4'-piperidin]-1'-yl)methyl)benzoate;

(R)-3-(2-amino-2-phenylethyl)-1'-(2-chlorobenzyl)-1-(2-fluoro-6-(trifluoromethyl)benzyl)-1H-spiro[furo[3,4-d]pyrimidine-5,4'-piperidine]-2,4(3H,7H)-dione;

(R)-3-(2-amino-2-phenylethyl)-1'-(2-fluoro-3-methoxybenzyl)-1-(2-fluoro-6-(trifluoromethyl)benzyl)-1H-spiro[furo[3,4-d]pyrimidine-5,4'-piperidine]-2,4(3H,7H)-dione;

(R)-5-((3-(2-amino-2-phenylethyl)-1-(2-fluoro-6-(trifluoromethyl)benzyl)-2,4-dioxo-2,3,4,7-tetrahydro-1H-spiro[furo[3,4-d]pyrimidine-5,4'-piperidine]-1'-yl)methyl)furan-2-carboxamide;

(R)-5-((3-(2-amino-2-phenylethyl)-1-(2-fluoro-6-(trifluoromethyl)benzyl)-2,4-dioxo-2,3,4,7-tetrahydro-1H-spiro[furo[3,4-d]pyrimidine-5,4'-piperidin]-1'-yl)methyl)-N-methylfuran-2-carboxamide;

(R)-3-(2-amino-2-phenylethyl)-1-(2,6-difluorobenzyl)-1'-((5-(trifluoromethyl)furan-2-yl)methyl)-1H-spiro[furo[3,4-d]pyrimidine-5,4'-piperidine]-2,4(3H,7H)-dione;

(R)-3-(2-amino-2-phenylethyl)-1'-(3-chlorobenzyl)-1-(2,6-difluorobenzyl)-1H-spiro[furo[3,4-d]pyrimidine-5,4'-piperidine]-2,4(3H,7H)-dione;

(R)-3-((3-(2-amino-2-phenylethyl)-1-(2,6-difluorobenzyl)-2,4-dioxo-2,3,4,7-tetrahydro-1H-spiro[furo[3,4-d]pyrimidine-5,4'-piperidin]-1'-yl)methyl)benzonitrile;

(R)-3-(2-amino-2-phenylethyl)-1-(2-fluoro-6-(trifluoromethyl)benzyl)-1'-phenethyl-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(furan-2-ylmethyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-((5-methylfuran-2-yl)methyl)-1H-spiro[furo[3,4-d]pyrimidine-5,4'-piperidine]-2,4(3H,7H)-dione;

(R)-3-(2-amino-2-phenylethyl)-1'-((5-chlorofuran-2-yl)methyl)-1-(2-fluoro-6-(trifluoromethyl)benzyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-((6-hydroxypyridine-3-yl)methyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(4-methylbenzyl)-1H-spiro[furo[3,4-d]pyrimidine-5,4'-piperidine]-2,4(3H,7H)-dione;

(R)-3-(2-amino-2-phenylethyl)-1'-(4-chlorobenzyl)-1-(2-fluoro-6-(trifluoromethyl)benzyl)-1H-spiro[furo[3,4-d]pyrimidine-5,4'-piperidine]-2,4(3H,7H)-dione;

(R)-4-((3-(2-amino-2-phenylethyl)-1-(2-fluoro-6-(trifluoromethyl)benzyl)-2,4-dioxo-2,3,4,7-tetrahydro-1H-spiro[furo[3,4-d]pyrimidine-5,4'-piperidin]-1'-yl)methyl)benzonitrile (R)-3-(2-amino-2-phenylethyl)-1-(2-fluoro-6-(trifluoromethyl)benzyl)-1'-(4-(trifluoromethyl)benzyl)-1H-spiro[furo[3,4-d]pyrimidine-5,4'-piperidine]-2,4(3H,7H)-dione;

(R)-methyl 4-((3-(2-amino-2-phenylethyl)-1-(2-fluoro-6-(trifluoromethyl)benzyl)-2,4-dioxo-2,3,4,7-tetrahydro-1H-spiro[furo[3,4-d]pyrimidine-5,4'-piperidin]-1'-yl)methyl)benzoate (R)-3-(2-amino-2-phenylethyl)-1-(2-fluoro-6-(trifluoromethyl)benzyl)-1'-(4-fluorobenzyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(4-hydroxybenzyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(4-methoxybenzyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(pyrazin-2-ylmethyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-((1-methyl-1H-pyrazol-5-yl)methyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(thiazol-4-ylmethyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(thiazol-5-ylmethyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(thiazol-2-ylmethyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(oxazol-4-ylmethyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(isooxazol-3-ylmethyl)-1H-spiro[furo[3,4-d]pyrimidine-5,4'-piperidine]-2,4(3H,7H)-dione;

(R)-1'-acetyl-3-(2-amino-2-phenylethyl)-1-(2-fluoro-6-(trifluoromethyl)benzyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-isobutyryl-1H-spiro[furo[3,4-d]pyrimidine-5,4'-piperidine]-2,4(3H,7H)-dione;

(R)-ethyl 3-(2-amino-2-phenylethyl)-1-(2-fluoro-6-(trifluoromethyl)benzyl)-2,4-dioxo-2,3,4,7-tetrahydro-1H-spiro[furo[3,4-d]pyrimidine-5,4'-piperidine]-1'-carboxylate;

(R)-3-(2-amino-2-phenylethyl)-1-(2-fluoro-6-(trifluoromethyl)benzyl)-1'-(methylsulfonyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(2-(methylsulfonyl)ethyl)-1H-spiro[furo[3,4-d]pyrimidine-5,4'-piperidine]-2,4(3H,7H)-dione;

(R)-3-((3-(2-amino-2-phenylethyl)-1-(2-fluoro-6-(trifluoromethyl)benzyl)-2,4-dioxo-2,3,4,7-tetrahydro-1H-spiro[furo[3,4-d]pyrimidine-5,4'-piperidin]-1'-yl)methyl)benzamide;

(R)-4-((3-(2-amino-2-phenylethyl)-1-(2-fluoro-6-(trifluoromethyl)benzyl)-2,4-dioxo-2,3,4,7-tetrahydro-1H-spiro[furo[3,4-d]pyrimidine-5,4'-piperidin]-1'-yl)methyl)benzamide;

(R)—N-(2-(3-(2-amino-2-phenylethyl)-1-(2-fluoro-6-(trifluoromethyl)benzyl)-2,4-dioxo-2,3,4,7-tetrahydro-1H-spiro[furo[3,4-d]pyrimidine-5,4'-piperidin]-1'-yl)ethyl)-N-methylmethanesulfonamide;

(R)-3-(2-amino-2-phenylethyl)-1-(2-fluoro-6-(trifluoromethyl)benzyl)-1'-(2-morpholinoethyl)-1H-spiro[furo[3,4-d]pyrimidine-5,4'-piperidine]-2,4(3H,7H)-dione;

(R)-4-((2-(1'-(3-chlorobenzyl)-1-(2-fluoro-6-(trifluoromethyl)benzyl)-2,4-dioxo-1H-spiro[furo[3,4-d]pyrimidine-5,4'-piperidin]-3(2H,4H,7H)-yl)-1-phenylethyl)amino)butanoic acid;

(R)-4-((2-(1-(2-fluoro-6-(trifluoromethyl)benzyl)-2,4-dioxo-1'-(3-(trifluoromethyl)benzyl)-1H-spiro[furo[3,4-d]pyrimidine-5,4'-piperidin]-3(2H,4H,7H)-yl)-1-phenylethyl)amino)butanoic acid;

(R)-4-((2-(1-(2,6-difluorobenzyl)-2,4-dioxo-1'-(3-(trifluoromethyl)benzyl)-1H-spiro[furo[3,4-d]pyrimidine-5,4'-piperidin]-3(2H,4H,7H)-yl)-1-phenylethyl)amino)butanoic acid;

(R)-4-((2-(1-(2-fluoro-6-(trifluoromethyl)benzyl)-1'-((5-methylfuran-2-yl)methyl)-2,4-dioxo-1H-spiro[furo[3,4-d]pyrimidine-5,4'-piperidin]-3(2H,4H,7H)-yl)-1-phenylethyl)amino)butanoic acid;

(R)-4-((2-(1'-((5-chlorofuran-2-yl)methyl)-1-(2-fluoro-6-(trifluoromethyl)benzyl)-2,4-dioxo-1H-spiro[furo[3,4-d]pyrimidine-5,4'-piperidin]-3(2H,4H,7H)-yl)-1-phenylethyl)amino)butanoic acid;

(R)-4-((2-(1'-(3-cyano-2-fluorobenzyl)-1-(2-fluoro-6-(trifluoromethyl)benzyl)-2,4-dioxo-1H-spiro[furo[3,4-d]pyrimidine-5,4'-piperidin]-3(2H,4H,7H)-yl)-1-phenylethyl)amino)butanoic acid;

(R)-4-((2-(1-(2,6-difluorobenzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-phenylethyl)amino)butanoic acid;

(R)-4-((2-(1'-(3-chlorobenzyl)-1-(2,6-difluorobenzyl)-2,4-dioxo-1H-spiro[furo[3,4-d]pyrimidine-5,4'-piperidin]-3(2H,4H,7H)-yl)-1-phenylethyl)amino)butanoic acid;

(R)-4-((2-(1'-(3-cyanobenzyl)-1-(2,6-difluorobenzyl)-2,4-dioxo-1H-spiro[furo[3,4-d]pyrimidine-5,4'-piperidin]-3(2H,4H,7H)-yl)-1-phenylethyl)amino)butanoic acid;

(R)-4-((2-(1'-(3-cyanobenzyl)-1-(2-fluoro-6-(trifluoromethyl)benzyl)-2,4-dioxo-1H-spiro[furo[3,4-d]pyrimidine-5,4'-piperidin]-3(2H,4H,7H)-yl)-1-phenylethyl)amino)butanoic acid;

(R)-4-((2-(1-(2-fluoro-6-(trifluoromethyl)benzyl)-1'-(3-(methylcarbamoyl)benzyl)-2,4-dioxo-1H-spiro[furo[3,4-d]pyrimidine-5,4'-piperidin]-3(2H,4H,7H)-yl)-1-phenylethyl)amino)butanoic acid;

(R)-4-((2-(1-(2-fluoro-6-(trifluoromethyl)benzyl)-1'-(3-(methylthio)benzyl)-2,4-dioxo-1H-spiro[furo[3,4-d]pyrimidine-5,4'-piperidin]-3(2H,4H,7H)-yl)-1-phenylethyl)amino)butanoic acid;

(R)-4-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-phenylethyl)amino)butanamide;

(R)-4-((2-(1-(2-fluoro-6-(trifluoromethyl)benzyl)-2,4-dioxo-1'-((5-(trifluoromethyl)furan-2-yl)methyl)-1,2,6,7-tetrahydrospiro[cyclopenta[d]pyrimidine-5,4'-piperidin]-3(4H)-yl)-1-phenylethyl)amino)butanoic acid;

(R)-3-(2-amino-2-phenylethyl)-1-(2-fluoro-6-(trifluoromethyl)benzyl)-1'-((5-(trifluoromethyl)furan-2-yl)methyl)-6,7-dihydrospiro[cyclopenta[d]pyrimidine-5,4'-piperidine]-2,4(1H,3H)-dione;

(R)-3-(2-amino-2-phenylethyl)-1'-(3-chlorobenzyl)-1-(2-fluoro-6-(trifluoromethyl)benzyl)-6,7-dihydrospiro[cyclopenta[d]pyrimidine-5,4'-piperidine]-2,4(1H,3H)-dione;

(R)-4-((2-(1'-(3-chlorobenzyl)-1-(2-fluoro-6-(trifluoromethyl)benzyl)-2,4-dioxo-1,2,6,7-tetrahydrospiro[cyclopenta[d]pyrimidine-5,4'-piperidin]-3(4H)-yl)-1-phenylethyl)amino)butanoic acid;

(R)-3-(2-amino-2-phenylethyl)-1-(2-fluoro-6-(trifluoromethyl)benzyl)-1'-(3-(methylthio)benzyl)-6,7-dihydrospiro[cyclopenta[d]pyrimidine-5,4'-piperidine]-2,4(1H,3H)-dione;

(R)-3-(2-amino-2-phenylethyl)-1-benzyl-1-(2-fluoro-6-(trifluoromethyl)benzyl)-6,7-dihydrospiro[cyclopenta[d]pyrimidine-5,4'-piperidine]-2,4(1H,3H)-dione;

(R)-3-(2-amino-2-phenylethyl)-1-(2-fluoro-6-(trifluoromethyl)benzyl)-1 ?(3-fluorobenzyl)-6,7-dihydrospiro[cyclopenta[d]pyrimidine-5,4'-piperidine]-2,4(1H,3H)-dione;

(R)-3-(2-amino-2-phenylethyl)-1-(2-fluoro-6-(trifluoromethyl)benzyl)-1'-(3-(trifluoromethyl)benzyl)-6,7-dihydrospiro[cyclopenta[d]pyrimidine-5,4'-piperidine]-2,4(1H,3H)-dione;

(R)-3-(2-amino-2-phenylethyl)-1-((5-chlorofuran-2-yl)methyl)-1-(2-fluoro-6-(trifluoromethyl)benzyl)-6,7-dihydrospiro[cyclopenta[d]pyrimidine-5,4'-piperidine]-2,4(1H,3H)-dione;

(R)-3-(2-amino-2-phenylethyl)-1-(2-fluoro-6-(trifluoromethyl)benzyl)-1'-((5-(trifluoromethyl)furan-2-yl)methyl)-6,7-dihydrospiro[cyclopenta[d]pyrimidine-5,4'-piperidine]-2,4(1H,3H)-dione;

(R)-4-((2-(1-(2-fluoro-6-(trifluoromethyl)benzyl)-1-(3-(methylthio)benzyl)-2,4-dioxo-1,2,6,7-tetrahydrospiro[cyclopenta[d]pyrimidine-5,4'-piperidin]-3 (4H)-yl)-1-phenylethyl)amino)butanoic acid;

(R)-4-((2-(1'-benzyl-1-(2-fluoro-6-(trifluoromethyl)benzyl)-2,4-dioxo-1,2,6,7-tetrahydrospiro[cyclopenta[d]pyrimidine-5,4'-piperidin]-3 (4H)-yl)-1-phenylethyl)amino) butanoic acid;

(R)-4-((2-(1-(2-fluoro-6-(trifluoromethyl)benzyl)-1-(3-fluorobenzyl)-2,4-dioxo-1,2,6,7-tetrahydrospiro[cyclopenta[d]pyrimidine-5,4'-piperidin]-3 (4H)-yl)-1-phenylethyl)amino)butanoic acid;

(R)-4-((2-(1-(2-fluoro-6-(trifluoromethyl)benzyl)-2,4-dioxo-1'-(3-(trifluoromethyl)benzyl)-1,2,6,7-tetrahydrospiro[cyclopenta[d]pyrimidine-5,4'-piperidin]-3 (4H)-yl)-1-phenylethyl)amino)butanoic acid;

(R)-4-((2-(1'-((5-chlorofuran-2-yl)methyl)-1-(2-fluoro-6-(trifluoromethyl)benzyl)-2,4-dioxo-1,2,6,7-tetrahydrospiro[cyclopenta[d]pyrimidine-5,4'-piperidin]-3 (4H)-yl)-1-phenylethyl)amino)butanoic acid;

(R)-4-((2-(1-(2-fluoro-6-(trifluoromethyl)benzyl)-2,4-dioxo-1'-((5-(trifluoromethyl)furan-2-yl)methyl)-1,2,6,7-tetrahydrospiro[cyclopenta[d]pyrimidine-5,4'-piperidin]-3(4H)-yl)-1-phenylethyl)amino)butanoic acid;

(R)-4-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidin-5,4'-piperidin]-3(2H,4H,7H)-yl)-1-phenylethyl)amino)butanoic acid;

(S)-4-((2-(1-(2-fluoro-6-(trifluoromethyl)benzyl)-2,4-dioxo-1'-((5-(trifluoromethyl)furan-2-yl)methyl)-1H-spiro

[furo[3,4-d]pyrimidine-5,4'-piperidin]-3(2H,4H,7H)-yl)-1-phenylethyl)amino)butanoic acid;

(S)-4-((2-(1'-(3-chlorobenzyl)-1-(2-fluoro-6-(trifluoromethyl)benzyl)-2,4-dioxo-1H-spiro[furo[3,4-d]pyrimidine-5,4'-piperidin]-3(2H,4H,7H)-yl)-1-phenylethyl)amino)butanoic acid;

(R)-3-(2-((3-(2H-tetrazol-5-yl)propyl)amino)-2-phenylethyl)-1-(2-fluoro-6-(trifluoromethyl)benzyl)-1'-((5-(trifluoromethyl)furan-2-yl)methyl)-1H-spiro[furo[3,4-d]pyrimidine-5,4'-piperidine]-2,4(3H,7H)-dione;

(R)-2-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-phenylethyl)amino)ethyl methoxycarbamate;

(R)—N-(3-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3 (2H,4H,7H)-yl)-1-phenylethyl)amino)propyl)-N-hydroxyformamide;

4-((2-(1-(2-fluoro-6-(trifluoromethyl)benzyl)-2,4-dioxo-1'-((5-(trifluoromethyl) furan-2-yl)methyl)-1H-spiro[furo[3,4-d]pyrimidine-5,4'-piperidin]-3(2H,4H,7H)-yl)-1-(6-methylpyridin-2-yl)ethyl)amino)butanoic acid;

4-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-(5-methylthiophen-2-yl)ethyl)amino)butanoic acid;

4-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-(5-methylfuran-2-yl)ethyl)amino)butanoic acid;

4-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-(3-hydroxyphenyl)ethyl)amino)butanoic acid;

(R)-4-((2-(1'-((5-bromofuran-2-yl)methyl)-1-(2-fluoro-6-(trifluoromethyl)benzyl)-2,4-dioxo-1H-spiro[furo[3,4-d]pyrimidine-5,4'-piperidin]-3(2H,4H,7H)-yl)-1-phenylethyl)amino)butanoic acid;

4-((2-(1'-((5-ethenylfuran-2-yl)methyl)-1-(2-fluoro-6-(trifluoromethyl)benzyl)-2,4-dioxo-1H-spiro[furo[3,4-d]pyrimidine-5,4'-piperidin]-3(2H,4H,7H)-yl)-1-(5-methylfuran-2-yl)ethyl)amino)butanoic acid;

4-((2-(1'-(benzofuran-2-ylmethyl)-1-(2-fluoro-6-(trifluoromethyl)benzyl)-2,4-dioxo-1H-spiro[furo[3,4-d]pyrimidine-5,4'-piperidin]-3(2H,4H,7H)-yl)-1-(5-methylfuran-2-yl)ethyl)amino)butanoic acid;

(R)-4-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-phenylethyl)amino)-N-hydroxybutanamide;

(R)-2-(4-(1-amino-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)phenoxy)acetic acid;

4-(3-(1-amino-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)phenoxy)butanoic acid;

2-(3-(1-amino-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)phenoxy)acetic acid;

(R)-4-(4-(1-amino-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)phenoxy)butanoic acid;

3-((3-(1-amino-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)phenyl)amino)propionic acid;

2-((3-(1-amino-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)phenyl)amino)acetic acid;

3-((3-(1-amino-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)phenyl)amino)propionic acid;

3-(2-amino-2-(3-aminophenyl)ethyl)-1-(2-fluoro-6-(trifluoromethyl)benzyl)-1'-((5-(trifluoromethyl)furan-2-yl)methyl)-1H-spiro[furo[3,4-d]pyrimidine-5,4'-piperidine]-2,4(3H,7H)-dione;

3-(2-amino-2-(3-nitrophenyl)ethyl)-1-(2-fluoro-6-(trifluoromethyl)benzyl)-1'-((5-(trifluoromethyl)furan-2-yl)methyl)-1H-spiro[furo[3,4-d]pyrimidine-5,4'-piperidine]-2,4(3H,7H)-dione;

3-(2-amino-2-(4-nitrophenyl)ethyl)-1-(2-fluoro-6-(trifluoromethyl)benzyl)-1'-((5-(trifluoromethyl)furan-2-yl)methyl)-1H-spiro[furo[3,4-d]pyrimidine-5,4'-piperidine]-2,4(3H,7H)-dione;

3-(2-amino-2-(4-aminophenyl)ethyl)-1-(2-fluoro-6-(trifluoromethyl)benzyl)-1'-((5-(trifluoromethyl)furan-2-yl)methyl)-1H-spiro[furo[3,4-d]pyrimidine-5,4'-piperidine]-2,4(3H,7H)-dione;

3-(2-amino-2-(2-aminophenyl)ethyl)-1-(2-fluoro-6-(trifluoromethyl)benzyl)-1'-((5-(trifluoromethyl)furan-2-yl)methyl)-1H-spiro[furo[3,4-d]pyrimidine-5,4'-piperidine]-2,4(3H,7H)-dione;

3-(2-amino-2-(2-nitrophenyl)ethyl)-1-(2-fluoro-6-(trifluoromethyl)benzyl)-1'-((5-(trifluoromethyl)furan-2-yl)methyl)-1H-spiro[furo[3,4-d]pyrimidine-5,4'-piperidine]-2,4(3H,7H)-dione;

tert-butyl(2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-(3-(3-methoxyureido)phenyl)ethyl)carbamate;

1-(3-(1-amino-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)phenyl)-3-methylurea; and N-(3-(1-amino-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)phenyl)acetamide.

The compounds of the present invention can be prepared by the well-known organic synthesis methods comprising the method illustrated in the following Example section.

A compound (iv) as an intermediate for preparing the compound of formula (I) wherein A is O, S or substituted N, may be prepared according to the procedure shown in Reaction Scheme 1.

[Reaction Scheme 1]

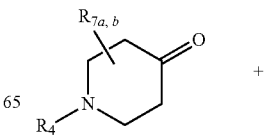

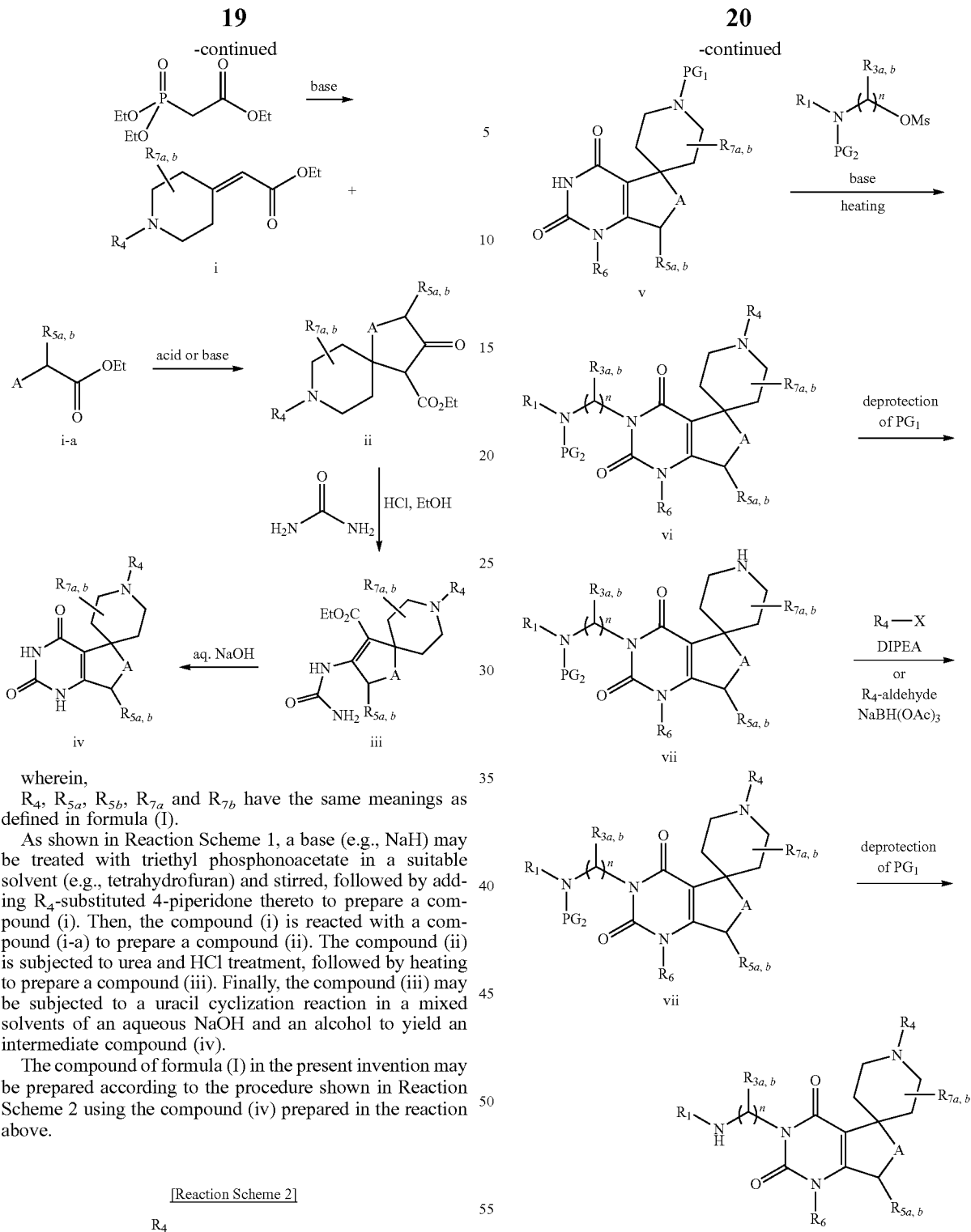

wherein,
R$_4$, R$_{5a}$, R$_{5b}$, R$_{7a}$ and R$_{7b}$ have the same meanings as defined in formula (I).

As shown in Reaction Scheme 1, a base (e.g., NaH) may be treated with triethyl phosphonoacetate in a suitable solvent (e.g., tetrahydrofuran) and stirred, followed by adding R$_4$-substituted 4-piperidone thereto to prepare a compound (i). Then, the compound (i) is reacted with a compound (i-a) to prepare a compound (ii). The compound (ii) is subjected to urea and HCl treatment, followed by heating to prepare a compound (iii). Finally, the compound (iii) may be subjected to a uracil cyclization reaction in a mixed solvents of an aqueous NaOH and an alcohol to yield an intermediate compound (iv).

The compound of formula (I) in the present invention may be prepared according to the procedure shown in Reaction Scheme 2 using the compound (iv) prepared in the reaction above.

X: halide
PG: protecting group wherein,
R$_1$, R$_{3a}$, R$_{3b}$, R$_4$, R$_{5a}$, R$_{5b}$, R$_6$, R$_{7a}$, R$_{7b}$ and A have the same meanings as defined in formula (I).

As shown in Reaction Scheme 2, the compound (iv) may be treated with R$_6$—X and a base to yield the compound (v). And then, the compound (v) is treated with N-protected mesylate (compound (v-a)) and a base, followed by heating the mixture to obtain a compound (vi). The compound (vi) may be subjected to a deprotection for removing protecting group 1 ($PG_1$) therefrom to prepare a compound (vii), and the compound (vii) obtained is subjected to an alkylation or reductive amination using $R_4$-halide or $R_4$-aldehyde reagent to prepare a $R_4$-introduced compound (viii). Finally, the compound (viii) may be subjected to a deprotection to remove protecting group 2 ($PG_2$), to yield a compound (ix) (i.e., the compound of formula (I))

The compound (v) used as an intermediate in Reaction Scheme 2 above also can be prepared by the procedure shown in Reaction Scheme 3.

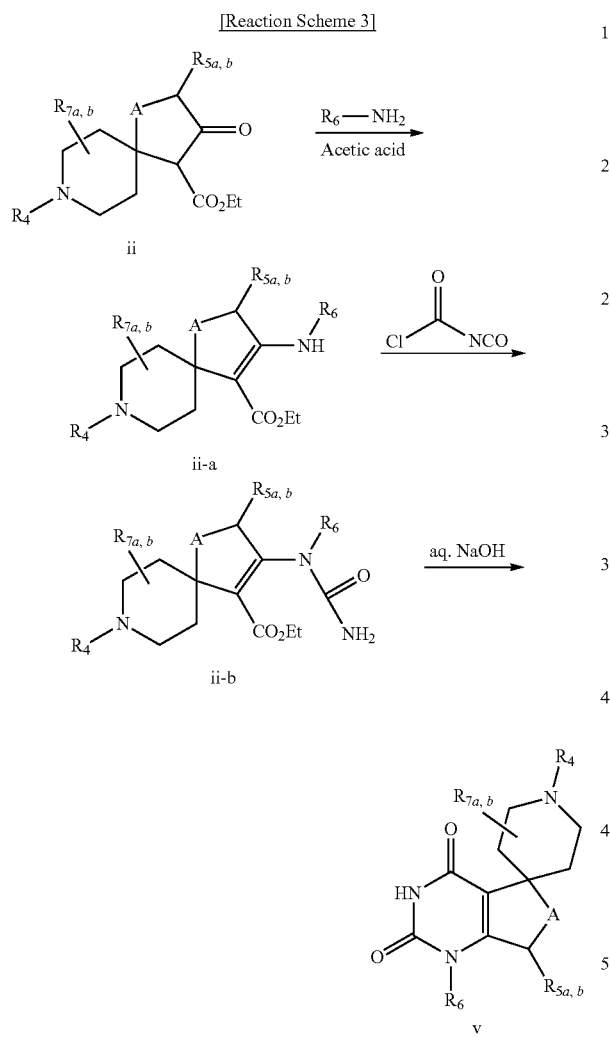

wherein, $R_4$, $R_{5a}$, $R_{5b}$, $R_6$, $R_{7a}$, $R_{7b}$ and A have the same meanings as defined in formula (I).

As shown in Reaction Scheme 3, the compound (ii) is heated in the presence of $R_6$-amine and an acid (e.g., an acetic acid) to yield an enamine compound (compound (iii-a)), followed by reacting with chlorocarbonylisocyanate to prepare a urea compound (compound (iii-b)). Then, the urea compound is reacted with an aqueous NaOH to obtain the urasil compound (v).

The compound (viii) used as an intermediate Reaction Scheme 2 above also can be prepared by the procedure shown in Reaction Scheme 4.

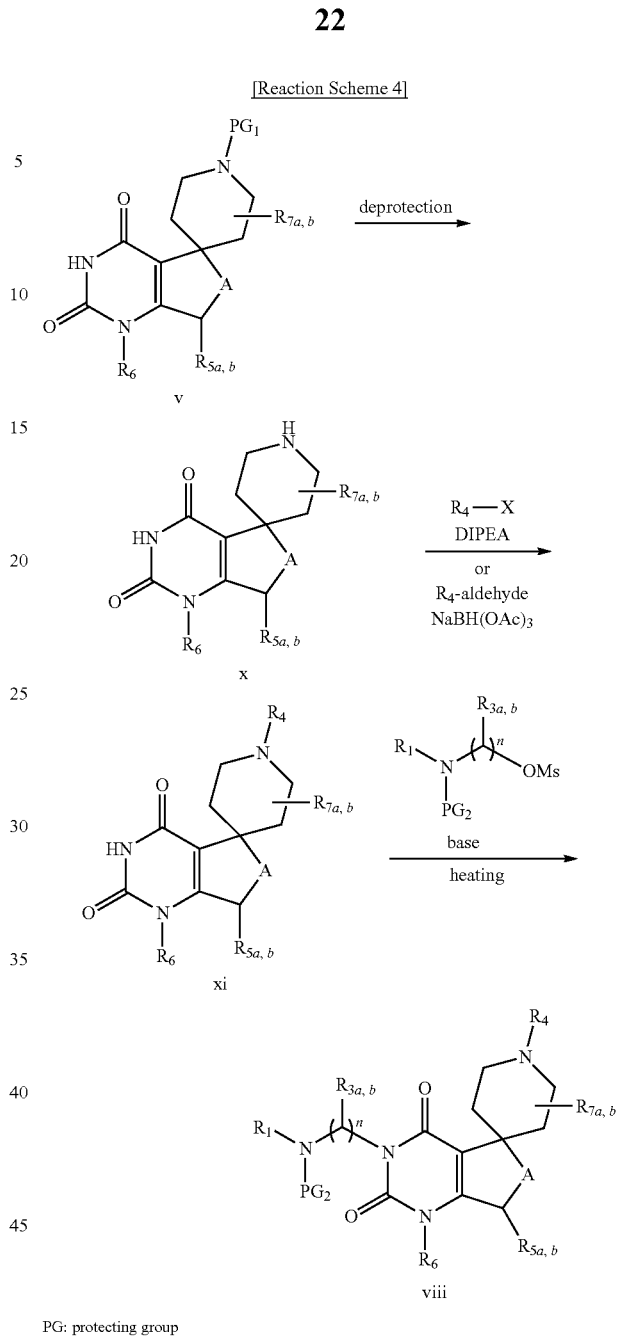

PG: protecting group wherein, $R_1$, $R_{3a}$, $R_{3b}$, $R_4$, $R_{5a}$, $R_{5b}$, $R_6$, $R_{7a}$, $R_{7b}$, n and A have the same meanings as defined in formula (I).

As shown in Reaction Scheme 4, the compound (x) prepared by deprotecting the compound (v) may be reacted with $R_4$-halide or $R_4$-aldehyde to introduce $R_6$ group thereto, and then the resulting compound (compound (xi)) is alkylated by heating in the presence of a suitable mesylate compound (compound (v-a)) and a base for alkylation to yield the compound (viii).

In addition, the compound of formula (I) in the present invention may be prepared according to the procedure shown in Reaction Scheme 5 using the compound (ix).

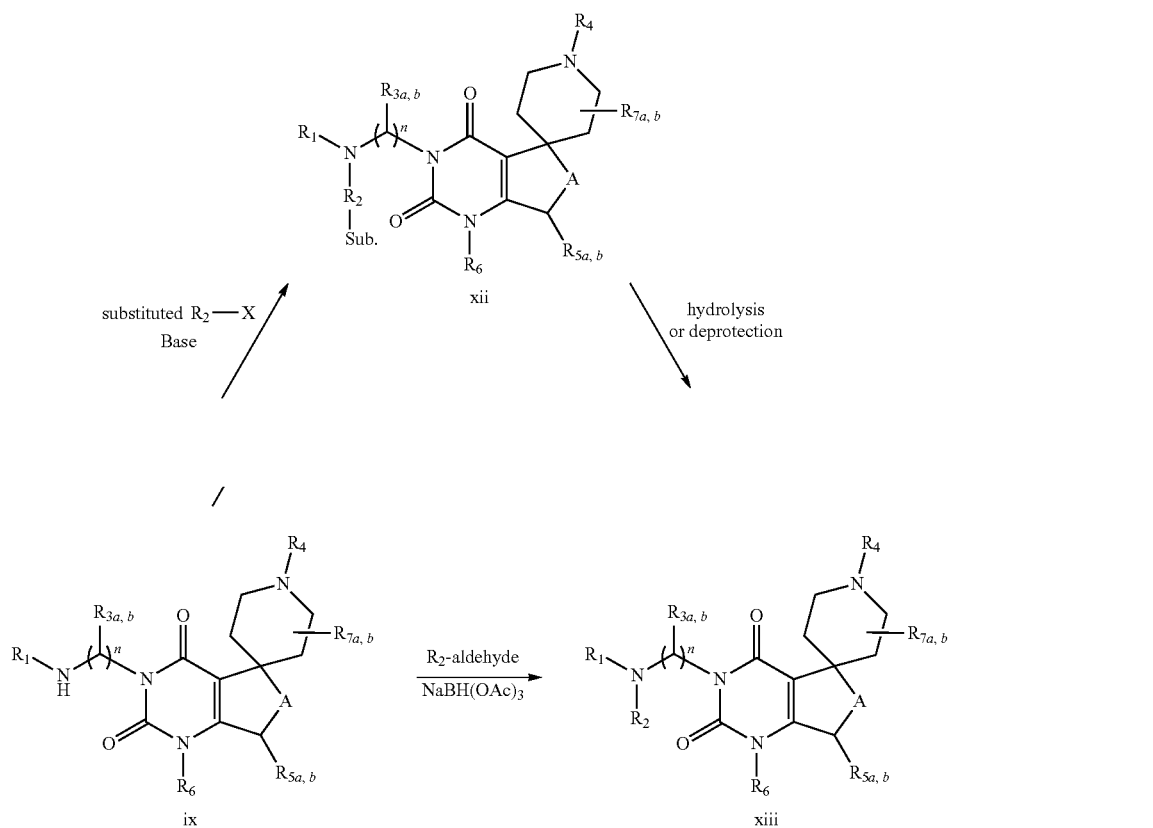

wherein, $R_1$, $R_2$, $R_{3a}$, $R_{3b}$, $R_4$, $R_{5a}$, $R_{5b}$, $R_6$, $R_{7a}$, $R_{7b}$, n and A have the same meanings as defined in formula (I).

As shown in Reaction Scheme 5, the compound (ix) may be subjected to an alkylation using an alkyl halide ($R_2$—X) in a presence of a base to prepare a compound (xii), followed by hydrolysis or deprotection thereof to yield a compound (xiii). Alternatively, the compound (ix) may be subjected to a reductive amination using $R_2$-aldehyde to obtain a compound (xiii).

Meanwhile, the compound of formula (I) wherein $R_{3a}$ is H and $R_{3b}$ is aromatic ring or substituted aromatic ring may be prepared according to the procedure shown in Reaction Scheme 6.

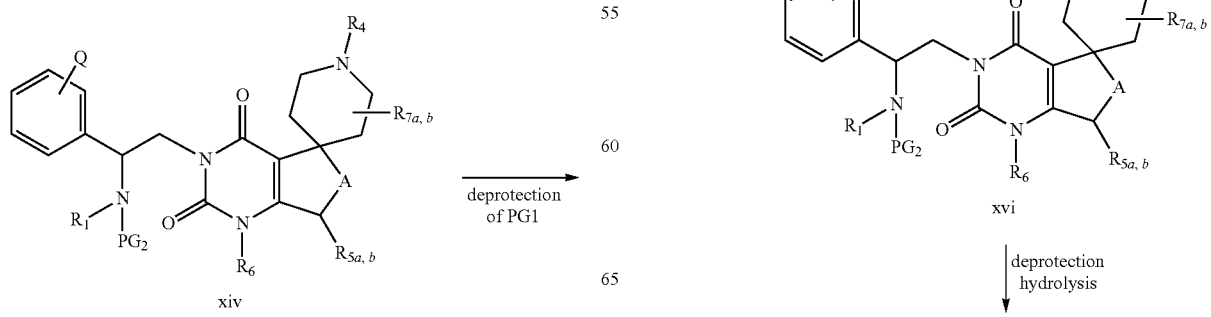

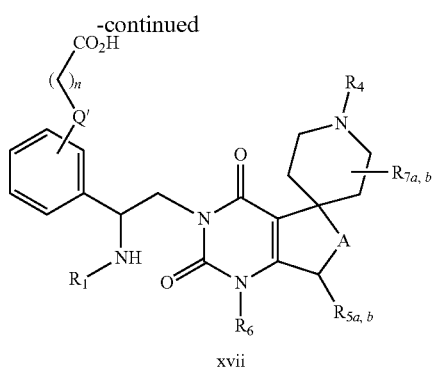

xvii

PG: protecting group
Q: —O—PG₁ or N—PG₁
Q': —O— or —NH— wherein, $R_1$, $R_4$, $R_{5a}$, $R_{5b}$, $R_6$, $R_{7a}$, $R_{7b}$, n and A have the same meanings as defined in formula (I).

As shown in Reaction Scheme 6, the compound (xiv) may be subjected to a deprotection for removing protecting group 1 ($PG_1$) therefrom to prepare a compound (xv), followed by an alkylation or reductive amination of the compound (xv) for introducing an acid-precursor ester thereto to prepare a compound (xvi). Finally, the compound (xvi) may be subjected to a deprotection and hydrolysis to yield a compound (xvii) (i.e., the compound of formula (I)).

Meanwhile, a compound (ii) as an intermediate for preparing the compound of formula (I) wherein A is $CH_2$, may be prepared according to the procedure shown in Reaction Scheme 7.

chloride, triethylamine (TEA) and ethyl potassium malonate to acetonitrile (ACN) is added to the obtained mixture to yield compound (xxi). The compound (xxi) thus obtained is treated with triethylamine and 4-acetamidobenzenesulfonyl azide to prepare compound (xxii), followed by reacting the compound (xxii) with rhodium (II) acetate dimer at room temperature to obtain the compound (ii).

The compound of formula (I) in the present invention may be used in the form of free acids or free bases. Alternatively, the inventive compounds may be in the form of acid- or base-addition salts. The acid-addition salts of the inventive compounds may be formed from organic or inorganic acids in accordance with the well-known methods in the art.

Examples of the suitable organic acids include maleic acid, fumaric acid, benzoic acid, ascorbic acid, succinic acid, methanesulfonic acid, acetic acid, trifluoroacetic acid, oxalic acid, propionic acid, tartaric acid, salicylic acid, citric acid, gluconic acid, lactic acid, mandelic acid, sinnamic acid, aspartic acid, stearic acid, palmitic acid, glycolic acid, glutamic acid and benzenesulfonic acid. Examples of the suitable inorganic acids include hydrochloric acid, hydrobromic acid, sulfuric acid, phosphoric acid and nitric acid. Examples of the base-addition salts include a salt formed with carboxylate anions; a salt formed with an organic and inorganic cations such as the cations selected from alkali metal and alkaline metal (e.g., lithium, sodium, potassium, magnesium, barium and calcium), ammonium ions and substituted derivatives thereof (e.g., dibenzyl ammonium, benzyl ammonium, 2-hydroxyethylammonium, etc.). Accordingly, the term "pharmaceutically acceptable salts" of formula (I) should be understood to contain all salt forms available in the art.

[Reaction Scheme 7]

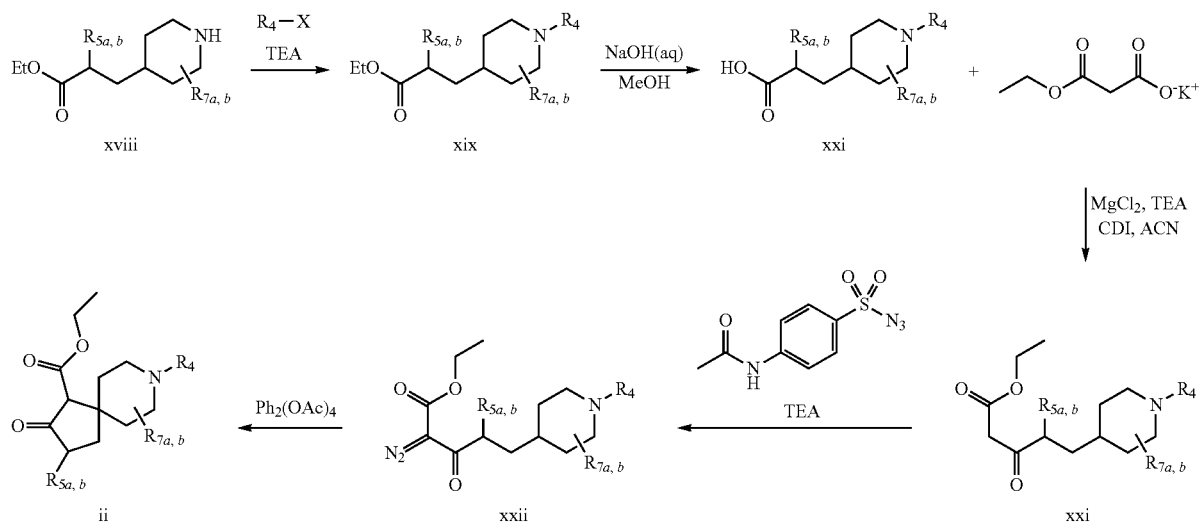

wherein, $R_4$, $R_{5a}$, $R_{5b}$, $R_{7a}$, $R_{7b}$ and A have the same meanings as defined in formula (I).

As shown in Reaction Scheme 7, for example, the compound (xviii) may be alkylated for introducing $R_4$ thereto to prepare a compound (xix), followed by a hydrolysis thereof to yield a compound (xx). The compound (xx) may is added to 1,1'-carbonylimidazol (CDI) and stirred to prepare a mixture, and a solution prepared by adding magnesium Also, a prodrug is comprised within the scope of the present invention. The prodrug refers to all carrier covalently connected, which is capable of being releasing the compound of formula (I) in vivo by the cleavage of a covalent bond once administered to patients. Typically, the prodrugs are prepared by modifying functional groups, and this modification can be cancelled by conventional operation or by metabolism in vivo to produce active compounds. For example, the prodrug comprises the compounds bonded to a group for forming the hydroxyl, amine or sulfhydryl group by cleavage when administered to the patients. Representative examples of the present invention include, but not limited thereto acetate, formate and benzoate derivatives for the alcohol and amine functional groups of the compound of formula (I). In addition, in case of carboxylic acid (—COOH), the prodrugs may comprise in the form of esters such as methyl ester, ethyl ester and the like.

The present invention pertains to stereoisomers of the compounds of formula (I). The compounds of formula (I) may have a chiral center and thus exist as enantiomers or diastereomers or in the form of racemates or racemic mixtures, which all fall within the scope of the present invention. Moreover, the compound of formula (I) may have axial chirality, thus taking the form of atropisomers. Further, some of the crystals of the compounds may exhibit polymorphs, which are also within the scope of the present invention. Furthermore, the compound of formula (I) may form solvates with water or any organic solvents, all of which fall within the scope of the present invention as well.

Also, the present invention provides pharmaceutical composition for preventing or treating a sex hormone-related disease comprising the compound of formula (I), or a stereoisomer, a prodrug or a pharmaceutically acceptable salt thereof as an active ingredient. The pharmaceutical composition may further comprise a pharmaceutically acceptable carrier or a vehicle.

The sex hormone-related disease is selected from the group consisting of endometriosis, amenorrhea, irregular menstruation, uterine myoma, uterine fibroids, polycystic ovarian disease, lupus erythematous, hypertrichosis, precocious puberty, short stature, acne, alopecia, gonadal steroid-dependent neoplasms (e.g., prostate cancer, breast cancer, ovarian cancer, uterine cancer, pituitary cancer, etc.), gonadotropin-producing pituitary adenoma, sleep apnea, irritable bowel syndrome, premenstrual syndrome, benign prostatic hyperplasia, contraception and infertility (e.g., assisted reproductive techniques such as in vitro fertilization), and Alzheimer disease.

A daily dose of the inventive compound should be determined in light of various relevant factors including the subject to be treated, the severity of the disease or condition, the administration rate, the judgement of the doctor and the like. The inventive compound as an active ingredient may be administrated to a mammal including human in the range of 0.01 to 100 mg/kg (body weight), preferably 0.2 to 50 mg/kg (body weight), 1 to 2 times daily or on/off schedule by oral or parenteral administration.

The pharmaceutical composition of the present invention may be formulated in accordance with conventional methods, and may be prepared in the form of oral formulations such as tablets, pills, powders, capsules, syrups, emulsions, microemulsions, and others, or parenteral formulations such as intramuscular, intravenous, or subcutaneous administrations.

Examples of carriers for oral formulations may include cellulose, calcium silicate, corn starch, lactose, sucrose, dextrose, calcium phosphate, stearic acid, magnesium stearate, calcium stearate, gelatin, talc, surfactants, suspending agents, emulsifiers, diluents and others. Examples of carriers for injectable formulations may include water, saline, glucose solution, glucose solution analogs, alcohols, glycols, ether (e.g., polyethylene glycol 400), oils, fatty acids, fatty acid esters, glycerides, surfactants, suspending agents, emulsifiers, and others.

Also, the present invention provides a method of preventing or treating a sex hormone-related disease in a subject comprising administering to the subject in need thereof an effective amount of formula (I), a stereoisomer, a prodrug, or a pharmaceutically acceptable salt thereof.

In addition, the present invention provides a method for preparing the compound of formula (I), a stereoisomer, a prodrug, or a pharmaceutically acceptable salt thereof for use in prophylactic or therapeutic treatment of sex hormone-related disease.

Hereinafter, the present invention is described more specifically by the following Examples, but these are provided for illustration purposes only, and the present invention is not limited thereto.

Example 1

Synthesis of (R)-3-(2-amino-2-phenylethyl)-1-(2-fluoro-6-(trifluoromethyl)benzyl)-1'-(3-fluorobenzyl)-1H-spiro[furo[3,4-d]pyrimidin-5,4'-piperidine]-2,4(3H,7H)-dione

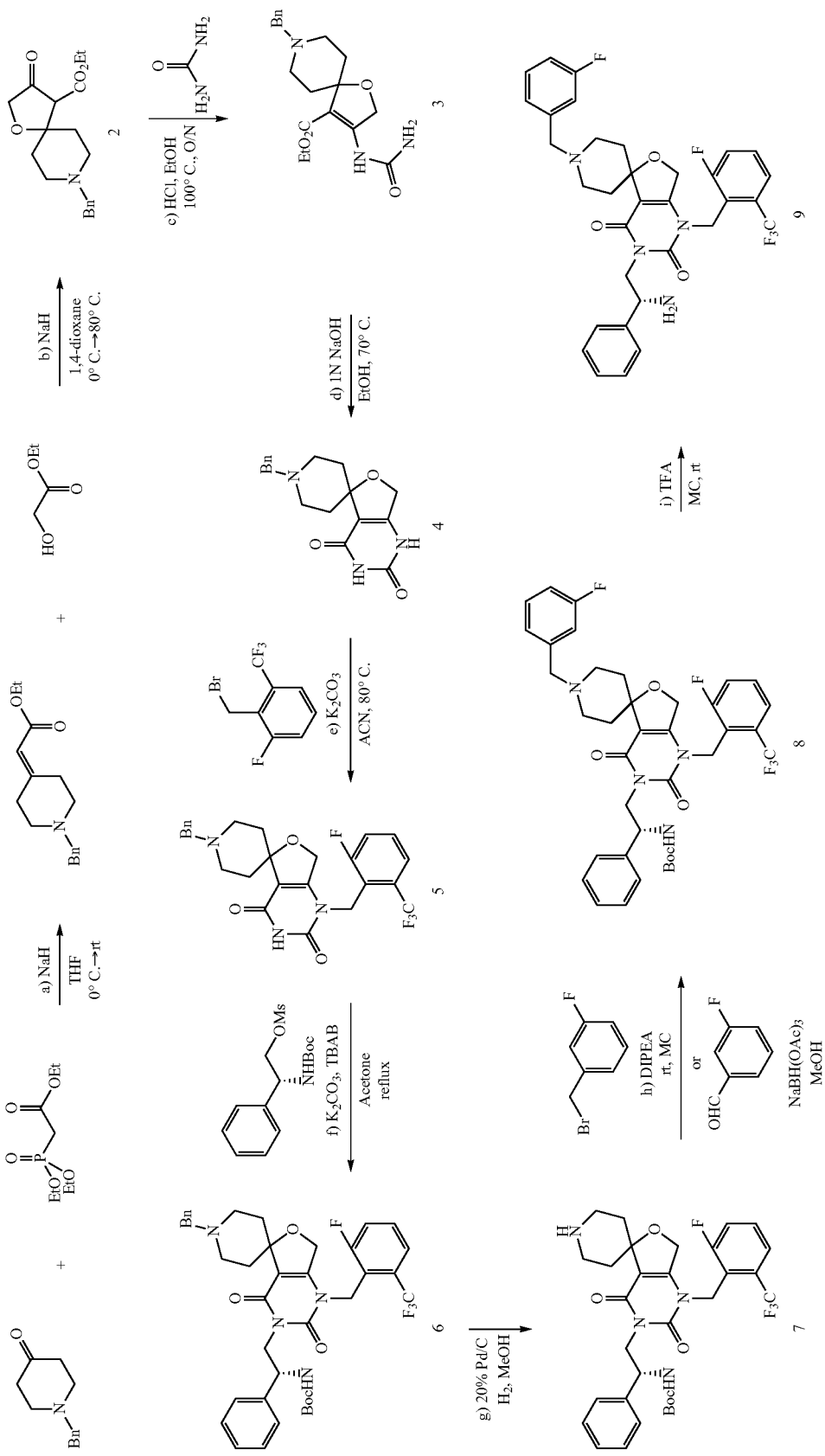

Step A. Preparation of ethyl 2-(1-benzylpiperidine-4-ylidene)acetate (1)

Sodium hydride (60% dispersion in mineral oil) (2.53 g, 634 mmol) was added to anhydrous tetrahydrofuran (80 mL) and the resulting mixture was stirred for 10 min in an ice bath. Then, triethyl phosphonoacetate (12.6 mL, 63.4 mmol) was slowly added thereto at the same temperature. The resulting solution was stirred for 30 min at room temperature, and cooled in an ice bath, followed by adding a solution prepared by diluting 1-benzyl-4-piperidone (10.5 g, 52.8 mmol) in anhydrous tetrahydrofuran (20 mL) thereto. The resulting solution was stirred for 30 min at room temperature under a nitrogen atmosphere. The reaction solution was cooled in an ice bath and added with a saturated aqueous ammonium chloride solution to complete the reaction. The aqueous layer was extracted twice with ethyl acetate. The organic layer was separated, dried over $MgSO_4$, filtered, and concentrated under reduced pressure. The concentrate was purified by silica gel chromatography (eluent: hexane/ethyl acetate=5/1~3/1), and dried under vacuum to yield the title compound as clear liquid (13.5 g, yield: 98%).

$^1$H NMR (600 MHz, $CDCl_3$) δ 1.26 (3H, td), 2.31 (2H, m), 2.51 (4H, m), 2.98 (2H, m), 3.51 (2H, s), 4.13 (2H, q), 5.63 (1H, s), 7.25 (1H, m), 7.29-7.33 (4H, m)

Step B. Preparation of ethyl 8-benzyl-3-oxo-1-oxa-8-azaspiro[4.5]decane-4-carboxylate (2)

Sodium hydride (60% dispersion in mineral oil) (27.8 g, 0.694 mol) was added to 1,4-dioxane (800 mL) and the resulting mixture was stirred for 10 min in an ice bath. Then, ethyl glycolate (72.3 g, 0.694 mol) was slowly added thereto at the same temperature. The resulting solution was stirred for 2 hrs at room temperature, and ethyl 2-(1-benzylpiperidine-4-ylidene)acetate (1) (120 g, 0.463 mol) prepared in Step A was slowly added thereto. The resulting solution was heated and stirred at 80° C. for 15 hrs. Subsequently, the reaction solution was cooled in an ice bath and added with a saturated aqueous ammonium chloride solution (200 mL) to complete the reaction. A saturated aqueous sodium chloride solution (500 mL) was added to the mixture, and 1,4-dioxane was removed under reduced pressure. The aqueous layer was extracted four times with ethyl acetate. The organic layer was separated, dried over MgSO4 and concentrated under reduced pressure. The concentrate was purified by silica gel chromatography (eluent: hexane/ethyl acetate=3/1~0/1), and dried under vacuum to yield the title compound as bright yellow liquid (94.0 g, yield: 64%).

$^1$H NMR (600 MHz, DMSO-$d_6$) δ 1.12 (3H, t), 2.10 (2H, td), 2.21 (2H, td), 2.53-2.55 (2H, m), 3.40 (2H, d), 3.91 (2H, s), 4.00 (2H, q), 4.06 (1H, q), 7.18-7.21 (1H, m), 7.24-7.29 (4H, m).

Step C. Preparation of ethyl 8-benzyl-3-ureido-1-oxa-8-azaspiro[4.5]dec-3-en-4-carboxylate (3)

Ethyl 8-benzyl-3-oxo-1-oxa-8-azaspiro[4.5]decane-4-carboxylate (2) (145 g 0.457 mol) obtained in Step B and urea (274 g, 4.57 mol) were added to ethyl alcohol (457 mL), and concentrated HCl (190 mL, 2.29 mol) was slowly added thereto at room temperature. The resulting solution was heated and stirred at 100° C. for 15 hrs, cooled down to 0° C., and slowly added with a 10 N NaOH aqueous solution (229 mL, 2.29 mol). The resulting solution was stirred for 30 min at room temperature and left alone for 20 min. A solid thus obtained was filtered and washed with ethyl alcohol (2000 mL) to obtain the title compound as white solid (110 g, yield: 67%).

$^1$H NMR (600 MHz, DMSO-$d_6$) δ 1.22 (3H, t), 1.36 (2H, d), 2.12 (2H, m), 2.18 (2H, m), 2.58 (2H, m), 3.42 (2H, s), 4.17 (2H, q), 4.91 (2H, s), 5.39 (1H, s), 7.19-7.21 (1H, m), 7.24-7.29 (4H, m), 9.35 (1H, s)

Step D. Preparation of 1'-benzyl-1H-spiro[furo[3,4-d]pyrimidin-5,4'-piperidine]-2,4(3H,7H)-dione (4)

Ethyl 8-benzyl-3-ureido-1-oxa-8-azaspiro[4.5]dec-3-en-4-carboxylate (3) (129 g, 0.359 mol) obtained in Step C was added to ethyl alcohol (850 mL) and a 5 N NaOH aqueous solution (71.8 mL, 0.359 mol) was slowly added thereto at room temperature. The resulting solution was heated and stirred at 70° C., stirred for 1 hr, cooled down to 0° C., and slowly added with concentrated HCl (30.0 mL, 0.359 mol). The resulting solution was stirred for 30 min at room temperature and left alone for 20 min. A solid thus obtained was filtered and washed with ethyl alcohol (500 mL) and acetonitrile (500 mL) to obtain the title compound as white solid (111 g, yield: 99%).

$^1$H NMR (300 MHz, DMSO-$d_6$) δ 1.50 (2H, d), 2.00-2.20 (4H, m), 2.65 (2H, m), 3.46 (2H, s), 4.65 (2H, s), 7.23 (1H, m), 7.30 (4H, m), 10.95 (1H, s), 11.25 (1H, s)

Step E. Preparation of 1'-benzyl-1-(2-fluoro-6-(trifluoromethyl)benzyl)-1H-spiro[furo[3,4-d]pyrimidin-5,4'-piperidine]2,4(3H,7H)-dione (5)

1'-benzyl-1H-spiro[furo[3,4-d]pyrimidin-5,4'-piperidine]-2,4(3H,7H)-dione (4) (130 g, 0.416 mol) obtained in Step D and potassium carbonate (114 g, 0.832 mol) were suspended in 1-methyl-2-pyrrolidinone (325 mL), and 2-fluoro-6-(trifluoromethyl)benzylbromide (107 g, 0.416 mol) was slowly added thereto. The resulting mixture was stirred for 2 hrs, and added with ethyl acetate (1300 mL) and deionized water (1300 mL). The organic layer was separated and the aqueous layer was further extracted once with ethyl acetate (650 mL). The organic layer was washed once with a saturated aqueous solution of sodium chloride (2000 mL), dried over $Na_2SO_4$, filtered, and concentrated under reduced pressure. Methyl tert butyl ether (MTBE, 300 mL) was added to the resulting solid from the concentration process, stirred for 2 hrs, followed by filteration. The filted solid was washed with MTBE (200 mL) to obtain the title compound as white solid (92.7 g, yield: 46%).

$^1$H NMR (600 MHz, $CDCl_3$) δ 1.56 (2H, d), 2.25 (2H, m), 2.35 (2H, m), 2.75 (2H, m), 3.50 (2H, s), 4.66 (2H, s), 5.12 (2H, s), 7.21-7.24 (1H, m), 7.27-7.30 (3H, m), 7.33-7.34 (2H, m), 7.47 (1H, m), 7.54 (1H, d), 8.11 (1H, s)

Step F. Preparation of (R)-tert-butyl (2-(1'-benzyl-1-(2-fluoro-6-(trifluoromethyl)benzyl)-2,4-dioxo-1H-spiro[furo[3,4-d]pyrimidine-5,4'-piperidin]-3 (2H,4H,7H)-yl)-1-phenylethyl)carbamate (6)

1'-benzyl-1-(2-fluoro-6-(trifluoromethyl)benzyl)-1H-spiro[furo[3,4-d]pyrimidine-5,4'-piperidine]2,4(3H,7H)-dione (5) (9.40 g, 19.2 mmol) obtained in Step E, (R)-2-((tert-butoxycarbonyl)amino)-2-phenylethyl methanesulfonate (12.1 g, 38.4 mmol), potassium carbonate (8.00 g, 57.6 mmol) and tetrabutylammonium bromide (620 mg, 1.92 mmol) were suspended in acetone (250 mL), and heated to 70° C., followed by stirring for 15 hrs. The reaction solution was cooled down to room temperature, and filtered to remove solid. Acetone was removed from the filtrate under reduced pressure, and the solution was diluted with ethyl acetate (200 mL). The resulting solution was washed twice with a saturated sodium bicarbonate solution (200 mL), dried over MgSO$_4$, and concentrated under reduced pressure. The residue was purified by silica gel chromatography (eluent: hexane/ethyl acetate=9/1~1/1), and dried under vacuum to obtain the title compound as ivory foam (11.8 g, yield: 87%).

$^1$H NMR (600 MHz, CDCl$_3$) δ 1.35 (9H, s), 1.54 (2H, m), 2.25-2.30 (2H, m), 2.40 (2H, m), 2.77 (2H, m), 4.02 (1H, d), 4.27 (1H, t), 4.71 (2H, m), 5.01 (1H, m), 5.05 (1H, d), 5.24 (1H, d), 5.64 (1H, d), 7.21-7.37 (11H, m), 7.46 (1H, m), 7.55 (1H, d).

Step G. Preparation of (R)-tert-butyl (2-(1-(2-fluoro-6-(trifluoromethyl)benzyl)-2,4-dioxo-1H-spiro[furo[3,4-d]pyrimidine-5,4'-piperidin]-3(2H,4H,7H)-yl)-1-phenylethyl)carbamate (7)

(R)-tert-butyl (2-(1'-benzyl-1-(2-fluoro-6-(trifluoromethyl)benzyl)-2,4-dioxo-1H-spiro[furo[3,4-d]pyrimidine-5,4'-piperidin]-3(2H,4H,7H)-yl)-1-phenylethyl)carbamate (6) (11.8 g, 16.6 mmol) obtained in Step F was dissolved in methanol (250 mL), added with Pd/C (2.40 g, 20% w/w), and the mixture was filled with hydrogen gas and stirred for 15 hrs. The resulting mixture was filtered using a Celite pad. The filtrate was concentrated under reduced pressure, dried under vacuum to obtain the title compound as ivory foam (7.70 g, yield: 75%).

Step H. Preparation of (R)-tert-butyl (2-(1-(2-fluoro-6-(trifluoromethyl)benzyl)-1'-(3-fluorobenzyl)-2,4-dioxo-1H-spiro[furo[3,4-d]pyrimidine-5,4'-piperidin]-3(2H,4H,7H)-yl)-1-phenylethyl)carbamate (8)

(R)-tert-butyl (2-(1-(2-fluoro-6-(trifluoromethyl)benzyl)-2,4-dioxo-1H-spiro[furo[3,4-d]pyrimidine-5,4'-piperidin]-3(2H,4H,7H)-yl)-1-phenylethyl)carbamate (7) (30 mg, 0.0485 mmol) obtained in Step G was added to dichloromethane solution (2 mL), together with 3-fluorobenzyl bromide (9 L, 0.0727 mmol) and N,N-diisopropylethylamine (17 L, 0.0970 mmol), followed by stirring for 15 hrs at room temperature. The reaction solution was concentrated, and purified by MPLC (ethyl acetate/hexane=1/4~1/1) to obtain the title compound as colorless oil (31 mg, yield: 88%).

$^1$H NMR (300 MHz, CDCl$_3$) δ 7.58-7.22 (m, 9H), 7.09-7.14 (m, 2H), 6.92 (m, 1H), 5.64 (d, 1H), 5.29-4.99 (m, 3H), 4.72 (m, 2H), 4.28 (m, 1H), 4.03 (m, 1H), 3.52 (s, 2H), 2.76 (m, 2H), 2.26-2.47 (m, 4H), 1.57 (t, 2H), 1.36 (s, 9H)

Step I. Preparation of (R)-3-(2-amino-2-phenylethyl)-1-(2-fluoro-6-(trifluoromethyl)benzyl)-1'-(3-fluorobenzyl)-1H-spiro[furo[3,4-d]pyrimidin-5,4'-piperidine]-2,4(3H,7H)-dione (9)

(R)-tert-butyl (2-(1-(2-fluoro-6-(trifluoromethyl)benzyl)-1'-(3-fluorobenzyl)-2,4-dioxo-1H-spiro[furo[3,4-d]pyrimidin-5,4'-piperidine]-3(2H,4H,7H)-yl)-1-phenylethyl)carbamate (8) (31 mg, 0.0427 mmol) obtained in Step H was added to dichloromethane (2 mL) and trifluoroacetic acid (0.1 mL), and the mixture was stirred for 2.5 hrs at room temperature. The reaction solution was neutralized with a saturated NaHCO$_3$(aq) and extracted with dichloromethane. The organic layer was dried over MgSO$_4$, concentrated, and purified by MPLC (methanol/dichloromethane=0/100~1/9) to obtain the title compound as white amorphous solid (21 mg, yield: 79%).

$^1$H NMR (300 MHz, CDCl$_3$) δ 7.57-7.08 (m, 11H), 6.92 (m, 1H), 5.15 (d, 2H), 4.70 (s, 2H), 4.35 (m, 1H), 4.19 (m, 1H), 4.05 (m, 1H), 3.51 (s, 2H), 2.74 (m, 2H), 2.25-2.46 (m, 4H), 1.55 (m, 2H); MS (ESI) m/z 627.8 (MH$^+$)

Meanwhile, 1'-benzyl-1-(2-fluoro-6-(trifluoromethyl)benzyl)-1H-spiro[furo[3,4-d]pyrimidine-5,4'-piperidine]-2,4 (3H,7H)-dione (5) as an intermediate may be prepared by the following steps.

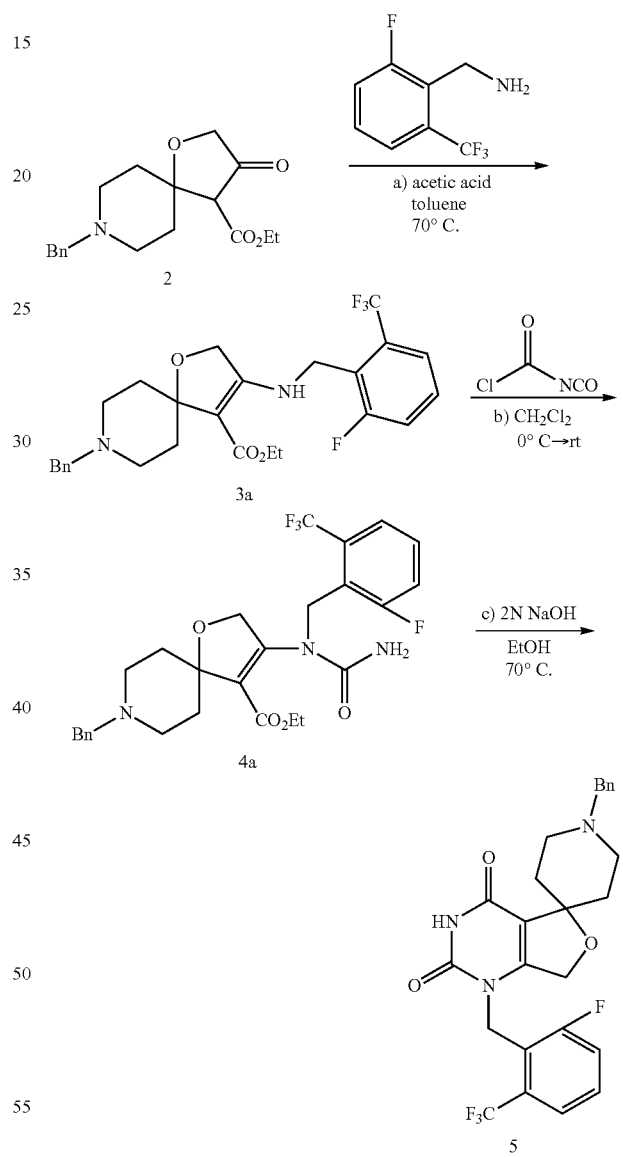

Step A. Preparation of Ethyl 8-benzyl-3-((2-fluoro-6-(trifluoromethyl)benzyl)amino)-1-oxa-8-azaspiro[4.5]dec-3-en-4-carboxylate (3a)

Ethyl 8-benzyl-3-oxo-1-oxa-8-azaspiro[4.5]decane-4-carboxylate (2) (560 mg, 1.76 mmol) and (2-fluoro-6-(trifluoromethyl)phenyl)methanamine (375 mg, 1.94 mmol) were dissolved in toluene (1 mL), added with acetic acid (111 μL, 1.94 mmol), and stirred for 12 hrs at 70° C. The resulting solution was cooled down to room temperature, diluted with dichloromethane, and washed with a saturated aqueous sodium bicarbonate solution. The aqueous layer was further extracted once with dichloromethane, and the organic layer was collected and concentrated under reduced pressure. The residue was purified by silica gel chromatography (eluent: hexane/ethyl acetate=2/1), and dried under vacuum to obtain the title compound as ivory oil (864 mg, yield: 99%).

$^1$H NMR (300 MHz, CDCl$_3$) δ 1.26 (3H, t), 1.48 (2H, m), 2.31 (4H, m), 2.73 (2H, m), 3.53 (2H, s), 4.16 (2H, q), 4.41 (2H, d), 4.81 (2H, s), 7.21-7.35 (5H, m), 7.42-7.49 (3H, m)

Step B. Ethyl 8-benzyl-3-(1-(2-fluoro-6-(trifluoromethyl)benzyl)ureido)-1-oxa-8-azaspiro[4.5]dec-3-en-4-carboxylate (4a)

Ethyl 8-benzyl-3-((2-fluoro-6-(trifluoromethyl)benzyl)amino)-1-oxa-8-azaspiro[4.5]dec-3-en-4-carboxylate (3a) (6.5 g, 0.013 mol) was dissolved in dichloromethane (60 mL), cooled down to 0° C., and slowly added with N-chlorocarbonyl isocyanate (1.8 mL, 0.021 mol) under a nitrogen atmosphere, followed by stirring for 2 hrs at room temperature. The reaction solution was cooled down to 0° C., further added with N-chlorocarbonyl isocynate (1.0 mL, 0.012 mol), and stirred for 2 hrs at room temperature. The reaction solution was cooled down to 0° C. again, slowly added with a saturated aqueous sodium bicarbonate solution, and the organic layer was separated therefrom. The aqueous layer was further extracted once with dichloromethane, and the organic layer was collected and concentrated under reduced pressure. The residue was purified by silica gel chromatography (eluent: dichloromethane/methanol=98/2~95/5), and dried under vacuum to obtain the title compound as yellow foam (2.6 g, yield: 37%).

$^1$H NMR (300 MHz, CDCl$_3$) δ 1.18 (3H, t), 1.70-1.76 (2H, m), 2.05-2.10 (1H, m), 2.18-2.27 (3H, m), 2.65 (1H, m), 2.73 (1H, m), 3.43-3.49 (2H, m), 4.03-4.19 (2H, m), 4.76 (1H, d), 5.52 (1H, d), 6.26 (1H, s), 7.20-7.30 (6H, m), 7.45 (1H, m), 7.53 (1H, m), 7.73 (1H, s)

Step C. Preparation of 1'-benzyl-1-(2-fluoro-6-(trifluoromethyl)benzyl)-1H-spiro[furo[3,4-d]pyrimidin-5,4'-piperidine]-2,4(3H,7H)-dione (5)

Ethyl 8-benzyl-3-(1-(2-fluoro-6-(trifluoromethyl)benzyl)ureido)-1-oxa-8-azaspiro[4.5]dec-3-en-4-carboxylate (4a) (2.6 g, 4.86 mmol) was dissolved in ethanol (60 mL), and an aqueous solution of 1N NaOH (48 mL, 48.6 mmol) was added thereto, followed by stirring for 12 hrs at 70° C. The reaction solution was concentrated, diluted with dichloromethane, and neutralized by adding an aqueous solution of 1N HCl. The organic layer was separated, and the aqueous layer was extracted twice with dichloromethane. The organic layer was collected and dried over Na$_2$SO$_4$, filtered, and concentrated under reduced pressure. The concentrate was purified by silica gel chromatography (eluent: dichloromethane/methanol=97/3~90/10), and dried under vacuum to obtain the title compound as ivory solid (1.67 g, yield: 70%).

$^1$H NMR (300 MHz, DMSO-d$_6$) δ 1.50 (2H, d), 2.17 (4H, m), 2.67 (2H, m), 3.46 (2H, s), 4.83 (2H, s), 4.98 (2H, s), 7.24 (1H, m), 7.32 (4H, m), 7.60 (3H, m), 11.29 (1H, s)

Examples 1-1 to 1-75

The compounds of Examples 1-1 to 1-75 were prepared in the same manner as described in Example 1 above, except for using R$_4$-halide or aldehyde reagent for introducing the corresponding R$_4$ group shown in Table 1 below instead of 3-fluorobenzyl bromide in Step H of Example 1.

TABLE 1

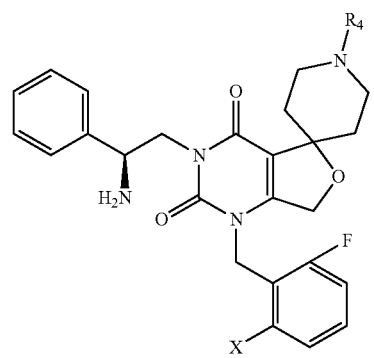

| Example | —R$_4$ | X | M.W. | Mass |
|---|---|---|---|---|
| 1-1 | Me | CF$_3$ | 532.5 | 533.8 |
| 1-2 | OMe | CF$_3$ | 576.5 | 577.7 |
| 1-3 | t-Bu | CF$_3$ | 588.6 | 589.9 |
| 1-4 | N-methylpyrrolidinyl | CF$_3$ | 629.6 | 630.7 |
| 1-5 | 2-pyridylmethyl | CF$_3$ | 609.6 | 610.8 |
| 1-6 | 3-pyridylmethyl | CF$_3$ | 609.6 | 610.8 |
| 1-7 | 4-pyridylmethyl | CF$_3$ | 609.6 | 610.7 |
| 1-8 | fluoropyridyl | CF$_3$ | 627.6 | 628.7 |

TABLE 1-continued
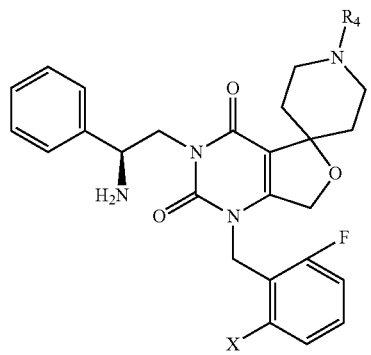
| Example | —R4 | X | M.W. | Mass |
|---|---|---|---|---|
| 1-9 | 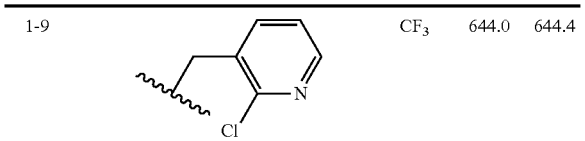 | CF3 | 644.0 | 644.4 |
| 1-10 | 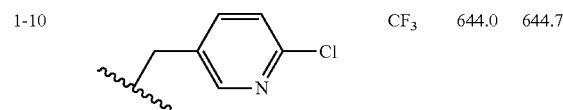 | CF3 | 644.0 | 644.7 |
| 1-11 | 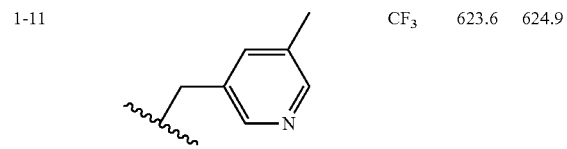 | CF3 | 623.6 | 624.9 |
| 1-12 | 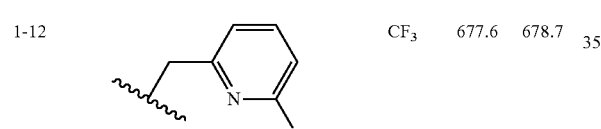 | CF3 | 677.6 | 678.7 |
| 1-13 | 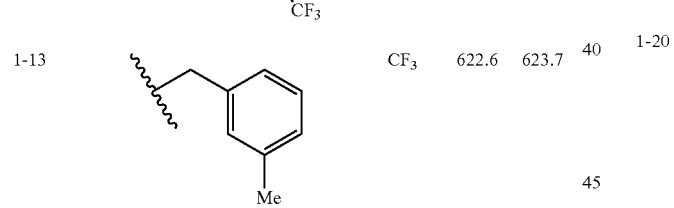 | CF3 | 622.6 | 623.7 |
| 1-14 | 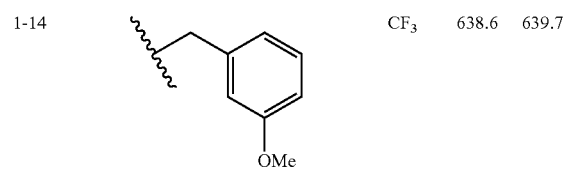 | CF3 | 638.6 | 639.7 |
| 1-15 | 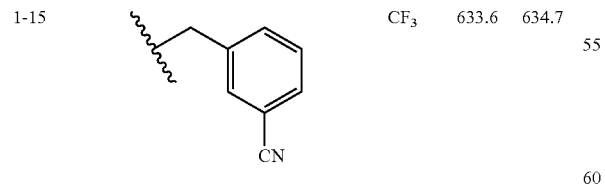 | CF3 | 633.6 | 634.7 |
| 1-16 | 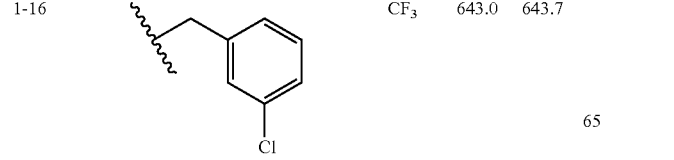 | CF3 | 643.0 | 643.7 |
TABLE 1-continued
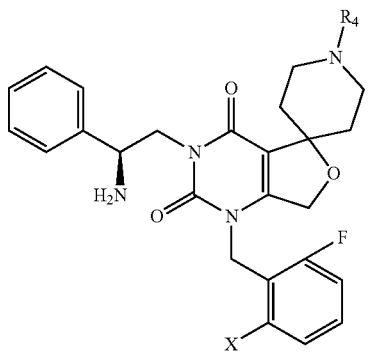
| Example | —R4 | X | M.W. | Mass |
|---|---|---|---|---|
| 1-17 | 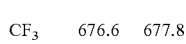 | CF3 | 676.6 | 677.8 |
| 1-18 |  | CF3 | 692.6 | 693.7 |
| 1-19 |  | CF3 | 666.6 | 667.8 |
| 1-20 | 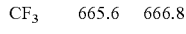 | CF3 | 665.6 | 666.8 |
| 1-21 | 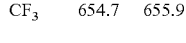 | CF3 | 654.7 | 655.9 |
| 1-22 | 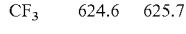 | CF3 | 624.6 | 625.7 |
| 1-23 |  | CF3 | 686.7 | 687.7 |

TABLE 1-continued

| Example | —R4 | X | M.W. | Mass |
|---|---|---|---|---|
| 1-24 | 7-benzothiophenylmethyl | CF₃ | 664.7 | 665.7 |
| 1-25 | 4-benzofurazanylmethyl | CF₃ | 650.6 | 651.8 |
| 1-26 | 2-methylbenzyl | CF₃ | 622.6 | 622.6 |
| 1-27 | 2-methoxybenzyl | CF₃ | 638.6 | 638.8 |
| 1-28 | 2-hydroxybenzyl | CF₃ | 624.6 | 624.0 |
| 1-29 | 2-fluorobenzyl | CF₃ | 626.6 | 626.7 |
| 1-30 | 2-cyanobenzyl | CF₃ | 633.6 | 633.8 |
| 1-31 | 2,3-difluorobenzyl | CF₃ | 644.6 | 644.6 |
| 1-32 | 2-trifluoromethylbenzyl | CF₃ | 676.6 | 676.7 |
| 1-33 | 2-cyano-3-fluorobenzyl | CF₃ | 651.6 | 651.9 |
| 1-34 | 2-fluoro-3-cyanobenzyl | CF₃ | 651.6 | 651.8 |
| 1-35 | 3-trifluoromethylbenzyl | F | 626.6 | 627.1 |
| 1-36 | 2-trifluoromethoxybenzyl | CF₃ | 692.6 | 692.5 |
| 1-37 | 2-(methoxycarbonyl)benzyl | CF₃ | 666.6 | 666.6 |
| 1-38 | 2-chlorobenzyl | CF₃ | 643.0 | 642.8 |

TABLE 1-continued

| Example | —R₄ | X | M.W. | Mass |
|---|---|---|---|---|
| 1-39 | 3-methoxy-2-fluorobenzyl | CF₃ | 656.6 | 656.5 |
| 1-40 | 5-(aminocarbonyl)furan-2-ylmethyl | CF₃ | 641.6 | 641.9 |
| 1-41 | 5-(methylaminocarbonyl)furan-2-ylmethyl | CF₃ | 655.6 | 655.8 |
| 1-42 | 5-(trifluoromethyl)furan-2-ylmethyl | F | 616.5 | 617.6 |
| 1-43 | 3-chlorobenzyl | F | 593.0 | 594.1 |
| 1-44 | 3-cyanobenzyl | F | 583.6 | 584.7 |
| 1-45 | 2-phenylethyl | CF₃ | 622.6 | 623.7 |
| 1-46 | furan-2-ylmethyl | CF₃ | 598.5 | 599.8 |
| 1-47 | 5-methylfuran-2-ylmethyl | CF₃ | 612.6 | 613.7 |
| 1-48 | 5-chlorofuran-2-ylmethyl | CF₃ | 633.0 | 633.7 |
| 1-49 | (6-hydroxypyridin-3-yl)methyl | CF₃ | 625.6 | 626.8 |
| 1-50 | 4-methylbenzyl | CF₃ | 622.6 | 623.9 |
| 1-51 | 4-chlorobenzyl | CF₃ | 643.0 | 643.9 |
| 1-52 | 4-cyanobenzyl | CF₃ | 633.6 | 634.9 |
| 1-53 | 4-(trifluoromethyl)benzyl | CF₃ | 676.6 | 677.8 |
| 1-54 | 4-(methoxycarbonyl)benzyl | CF₃ | 666.6 | 667.9 |

TABLE 1-continued

| Example | —R₄ | X | M.W. | Mass |
|---|---|---|---|---|
| 1-55 | 4-fluorobenzyl | CF₃ | 626.62 | 627.9 |
| 1-56 | 4-hydroxybenzyl | CF₃ | 624.6 | 625.9 |
| 1-57 | 4-methoxybenzyl | CF₃ | 638.6 | 639.6 |
| 1-58 | pyrazin-2-ylmethyl | CF₃ | 610.6 | 611.9 |
| 1-59 | (1-methyl-1H-pyrazol-5-yl)methyl | CF₃ | 612.6 | 613.8 |
| 1-60 | thiazol-4-ylmethyl | CF₃ | 615.6 | 616.8 |
| 1-61 | thiazol-5-ylmethyl | CF₃ | 615.6 | 616.7 |
| 1-62 | thiazol-2-ylmethyl | CF₃ | 615.6 | 616.8 |
| 1-63 | oxazol-4-ylmethyl | CF₃ | 599.5 | 600.9 |
| 1-64 | isoxazol-3-ylmethyl | CF₃ | 599.5 | 600.6 |
| 1-65 | acetyl | CF₃ | 560.5 | 561.5 |
| 1-66 | isobutyryl | CF₃ | 588.5 | 589.6 |
| 1-67 | ethoxycarbonyl | CF₃ | 590.5 | 591.6 |
| 1-68 | methanesulfonyl | CF₃ | 596.5 | 597.5 |
| 1-69 | H | CF₃ | 518.5 | 519.7 |
| 1-70 | 2-(methylsulfonyl)ethyl | CF₃ | 624.6 | 625.6 |
| 1-71 | 3-carbamoylbenzyl | CF₃ | 651.6 | 652.8 |
| 1-72 | 4-carbamoylbenzyl | CF₃ | 651.6 | 652.8 |

TABLE 1-continued

[Structure shown with R4, phenyl, H2N, F, X substituents on spirocyclic pyrimidine-dione-furan scaffold]

| Example | —R4 | X | M.W. | Mass |
|---|---|---|---|---|
| 1-73 | [CH2CH2N(CH3)S(O)2CH3 group] | CF3 | 653.6 | 654.3 |
| 1-74 | [CH2CH2CH2-morpholine group] | CF3 | 631.6 | 632.5 |
| 1-75 | [CH2-(5-CF3-furan-2-yl) group] | CF3 | 666.5 | 666.2 |

Intermediates required for the preparation of compounds of Examples 1-1 to 1-75 were prepared according to the following methods.

Preparation of Intermediates

Synthesis of 2-(N-methylmethylsulfonamido)ethyl methansulfonate

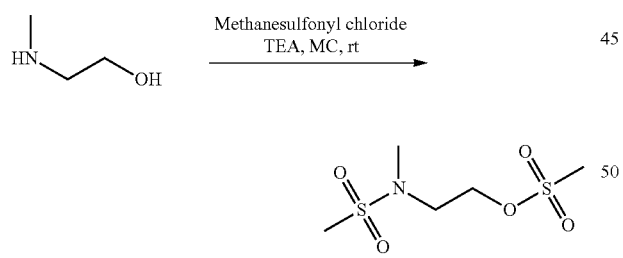

2-(methylamino)ethanol (300 mg, 4 mmol) was mixed with dichloromethane (8 mL) and triethylamine (1.23 mL, 8.8 mmol) was added thereto. Methanesulfonylchloride (0.68 mL, 8.8 mmol) was slowly added to the mixture dropwise at room temperature, and allowed to react for 16 hrs under a nitrogen atmosphere. The reaction was completed by adding water (10 mL) to the reaction solution. The mixture was extracted twice with dichloromethane (10 mL), and the organic layer was separated therefrom. The organic layer was added with sodium sulfate, stirred for approximately 5 min, followed by filtration. The filtrate was concentrated, and dried under vacuum to obtain the title compound as colorless oil (875 mg, yield: 94%).

$^{1}$H NMR (300 MHz, CDCl$_3$) δ 4.38 (t, J=5.4 Hz, 2H), 3.53 (t, J=5.3 Hz, 2H), 3.08 (s, 3H), 2.99 (s, 3H), 2.88 (s, 3H).

Synthesis of 2-(methylsulfonyl)ethyl methanesulfonate Methanesulfonyl chloride

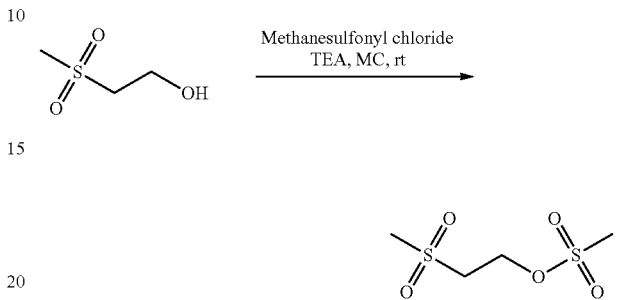

2-(methylsulfonyl)ethanol (497 mg, 4 mmol) was mixed with dichloromethane (8 mL), and triethylamine (0.62 mL, 4.4 mmol) was added thereto. Methanesulfonyl chloride was slowly added thereto dropwise at room temperature, and the mixture was allowed to react for 16 hrs under a nitrogen atmosphere. The reaction was completed by adding water (10 mL) to the reaction solution. The solution was extracted twice with dichloromethane (10 mL) and the organic layer thus obtained was added with sodium sulfate and stirred for approximately 5 min, followed by filtration. The filtrate was concentrated, and dried under vacuum to obtain the title compound as colorless oil (540 mg, yield: 67%).

$^{1}$H NMR (300 MHz, CDCl$_3$) δ 4.70-4.62 (m, 2H), 3.68 (s, 1H), 3.48-3.42 (m, 2H), 3.13-3.08 (m, 3H), 3.04 (d, J=0.9 Hz, 3H).

Synthesis of 2-(bromomethyl)-6-(trifluoromethyl)pyridine

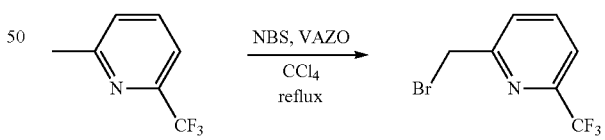

2-methyl-6-(trifluoromethyl)pyridine (100 mg, 0.620 mmol) was dissolved in CCl$_4$ (3 mL), and N-bromosuccinimide (NBS) (110 mg, 0.620 mmol) and 1,1'-azobis(cyclohexanecarbonitrile) (VAZO, 8 mg, 0.031 mmol) were added thereto, followed by heating and stirring at 90° C. for 15 hrs. The reaction solution was filtered, and the filtrate was concentrated under reduced pressure. The resulting residue was purified by MPLC (Hex/EA=5:1) to obtain the title compound as white solid (42.5 mg, yield: 28.4%).

$^{1}$H NMR (300 MHz, CDCl$_3$) δ 4.60 (2H, s), 7.61 (1H, d), 7.68 (1H, d), 7.90 (1H, t)

Example 2

Synthesis of (R)-4-((2-(1'-(3-chlorobenzyl)-1-(2-fluoro-6-(trifluoromethyl)benzyl)-2,4-dioxo-1H-spiro[furo[3,4-d]pyrimidine-5,4'-piperidin]-3(2H,4H,7H)-yl)-1-phenylethyl)amino)butanoic acid (10)

<Method 1>

$^1$H NMR (600 MHz, CDCl$_3$) δ 7.55 (d, J=7.9 Hz, 1H), 7.45 (td, J=8.4, 5.3 Hz, 1H), 7.41-7.36 (m, 3H), 7.36-7.31 (m, 3H), 7.30-7.27 (m, 1H), 7.24-7.18 (m, 3H), 5.22-5.06 (m, 2H), 4.85-4.75 (m, 2H), 4.38 (dd, J=13.7, 10.6 Hz, 1H), 4.27 (dd, J=10.6, 4.3 Hz, 1H), 3.99 (dd, J=13.6, 4.3 Hz, 1H), 3.50 (s, 2H), 2.81-2.64 (m, 3H), 2.56-2.41 (m, 2H), 2.40-2.23 (m, 4H), 1.76-1.52 (m, 3H).

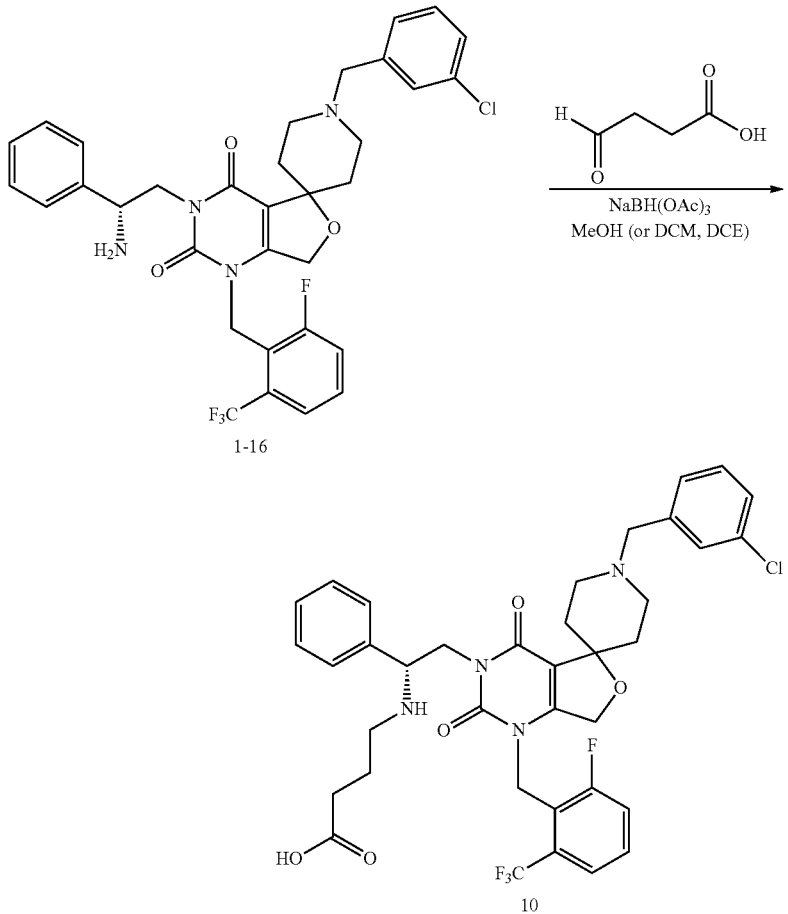

(R)-3-(2-amino-2-phenylethyl)-1'-(3-chlorobenzyl)-1-(2-fluoro-6-(trifluoromethyl)benzyl)-1H-spiro[furo[3,4-d]pyrimidin-5,4'-piperidine]-2,4(3H,7H)-dione (1-16) (93 mg, 0.145 mmol) was dissolved in methanol (2.9 mL) (which may be substituted with dichloromethane or dichloroethane depending on the substrate) and 15% aqueous succinic semialdehyde solution (148 mg, 0.218 mmol) was slowly added thereto dropwise with stirring. Sodium triacetoxyborohydride (307 mg, 1.45 mmol) was added to the mixture and stirred for 2 hrs under a nitrogen atmosphere. The reaction solution was concentrated, added with dichloromethane (10 mL) and a saturated sodium bicarbonate solution (10 mL) to separate layers. The organic layer was extracted twice with dichloromethane (10 mL). The organic layer was added with sodium sulfate and stirred for approximately 5 min, followed by filtration. The filtrate was concentrated, and the resulting residue was purified by silica gel chromatography (eluent: dichloromethane/methanol=10/1~5/1) and dried under vacuum to obtain the title compound as white foam (10) (65 mg, yield: 62%).

<Method 2>

Also, the compound of Example 2 was prepared by the following method.

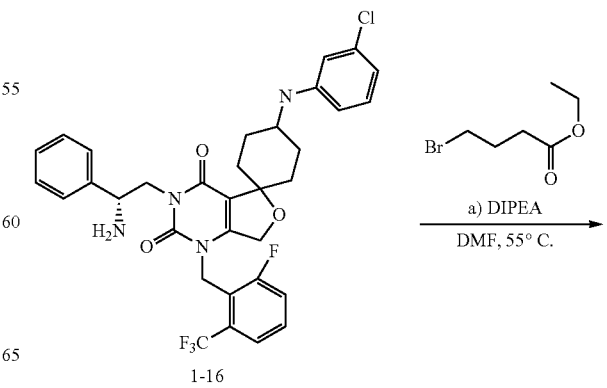

-continued

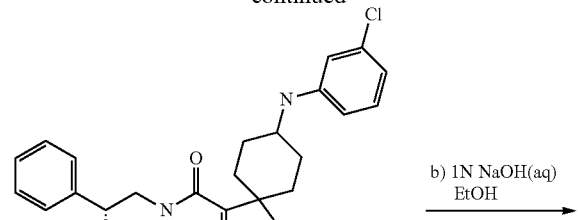

11

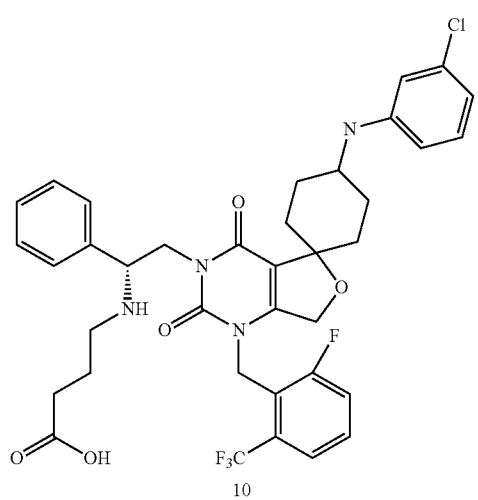

10

Step A. Preparation of (R)-ethyl 4-((2-(1'-(3-chlorobenzyl)-1-(2-fluoro-6-(trifluoromethyl)benzyl)-2,4-dioxo-1H-spiro[furo[3,4-d]pyrimidin-5,4'-piperidine]-3(2H,4H,7H)-yl)-1-phenylethyl)amino)butanoate (11)

(R)-3-(2-amino-2-phenylethyl)-1'-(3-chlorobenzyl)-1-(2-fluoro-6-(trifluoromethyl)benzyl)-1H-spiro[furo[3,4-d]pyrimidin-5,4'-piperidine]-2,4(3H,7H)-dione (1-16) (200 mg, 0.30 mmol) was dissolved in N,N-dimethylformamide (1 mL), and N,N-diisopropylethylamine (DIPEA, 68 μL, 0.39 mmol) and 4-bromo-butyric acid ethyl ester (52 μL, 0.36 mmol) were added in sequence, followed by stirring for 12 hrs at 55° C. The reaction solution was cooled down to room temperature, diluted with a mixed solution of hexane/ethyl acetate (1/1) and washed with a saturated aqueous solution of ammonium chloride to separate the organic layer. The aqueous layer was further extracted once with a mixed solution of hexane/ethyl acetate (1/1), and the organic layer was collected and concentrated under reduced pressure. The resulting residue was purified by silica gel chromatography (eluent: dichloromethane/methanol=98/2~95/5), and dried under vacuum to obtain the title compound as white foam (150 mg, yield: 64%).

Step B. Preparation of (R)-4-((2-(1'-(3-chlorobenzyl)-1-(2-fluoro-6-(trifluoromethyl)benzyl)-2,4-dioxo-1H-spiro[furo[3,4-d]pyrimidin-5,4'-piperidine]-3(2H, 4H, 7H)-yl)-1-phenylethyl)amino)butanoic acid (10)

(R)-ethyl 4-((2-(1'-(3-chlorobenzyl)-1-(2-fluoro-6-(trifluoromethyl)benzyl)-2,4-dioxo-1H-spiro[furo[3,4-d]pyrimidine-5,4'-piperidin]-3(2H,4H,7H)-yl)-1-phenylethyl)amino)butanoate (100 mg, 0.13 mmol) was dissolved in ethanol (1 mL), and an aqueous solution of 1N NaOH (380 μL, 0.39 mmol) was slowly added thereto. The mixture was stirred for 1 hr at room temperature and concentrated. The resulting residue was neutralized with an aqueous solution of 1N HCl, diluted with dichloromethane, and the organic layer was separated therefrom. The organic layer was dried over $Na_2SO_4$, filtered, and concentrated under reduced pressure to obtain the title compound as white foam (60 mg, yield: 90%).

$^1$H NMR (600 MHz, $CDCl_3$) δ 7.55 (d, J=7.9 Hz, 1H), 7.45 (td, J=8.4, 5.3 Hz, 1H), 7.41-7.36 (m, 3H), 7.36-7.31 (m, 3H), 7.30-7.27 (m, 1H), 7.24-7.18 (m, 3H), 5.22-5.06 (m, 2H), 4.85-4.75 (m, 2H), 4.38 (dd, J=13.7, 10.6 Hz, 1H), 4.27 (dd, J=10.6, 4.3 Hz, 1H), 3.99 (dd, J=13.6, 4.3 Hz, 1H), 3.50 (s, 2H), 2.81-2.64 (m, 3H), 2.56-2.41 (m, 2H), 2.40-2.23 (m, 4H), 1.76-1.52 (m, 3H).

<Method 3>

Also, the compound of Example 2 was prepared by the following method.

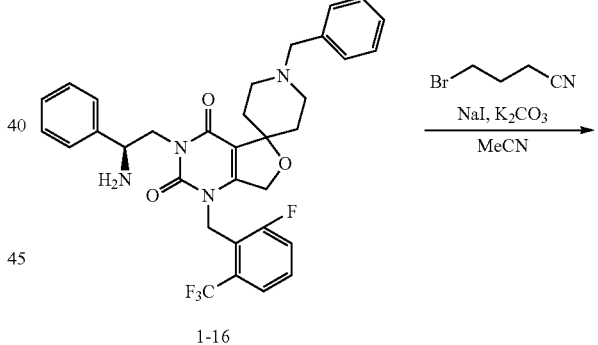

1-16

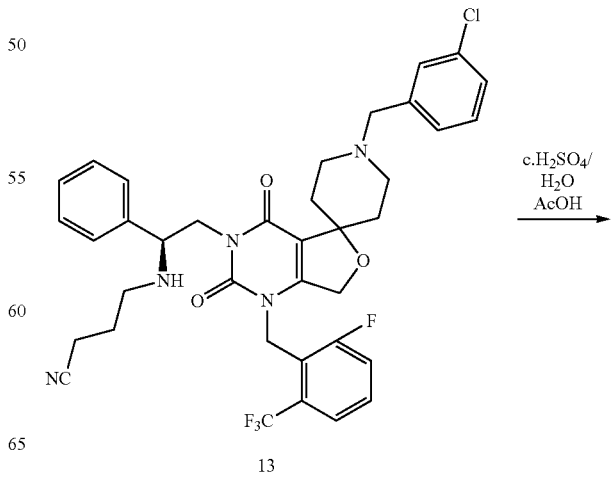

13

-continued

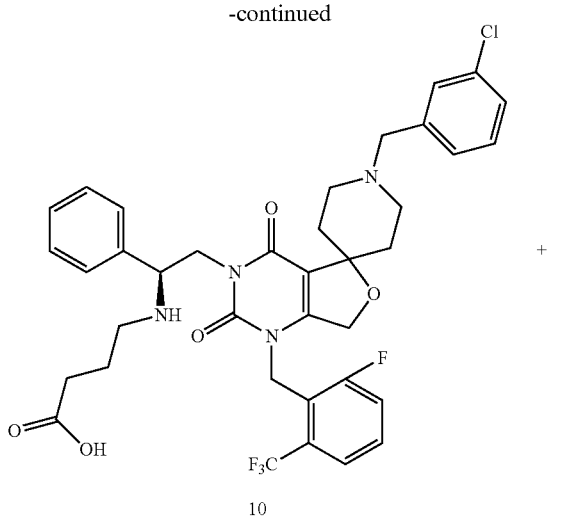

10

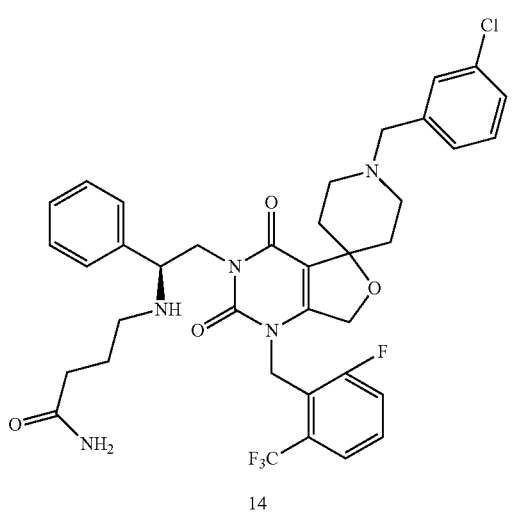

14

Step A. Preparation of (R)-4-((2-(1'-(3-chlorobenzyl)-1-(2-fluoro-6-(trifluoromethyl)benzyl)-2,4-dioxo-1H-spiro[furo[3,4-d]pyrimidine-5,4'-piperidin]-3 (2H,4H,7H)-yl)-1-phenylethyl)amino) butanenitrile (13)

(R)-3-(2-amino-2-phenylethyl)-1'-(3-chlorobenzyl)-1-(2-fluoro-6-(trifluoromethyl)benzyl)-1H-spiro[furo[3,4-d]pyrimidine-5,4'-piperidine]-2,4(3H,7H)-dione (1-16) (10 g, 15 mmol) was dissolved in acetonitrile (200 mL), and then NaI (6.2 g, 45 mmol), $K_2CO_3$ (6.8 g, 45 mmol) and 4-bromobutanenitrile (2.3 mL, 22.5 mmol) were added to the mixture in sequence, followed by stirring for 12 hrs at 95° C. The resulting solution was cooled down to room temperature, filtered, and concentrated under reduced pressure to remove acetonitrile therefrom. The resulting solution was diluted with dichloromethane, washed with a saturated aqueous ammonium chloride solution, and the organic layer was separated. The organic layer was concentrated under reduced pressure and the resulting residue was purified by silica gel chromatography (eluent: dichloromethane/methanol=98/2~95/5) and dried under vacuum to obtain the title compound as white foam (8.2 g, yield: 75%).

Step B. Preparation of (R)-4-((2-(1'-(3-chlorobenzyl)-1-(2-fluoro-6-(trifluoromethyl)benzyl)-2,4-dioxo-1H-spiro[furo[3,4-d]pyrimidine-5,4'-piperidin]-3(2H, 4H, 7H)-yl)-1-phenylethyl)amino)butanoic acid (10)

(R)-4-((2-(1'-(3-chlorobenzyl)-1-(2-fluoro-6-(trifluoromethyl)benzyl)-2,4-dioxo-1H-spiro[furo[3,4-d]pyrimidine-5,4'-piperidin]-3(2H,4H,7H)-yl)-1-phenylethyl)amino)butanenitrile (7.1 g, 9.7 mmol) was dissolved in acetic acid (215 mL), and the mixture was cooled with ice water. Water (130 mL) and concentrated sulfuric acid (130 mL) were slowly added to the mixture. The resulting mixture was stirred for 1 hr at room temperature, and stirred for 12 hrs at 80° C. The resulting solution was cooled down to room temperature, and 5N NaOH solution was added thereto to adjust pH 6. The solution was extracted with ethyl acetate (1,500 mL), dried over anhydrous $MgSO_4$, filtered, and concentrated under reduced pressure. The resulting solution was diluted with ethyl acetate (70 mL), stirred, and added with 1N HCl solution (22 mL, 1.5 mmol). The white precipitates formed were filtered, and washed with ether (50 mL). The filtered solid was dissolved in water (200 mL), and 2N NaOH solution was added thereto to adjust pH 6. The resulting solution was extracted three times with ethyl acetate (150 mL), dried over anhydrous $MgSO_4$, filtered, and concentrated under reduced pressure. The resulting residue was purified by silica gel chromatography (eluent: acetonitrile/methanol=3/1), and dried under vacuum to obtain the title compound as white foam (5.3 g, yield: 73%).

$^1$H NMR (300 MHz, $CDCl_3$) δ 1.67 (4H, m), 2.30-2.58 (7H, m), 2.63-2.87 (3H, m), 3.61 (2H, s), 4.00 (1H, dd), 4.27 (1H, dd), 4.38 (1H, dd), 4.78 (2H, s), 5.13 (2H, m), 6.29 (1H, d), 6.72 (1H, d), 7.25-7.48 (7H, m), 7.55 (1H, d)

Moreover, (R)-4-((2-(1'-(3-chlorobenzyl)-1-(2-fluoro-6-(trifluoromethyl)benzyl)-2,4-dioxo-1H-spiro[furo[3,4-d]pyrimidine-5,4'-piperidin]-3(2H,4H,7H)-yl)-1-phenylethyl)amino)butanamide (compound 14) obtained during the silica gel chromatography purification process was dried under vacuum to yield the title compound as white foam (400 mg, yield: 5%).

Examples 2-1 to 2-15

The compounds of Examples 2-1 to 2-15 were prepared in the same manner as described in Example 2 above, except for using each compound comprising the corresponding $R_4$ group shown in Table 2 below instead of the compound of Example 1-16 as a starting material.

TABLE 2

| Example | —R₄ | X | Chiral (*) | M.W. | Mass |
|---|---|---|---|---|---|
| 2-1 | 3-CF₃-benzyl | CF₃ | (R) | 762.7 | 762.9 |
| 2-2 | 3-CF₃-benzyl | F | (R) | 712.7 | 712.8 |
| 2-3 | 5-methyl-furan-2-ylmethyl | CF₃ | (R) | 698.7 | 698.0 |
| 2-4 | 5-chloro-furan-2-ylmethyl | CF₃ | (R) | 719.1 | 718.5 |
| 2-5 | 3-cyano-2-fluoro-benzyl | CF₃ | (R) | 737.7 | 738.4 |
| 2-6 | 5-CF₃-furan-2-ylmethyl | F | (R) | 702.6 | 703.8 |
| 2-7 | 3-chloro-benzyl | F | (R) | 679.1 | 680.0 |
| 2-8 | 3-cyano-benzyl | F | (R) | 669.7 | 670.6 |
| 2-9 | 3-cyano-benzyl | CF₃ | (R) | 719.7 | 720.7 |
| 2-10 | 3-chloro-benzyl | CF₃ | (R) | 729.1 | 729.8 |
| 2-11 | 3-(N-methylcarbamoyl)-benzyl | CF₃ | (R) | 751.7 | 752.5 |
| 2-12 | 3-methylthio-benzyl | CF₃ | (R) | 740.8 | 741.7 |
| 2-13 | 5-CF₃-furan-2-ylmethyl | CF₃ | (R) | 752.68 | 753.7 |
| 2-14 | 3-chloro-benzyl | CF₃ | (S) | 729.1 | 729.8 |
| 2-15 | 5-CF₃-furan-2-ylmethyl | CF₃ | (S) | 752.68 | 753.7 |

Example 3

Synthesis of (R)-3-(2-amino-2-phenylethyl)-1'-(3-chlorobenzyl)-1-(2-fluoro-6-(trifluoromethyl)benzyl)-6,7-dihydrospiro[cyclopenta[d]pyrimidine-5,4'-piperidine]-2,4(1H,3H)-dione (26)

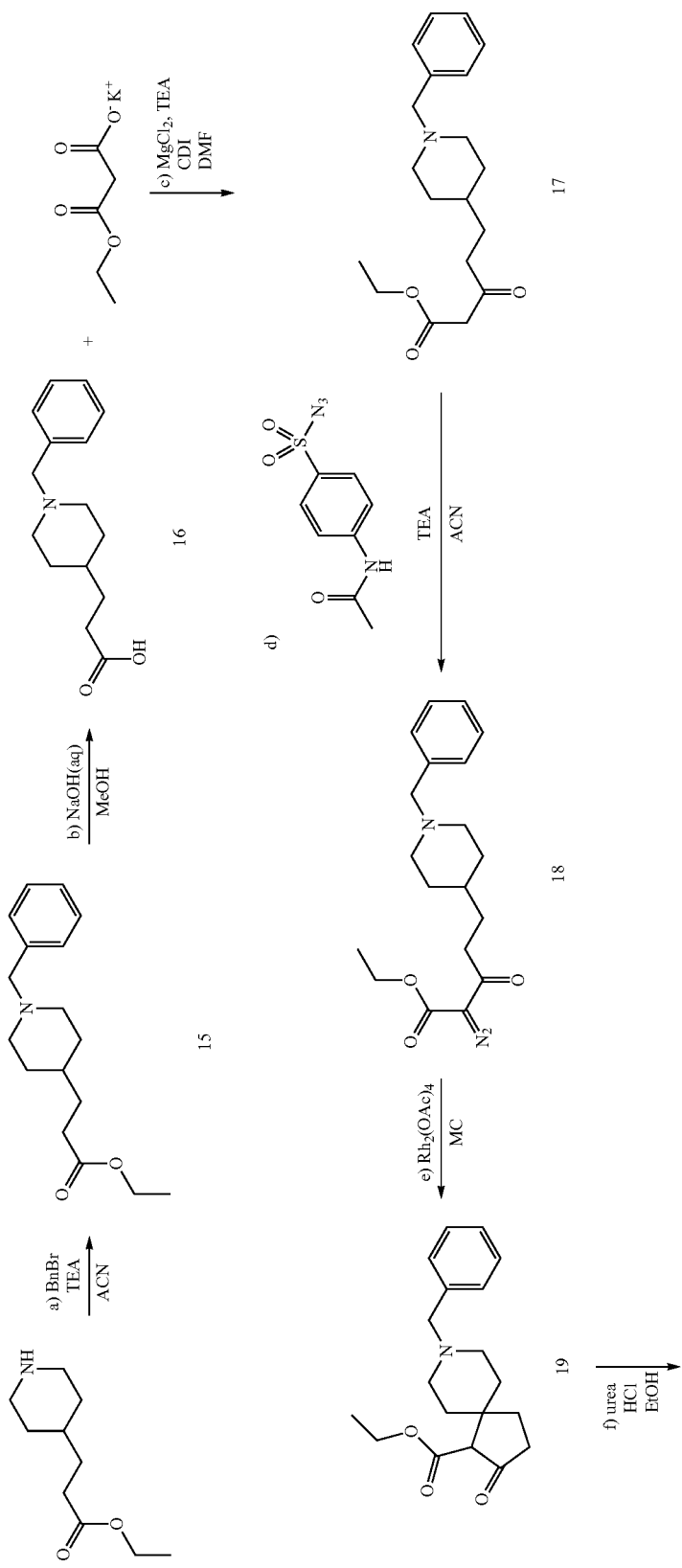

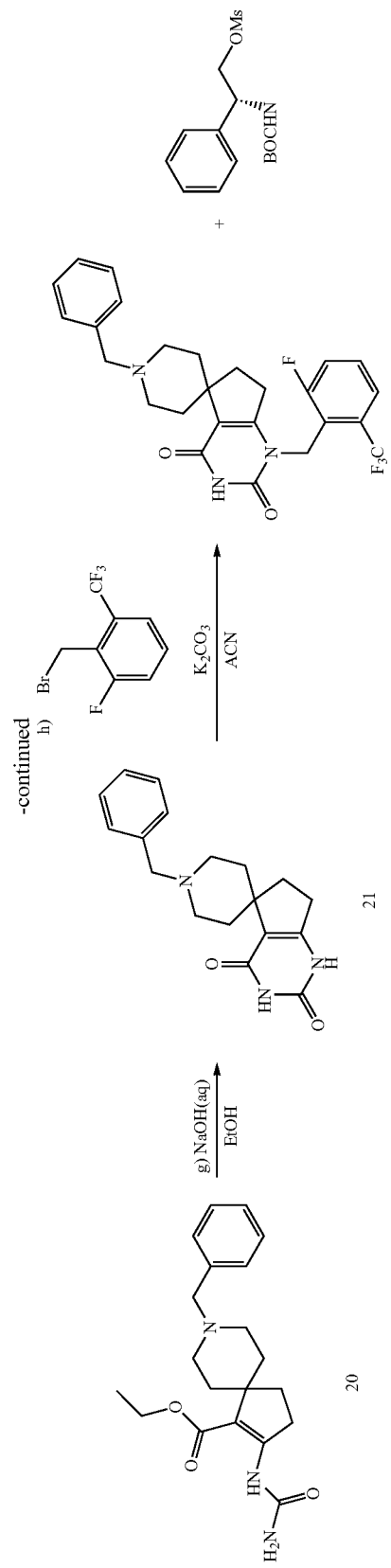

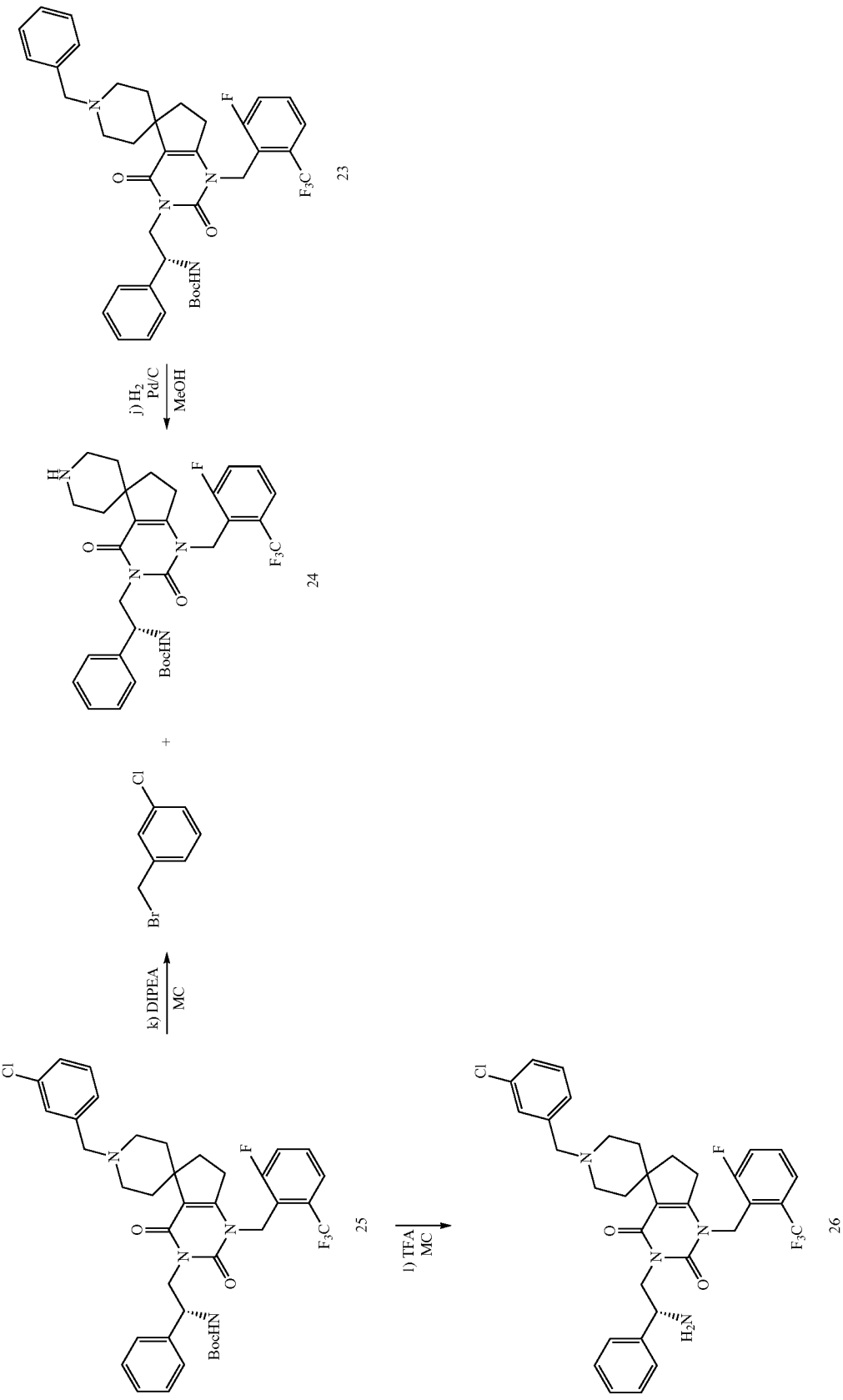

Step A. Preparation of ethyl 3-(1-benzylpiperidin-4-yl)propionate (15)

Ethyl 3-(piperidin-4-yl)propionate (5 g, 26.989 mmol) was added to acetonitrile (150 mL), and then triethylamine (8.3 mL, 59.376 mmol) was added thereto, followed by stirring. Subsequently, benzyl bromide (6.45 mL, 53.978 mmol) was added to the resulting solution in an ice bath. The mixture was heated to room temperature, stirred overnight and concentrated under reduced pressure. The concentrated reaction solution was diluted with distilled water (500 mL), extracted twice with ethyl acetate (300 mL). The organic layer was dried over $MgSO_4$, concentrated, and purified by MPLC (ethyl acetate/hexane=1/4~1/1) to obtain the title compound as yellow oil (2.75 g, yield: 37%).

$^1$H NMR (300 MHz, $CDCl_3$) δ 7.31-7.21 (m, 5H), 4.12 (q, 2H), 3.48 (s, 2H), 2.86 (m, 2H), 2.30 (m, 2H), 1.92 (m, 2H), 1.57 (m, 4H), 1.28-1.20 (m, 3H), 1.25 (t, 3H)

Step B. Preparation of 3-(1-benzylpiperidin-4-yl)propionic acid (16)

Ethyl 3-(1-benzylpiperidin-4-yl)propionate (15) (2.75 g, 9.982 mmol) prepared in Step A was dissolved in methanol (10 mL), and an aqueous solution of 1N NaOH (30 mL, 29.947 mmol) was added thereto, and stirred overnight at room temperature. The resulting solution was neutralized with an aqueous solution of 1N HCl in an ice bath, and the reaction solution was concentrated under reduced pressure. The concentrate was diluted with methanol/dichloromethane (1/9), and dried over $MgSO_4$. The filtrate was concentrated under reduced pressure to obtain the title compound as white solid (crude, 2.38 g).

MS (ESI) m/z 248.4 ($MH^+$)

Step C. Preparation of ethyl 5-(1-benzylpiperidin-4-yl)-3-oxopentanoate (17)

Potassium ethyl malonate (2.57 g, 15.113 mmol) was added to a suspension of magnesium chloride (1.64 g, 17.272 mmol), triethylamine (3.1 mL, 22.310 mmol) and acetonitrile (150 mL) and stirred for 2 hrs at room temperature to prepare Reaction solution 1. 3-(1-benzylpiperidin-4-yl)propionic acid (16) (1.78 g, 7.197 mmol) prepared in Step B was added to N,N,-dimethylformamide (50 mL), and 1,1'-carbonyldiimidazole (1.28 g, 7.917 mmol) was added thereto and stirred for 2 hrs at room temperature to prepare Reaction solution 2.

Reaction solution 1 was added to Reaction solution 2, and stirred overnight at room temperature. The resulting solution was diluted with ethyl acetate, and washed with distilled water several times. The organic layer was dried over $MgSO_4$, and concentrated to obtain the title compound as yellow oil (crude, 2.02 g).

$^1$H NMR (300 MHz, $CDCl_3$) δ 7.32-7.21 (m, 5H), 4.19 (q, 2H), 3.50 (s, 2H), 3.43 (s, 2H), 2.88 (m, 2H), 2.55 (t, 2H), 1.94 (m, 2H), 1.56 (m, 4H), 1.31-1.24 (m, 3H), 1.27 (t, 3H)

Step D. Preparation of ethyl 5-(1-benzylpiperidin-4-yl)-2-diazo-3-oxopentanoate (18)

Ethyl 5-(1-benzylpiperidin-4-yl)-3-oxopentanoate (17) (2.14 g, 6.751 mmol) prepared in Step C was added to acetonitrile (70 mL) together with triethylamine (1.04 mL, 7.426 mmol), stirred, followed by adding 4-acetamidobenzenesulfonyl azide (1.622 g, 6.751 mmol) thereto. The mixture was stirred overnight and concentrated under reduced pressure, and added with diethyl ether, followed by stirring. The reaction solution was filtered, concentrated, and purified by MPLC (ethyl acetate/hexane=1/4~1/1) to obtain the title compound as yellow oil (2.05 g, yield: 88%).

$^1$H NMR (300 MHz, $CDCl_3$) δ 7.31-7.20 (m, 5H), 4.29 (q, 2H), 3.47 (s, 2H), 2.85 (m, 4H), 1.92 (m, 2H), 1.55 (m, 4H), 1.32 (t, 3H), 1.32-1.23 (m, 3H)

Step E. Preparation of ethyl 8-benzyl-2-oxo-8-azaspiro[4.5]decane-1-carboxylate (19)

A solution prepared by adding ethyl 5-(1-benzylpiperidin-4-yl)-2-diazo-3-oxopentanoate (18) (1.43 g, 4.164 mmol) prepared in Step D to dichloromethane (30 mL) was added to a suspension of rhodium (II) acetate dimer (92 mg, 0.208 mmol) and dichloromethane (25 mL) under a nitrogen atmosphere, followed by stirring overnight at room temperature. The reaction solution was concentrated under reduced pressure, and purified by MPLC (ethyl acetate/hexane=1/4~2/3) to obtain the title compound as yellow oil (impure, 985 mg).

MS (ESI) m/z 316.7 ($MH^+$)

Step F. Preparation of ethyl 8-benzyl-2-ureido-8-azaspiro[4.5]dec-1-ene-1-carboxylate (20)

4.0 M HCl in 1,4-dioxane (0.2 mL, 0.793 mmol) was added to a solution prepared by adding ethyl 8-benzyl-2-oxo-8-azaspiro[4.5]decane-1-carboxylate (19) (50 mg, 0.159 mmol) prepared in Step E and urea (95 mL, 1.585 mmol) to ethanol (2 mL), and the mixture was stirred under a reflux condition for 5 hrs at 100° C. The reaction solution was cooled down to room temperature, and neutralized with an aqueous solution of 2N NaOH. The solid thus obtained was filtered, washed with ethanol, and dried under vacuum to obtain the title compound as white solid (22 mg, yield: 40%).

$^1$H NMR (300 MHz, DMSO-$d_6$) δ 9.67 (s, 1H), 7.34-7.20 (m, 5H), 6.73 (br s, 2H), 4.17 (q, 2H), 3.44 (s, 2H), 2.96 (t, 2H), 2.66 (d, 2H), 2.26 (m, 2H), 2.01 (m, 2H), 1.68 (t, 2H), 1.26 (t, 3H), 1.11 (d, 2H)

MS (ESI) m/z 358.4 ($MH^+$)

Step G. Preparation of 1'-benzyl-6,7-dihydrospiro[cyclopenta[d]pyrimidine-5,4'-piperidine]-2,4(1H,3H)-dione (21)

Ethyl 8-benzyl-2-ureido-8-azaspiro[4.5]dec-1-ene-1-carboxylate (20) (15 mg, 0.0437 mmol) prepared in Step F was added to ethanol (1 mL) and an aqueous solution of 2N NaOH (0.16 mL, 0.320 mmol) was added thereto, and allowed to react for 1 hr at 70° C. The reaction solution was cooled down to room temperature, neutralized with an aqueous solution of 1N HCl, and then concentrated under reduced pressure. The concentrate was diluted with 10% methanol/dichloromethane, and dried over $Na_2SO_4$. The filtrate was concentrated under reduced pressure, and dried to obtain the title compound as white solid (13 mg, yield: 96%).

$^1$H NMR (300 MHz, DMSO-$d_6$) δ 7.34-7.21 (m, 5H), 3.43 (s, 2H), 2.68 (d, 2H), 2.57 (t, 2H), 2.24 (m, 2H), 1.97 (m, 2H), 1.84 (t, 2H), 1.22 (d, 2H)

MS (ESI) m/z 312.7 ($MH^+$)

Step H. Preparation of 1'-benzyl-1-(2-fluoro-6-(trifluoromethyl)benzyl)-6,7-dihydrospiro[cyclopenta[d]pyrimidine-5,4'-piperidine]-2,4(1H,3H)-dione (22)

The procedure for preparing compound 5 in Example 1 (Step E of Example 1) was repeated using 1'-benzyl-6,7-dihydrospiro[cyclopenta[d]pyrimidin-5,4'-piperidine]-2,4 (1H,3H)-dione (21) (30 mg, 0.0963 mmol) to obtain the title compound as white solid (23 mg, yield: 48%).

$^1$H NMR (300 MHz, CDCl$_3$) δ 8.53 (s, 1H), 7.54-7.20 (m, 8H), 5.22 (s, 2H), 3.50 (s, 2H), 2.81 (d, 2H), 2.62 (t, 2H), 2.53 (m, 2H), 1.98 (m, 4H), 1.29 (d, 2H)

Step I. Preparation of (R)-tert-butyl (2-(1'-benzyl-1-(2-fluoro-6-(trifluoromethyl)benzyl)-2,4-dioxo-1,2,6,7-tetrahydrospiro[cyclopenta[d]pyrimidine-5,4'-piperidin]-3(4H)-yl)-1-phenylethyl)carbamate (23)

The procedure for preparing compound 6 in Example 1 (Step F of Example 1) was repeated using 1'-benzyl-1-(2-fluoro-6-(trifluoromethyl)benzyl)-6,7-dihydrospiro[cyclopenta[d]pyrimidine-5,4'-piperidine]-2,4(1H,3H)-dione (22) (20 mg, 0.0410 mmol) to obtain the title compound as white solid (14 mg, yield: 48%).

$^1$H NMR (300 MHz, CDCl$_3$) δ 7.41-7.23 (m, 13H), 5.81 (d, 1H), 5.26 (m, 2H), 4.99 (m, 1H), 4.27 (m, 1H), 4.02 (m, 1H), 3.52 (s, 2H), 2.84-2.57 (m, 6H), 2.05-1.88 (m, 4H), 1.35 (s, 9H), 1.28 (m, 2H)

Step J. Preparation of (R)-tert-butyl (2-(1-(2-fluoro-6-(trifluoromethyl)benzyl)-2,4-dioxo-1,2,6,7-tetrahydrospiro[cyclopenta[d]pyrimidine-5,4'-piperidin]-3(4H)-yl)-1-phenylethyl)carbamate (24)

The procedure for preparing compound 7 in Example 1 (Step G of Example 1) was repeated using (R)-tert-butyl (2-(1'-benzyl-1-(2-fluoro-6-(trifluoromethyl)benzyl)-2,4-dioxo-1,2,6,7-tetrahydrospiro[cyclopenta[d]pyrimidine-5,4'-piperidin]-3(4H)-yl)-1-phenylethyl)carbamate (23) (159 mg, 0.225 mmol) to obtain the title compound as white solid (69 mg).

$^1$H NMR (300 MHz, CDCl$_3$) δ 7.57-7.20 (m, 8H), 5.75 (d, 1H), 5.23 (m, 2H), 5.01 (m, 1H), 4.23 (m, 1H), 4.05 (m, 1H), 3.63 (m, 2H), 3.10 (t, 2H), 2.72 (m, 4H), 2.03 (m, 2H), 1.65 (d, 2H), 1.34 (s, 9H)

Step K. Preparation of (R)-tert-butyl (2-(1'-(3-chlorobenzyl)-1-(2-fluoro-6-(trifluoromethyl)benzyl)-2,4-dioxo-1,2,6,7-tetrahydrospiro[cyclopenta[d]pyrimidine-5,4'-piperidin]-3(4H)-yl)-1-phenylethyl)carbamate (25)

The procedure for preparing compound 8 in Example 1 (Step H of Example 1) was repeated using (R)-tert-butyl (2-(1-(2-fluoro-6-(trifluoromethyl)benzyl)-2,4-dioxo-1,2,6,7-tetrahydrospiro[cyclopenta[d]pyrimidine-5,4'-piperidin]-3(4H)-yl)-1-phenylethyl)carbamate (24) (66 mg, 0.107 mmol) and 3-chlorobenzyl bromide (29 mg, 0.128 mmol) to obtain the title compound as colorless oil (47 mg, yield: 57%).

MS (ESI) m/z 741.9 (M$^+$)

Step L. Preparation of (R)-3-(2-amino-2-phenylethyl)-1'-(3-chlorobenzyl)-1-(2-fluoro-6-(trifluoromethyl)benzyl)-6,7-dihydrospiro[cyclopenta[d]pyrimidine-5,4'-piperidine]-2,4(1H,3H)-dione (26)

The procedure for preparing compound 9 in Example 1 (Step I of Example 1) was repeated using (R)-tert-butyl (2-(1'-(3-chlorobenzyl)-1-(2-fluoro-6-(trifluoromethyl)benzyl)-2,4-dioxo-1,2,6,7-tetrahydrospiro[cyclopenta[d]pyrimidine-5,4'-piperidin]-3(4H)-yl)-1-phenylethyl)carbamate (25) (47 mg, 0.0615 mmol) to obtain the title compound as white solid (34 mg, yield: 84%).

MS (ESI) m/z 641.8 (M$^+$)

Examples 3-1 to 3-6

The compounds of Examples 3-1 to 3-6 were prepared in the same manner as described in Example 3 above, except for using R$_4$-halide or aldehyde reagent for introducing the corresponding R$_4$ group shown in Table 3 below instead of 3-chlorobenzyl bromide in Step K of Example 3.

TABLE 3

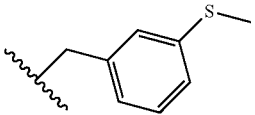 [SMILES: *Cc1cccc(SC)c1]

| No. | —R$_4$ | M.W. | Mass |
|---|---|---|---|
| 3-1 | 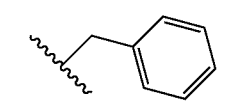 [SMILES: *Cc1ccccc1] | 652.7 | 654.1 |
| 3-2 | 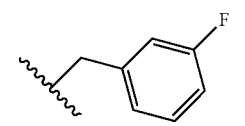 [SMILES: *Cc1cccc(F)c1] | 606.6 | 607.7 |
| 3-3 | 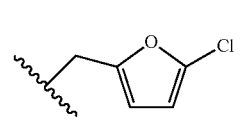 | 624.6 | 624.7 |
| 3-4 | 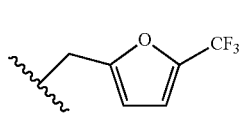 [SMILES: *Cc1ccc(C(F)(F)F)o1] | 631.0 | 631.7 |
| 3-5 | 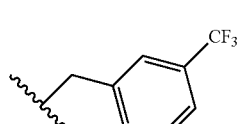 | 664.6 | 664.9 |
| 3-6 | | 674.6 | 675.1 |

Example 4

Synthesis of (R)-4-((2-(1'-(3-chlorobenzyl)-1-(2-fluoro-6-(trifluoromethyl)benzyl)-2,4-dioxo-1,2,6,7-tetrahydrospiro[cyclopenta[d]pyrimidine-5,4'-piperidin]-3(4H)-yl)-1-phenylethyl)amino)butanoic acid (27)

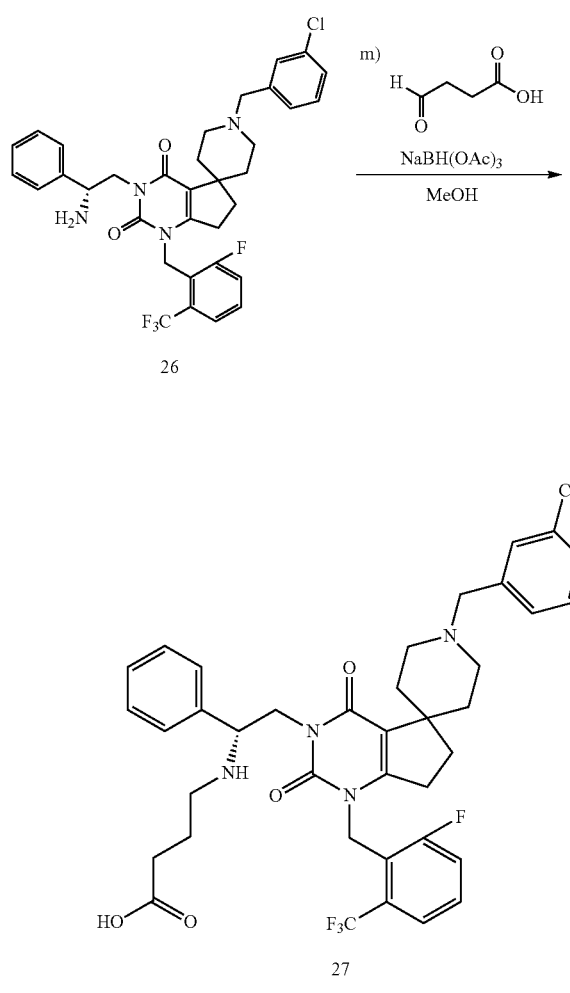

Step M. Preparation of (R)-4-((2-(1'-(3-chlorobenzyl)-1-(2-fluoro-6-(trifluoromethyl)benzyl)-2,4-dioxo-1,2,6,7-tetrahydrospiro[cyclopenta[d]pyrimidine-5,4'-piperidin]-3(4H)-yl)-1-phenylethyl)amino)butanoic acid (27)

The procedure for preparing compound 10 in Example 2 (Method 1) was repeated using (R)-3-(2-amino-2-phenylethyl)-1'-(3-chlorobenzyl)-1-(2-fluoro-6-(trifluoromethyl)benzyl)-6,7-dihydrospiro[cyclopenta[d]pyrimidine-5,4'-piperidine]-2,4(1H,3H)-dione (26) (29 mg, 0.0436 mmol) to obtain the title compound as white amorphous solid (15 mg, yield: 45%).

MS (ESI) m/z 727.8 (MH$^+$)

Examples 4-1 to 4-6

The compounds of Examples 4-1 to 4-6 were prepared in the same manner as described in Example 4 above, except for using each compound comprising the corresponding $R_4$ group shown in Table 4 below instead of the compound (26) of Example 4 as a starting material.

TABLE 4

| Example | —$R_4$ | M.W. | Mass |
|---|---|---|---|
| 4-1 | 3-(methylthio)benzyl | 738.8 | 740.2 |
| 4-2 | benzyl | 692.7 | 693.8 |
| 4-3 | 3-fluorobenzyl | 710.7 | 710.8 |
| 4-4 | (5-chlorofuran-2-yl)methyl | 717.1 | 717.8 |
| 4-5 | (5-(trifluoromethyl)furan-2-yl)methyl | 750.7 | 751.0 |
| 4-6 | 3-(trifluoromethyl)benzyl | 760.7 | 761.2 |

Example 5

Synthesis of (R)-3-(2-((3-(2H-tetrazol-5-yl)propyl)amino)-2-phenylethyl)-1-(2-fluoro-6-(trifluoromethyl)benzyl)-1'-((5-(trifluoromethyl)furan-2-yl)methyl)-1H-spiro[furo[3,4-d]pyrimidine-5,4'-piperidine]-2,4(3H,7H)-dione (30)

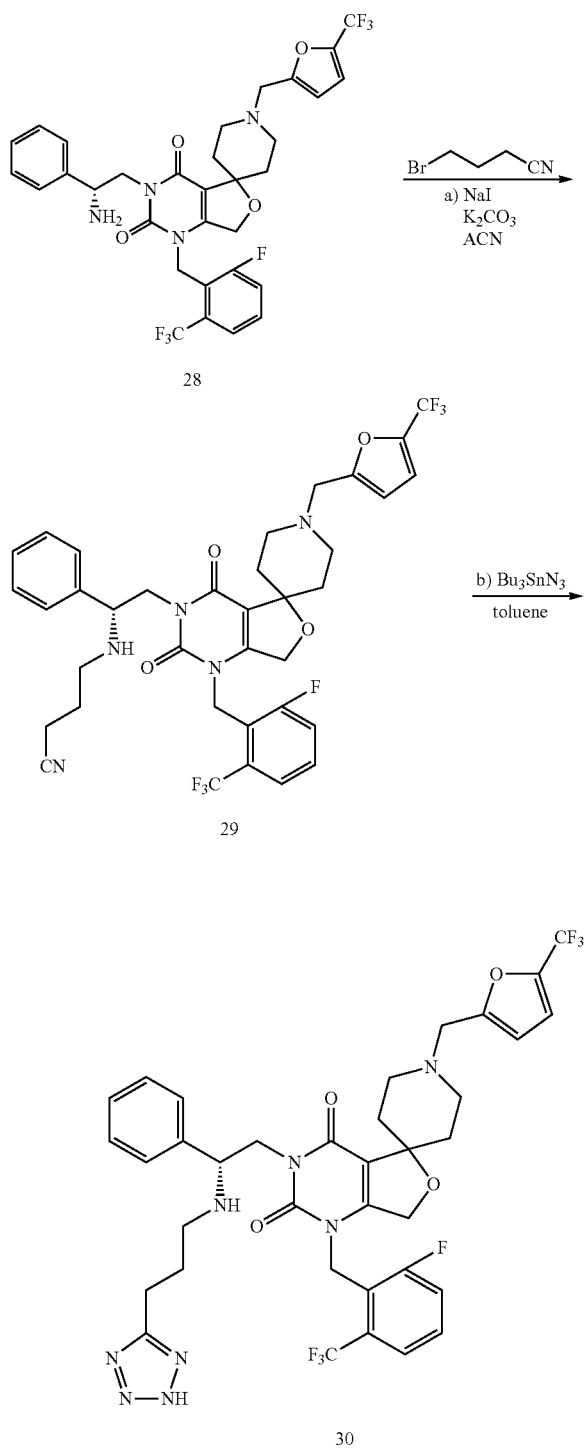

Step A. Preparation of (R)-4-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-phenylethyl)amino)butanenitrile (29)

4-bromobutanenitrile (51.4 μL, 0.517 mmol), NaI (155 mg, 1.035 mmol) and $K_2CO_3$ (143 mg, 1.035 mmol) were added to a solution prepared by adding (R)-3-(2-amino-2-phenylethyl)-1-(2-fluoro-6-(trifluoromethyl)benzyl)-1'-((5-(trifluoromethyl)furan-2-yl)methyl)-1H-spiro[furo[3,4-d]pyrimidine-5,4'-piperidine]-2,4(3H,7H)-dione (28) (230 mg, 0.345 mmol) to ACN (3.45 mL), and stirred for 23 hrs at 90° C. The reaction solution was cooled down to room temperature and concentrated. A saturated $NH_4Cl$ solution was added to the resulting solution, and extracted with dichloromethane (DCM). The organic layer was dried over $MgSO_4$, concentrated, and purified by MPLC (methanol/DCM=1/45~1/24) to obtain the title compound as yellow foam (185.5 mg, yield: 73%).

$^1$H NMR (300 MHz, $CDCl_3$) δ 7.57 (1H, d), 7.48 (1H, dd), 7.39-7.28 (5H, m), 7.24 (1H, d), 6.72 (1H, d), 6.29 (1H, d), 5.23-5.06 (2H, m), 4.70 (2H, s), 4.22 (1H, dd), 3.99 (2H, ddd), 3.61 (2H, s), 2.79 (2H, d), 2.56 (1H, dt), 2.48-2.22 (7H, m), 1.76-1.40 (6H, m).

Step B. Preparation of (R)-3-(2-((3-(2H-tetrazol-5-yl)propyl)amino)-2-phenylethyl)-1-(2-fluoro-6-(trifluoromethyl)benzyl)-1'-((5-(trifluoromethyl)furan-2-yl)methyl)-1H-spiro[furo[3,4-d]pyrimidine-5,4'-piperidine]-2,4(3H,7H)-dione (30)

Azido tributyltin(IV) (204 μL, 0.74 mmol) was added to a solution prepared by adding (R)-4-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-phenylethyl)amino)butanenitrile (29) (135.5 mg, 0.185 mmol) prepared in Step A to toluene (1 mL) in a sealed tube, and stirred for 23 hrs at 120° C. The resulting solution was cooled down to room temperature, added with a saturated $NH_4Cl$ solution, and then extracted with DCM. The organic layer was dried over $MgSO_4$, concentrated, and purified by MPLC (methanol/DCM=1/99~1/9) to obtain the title compound as white foam (58.3 mg, yield: 40%).

$^1$H NMR (300 MHz, $CDCl_3$) δ 7.54 (d, 1H), 7.47 (d, 1H), 7.42 (d, 1H), 7.40-7.31 (m, 3H), 7.22 (d, 1H), 6.71 (dd, 1H), 6.28 (d, 1H), 5.17 (s, 2H), 4.87 (s, 2H), 4.46 (dd, 1H), 4.30 (dd, 1H), 4.04 (dd, 1H), 3.59 (d, 2H), 3.23-3.07 (m, 1H), 3.06-2.91 (m, 1H), 2.78 (dt, 3H), 2.31 (ddd, 5H), 2.05 (s, 1H), 1.74 (s, 1H), 1.58 (d, 1H), 1.48 (d, 1H).

MS(ESI) m/z 777.6 ($MH^+$)

Example 6

Synthesis of (R)-2-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-phenylethyl)amino)ethyl methoxycarbamate (31)

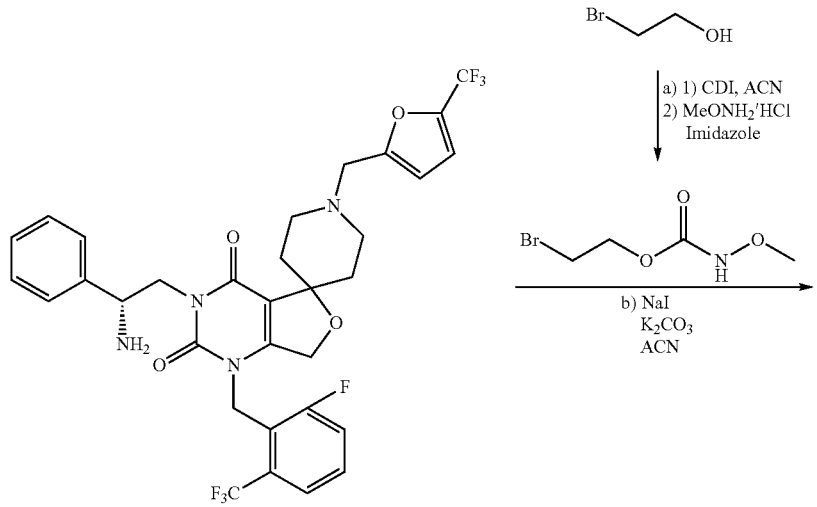

Step A. Preparation of 2-bromoethyl methoxycarbamate

CDI (3.43 g, 21.15 mmol) was added to a solution prepared by adding 2-bromoethanol (1 mL, 14.1 mmol) to ACN (79.5 mL), and stirred for 1 hr at room temperature. When the reaction was completed, methoxyamine HCl (5.89 g, 70.5 mmol) and imidazole (3.84 g, 56.4 mmol) were added to the reaction mixture, followed by stirring for 6 hrs at room temperature. The resulting solution was concentrated, added with 1N HCl, and extracted with DCM. The organic layer was dried over MgSO$_4$, concentrated, and purified by MPLC (ethyl acetate/hexane=1/9~2/3) to obtain the title compound as clear oil (2.64 g, yield: 95%).

Step B. Preparation of (R)-2-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-phenylethyl)amino)ethyl methoxycarbamate (31)

A solution prepared by adding (R)-3-(2-amino-2-phenylethyl)-1-(2-fluoro-6-(trifluoromethyl)benzyl)-1'-((5-(trifluoromethyl)furan-2-yl)methyl)-1H-spiro[furo[3,4-d]pyrimidine-5,4'-piperidine]-2,4(3H,7H)-dione (28) (493.3 mg, 0.74 mmol) to ACN (4.5 mL) was added with 2-bromoethyl methoxycarbamate (267.3 mg, 1.35 mmol) prepared in Step A, sodium iodide (202.3 mg, 1.35 mmol) and K$_2$CO$_3$ (186.6 mg, 1.35 mmol), followed by stirring for 14 hrs at 100° C. The resulting solution was cooled down to room temperature, and concentrated. A saturated NH$_4$Cl solution was added to the mixture, and the resulting solution was extracted with DCM. The organic layer was dried over MgSO₄, concentrated, and purified by MPLC (methanol/DCM=1/191~1/24) to obtain the title compound as white foam (72.8 mg, yield: 12%).

¹H NMR (300 MHz, CDCl₃) δ 7.56 (d, 1H), 7.52-7.41 (m, 1H), 7.35 (d, 3H), 7.30 (s, 1H), 6.75-6.68 (m, 1H), 6.29 (d, 1H), 5.90 (d, 1H), 5.14 (s, 2H), 4.99-4.88 (m, 1H), 4.72 (s, 2H), 4.35-4.20 (m, 1H), 4.00 (dd, 2H), 3.65 (s, 3H), 3.60 (d, 3H), 3.31 (s, 1H), 2.79 (d, 2H), 2.46-2.29 (m, 3H), 1.57 (d, 3H).

MS(ESI) m/z 784.6 (MH⁺)

Example 7

Synthesis of (R)—N-(3-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-phenylethyl)amino)propyl)-N-hydroxyformamide (32)

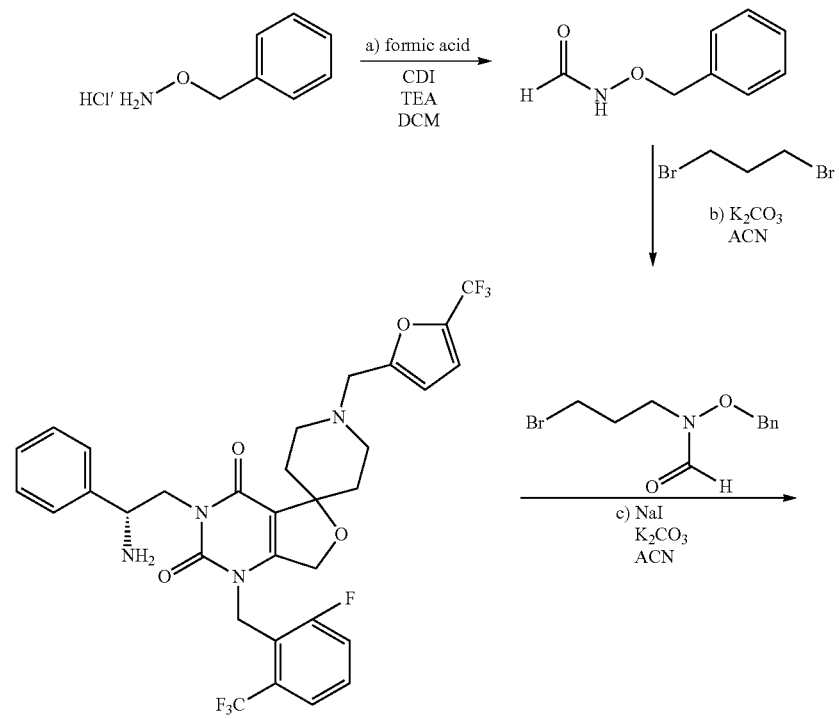

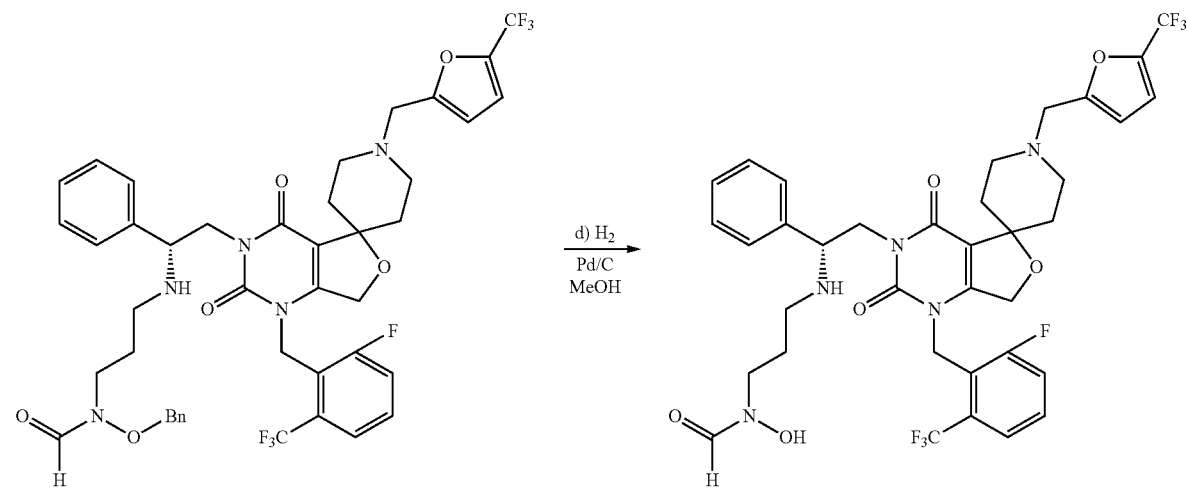

Step A. Preparation of N-(benzyloxy)formamide

A solution prepared by adding formic acid (0.24 mL, 6.26 mmol) to DCM (18.9 mL) was added with CDI (1.01 g, 6.26 mmol), followed by stirring for 30 min at room temperature. O-benzylhydroxyamine.HCl (1 g, 6.26 mmol), TEA (0.87 mL, 6.26 mmol) and DCM (2 mL) were added to the reaction solution, followed by stirring for 3.5 hrs at room temperature. The resulting solution was washed with 1N HCl. The organic layer was dried over MgSO$_4$, concentrated, and purified by MPLC (methanol/DCM=1/191~1/24) to obtain the title compound as clear liquid (628.8 mg, yield: 66%).

$^1$H NMR (300 MHz, CDCl$_3$) δ 8.33 (s, 1H), 7.96 (s, 1H), 7.40 (s, 5H), 4.96-4.85 (s, 2H)

Step B. Preparation of N-(benzyloxy)-N-(3-bromopropyl)formamide

A solution prepared by adding 1,3-dibromopropane (0.635 mL, 6.26 mmol) to ACN (13.6 mL) was added with K$_2$CO$_3$ (649.6 mg, 4.7 mmol), followed by stirring. N-(benzyloxy)formamide (473.7 mg, 3.13 mmol) obtained in Step A and ACN (2 mL) were slowly added to the reaction solution, followed by stirring for 14 hrs at 60° C. The resulting solution was cooled down to room temperature. Water (5 mL) was added to the reaction solution, and the solution was extracted with DCM. The organic layer was dried over MgSO$_4$, concentrated, and purified by MPLC (EA/hexane=0/100~1/4) to obtain the title compound as clear oil (303.8 mg, yield: 36%).

$^1$H NMR (300 MHz, CDCl$_3$) δ 8.22 (s, 1H), 7.37 (d, 5H), 4.89 (d, 2H), 3.73 (s, 2H), 3.42 (s, 2H), 2.26-2.05 (m, 2H)

Step C. Preparation of (R)—N-(benzyloxy)-N-(3-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-phenylethyl)amino)propyl)formamide (31-1)

The procedure of Step A of Example 1 was repeated using (R)-3-(2-amino-2-phenylethyl)-1-(2- fluoro-6-(trifluoromethyl)benzyl)-1'-((5-(trifluoromethyl)furan-2-yl)methyl)-1H-spiro[furo[3,4-d]pyrimidine-5,4'-piperidine]-2,4(3H,7H)-dione (28) (620 mg, 0.93 mmol) and N-(benzyloxy)-N-(3-bromopropyl)formamide prepared in Step B (303.8 mg, 1.12 mmol) to obtain the title compound as white foam (31) (165.9 mg, yield: 21%).

Step D. Preparation of (R)—N-(3-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-phenylethyl)amino)propyl)-N-hydroxyformamide (32)

A solution prepared by adding (R)—N-(benzyloxy)-N-(3-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-phenylethyl)amino)propyl)formamide (31-1) (165.9 mg, 0.19 mmol) prepared in Step C to MeOH (1 mL) was added with 10% Pd/C (degussa type, 332.2 mg, 20% wt), and subjected to hydrogen gas bubbling. A balloon filled with hydrogen gas was attached to the container, and the solution was stirred for 6 hrs at room temperature. The resulting solution was filtered through a Celite pad, concentrated, and purified by MPLC (methanol/DCM=1/49~3/7) to obtain the title compound as white foam (32) (38.3 mg, yield: 26%).

$^1$H NMR (300 MHz, CDCl$_3$) δ 7.55 (d, 2H), 7.47 (dd, 1H), 7.37 (t, 3H), 7.29 (d, 2H), 6.71 (d, 1H), 6.28 (d, 1H), 5.15 (dd, 2H), 4.89 (dd, 1H), 4.83-4.64 (m, 3H), 4.11 (dd, 1H), 3.61 (s, 2H), 3.51 (d, 2H), 3.47 (d, 1H), 3.41-3.24 (m, 1H), 2.79 (d, 2H), 2.63-2.49 (m, 1H), 2.47-2.22 (m, 4H), 2.03 (d, 1H), 1.84 (d, 2H), 1.67 (d, 2H).

Example 8

Synthesis of 4-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-(6-methylpyridin-2-yl)ethyl)amino)butanoic acid (36)

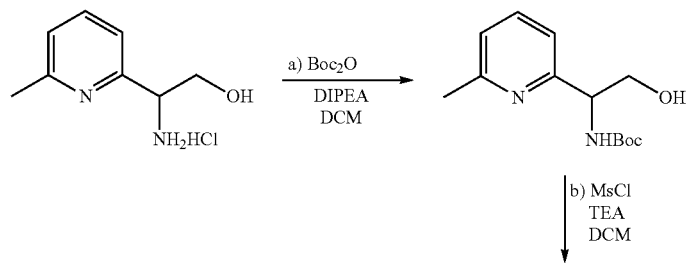

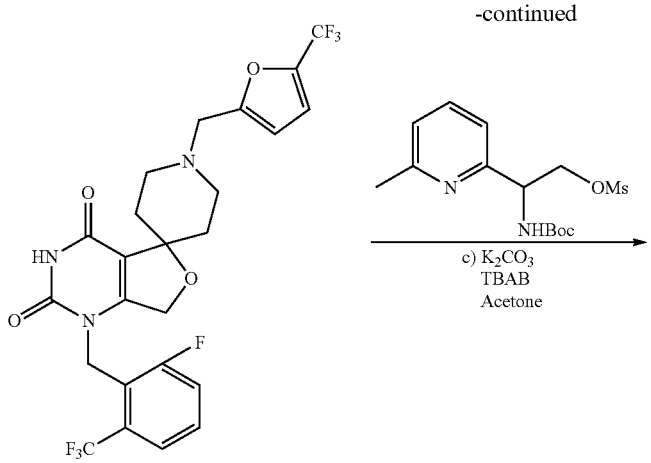

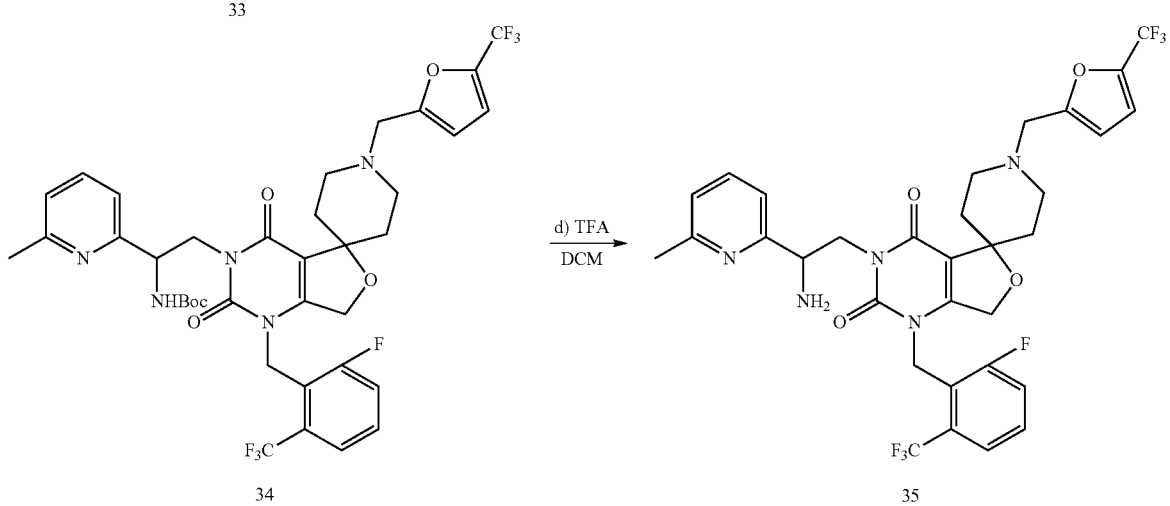

Step A. Preparation of tert-butyl (2-hydroxy-1-(6-methylpyridin-2-yl)ethyl)carbamate A solution prepared by adding 2-amino-2-(6-methyl(2-pyridyl))ethan-1-ol hydrochloride (200 mg, 1.06 mmol) to DCM (3.53 mL) was added with DIPEA (0.37 mL, 2.12 mmol), and stirred, followed by adding Boc-anhydride (255.3 mg, 1.17 mmol) thereto. The resulting mixture was stirred for 21 hrs at room temperature. The mixture was added with distilled water (5 mL), and extracted with DCM. The organic layer was dried over MgSO$_4$, concentrated, and purified by MPLC (ethyl acetate/hexane=1/9~2/3) to obtain the title compound as white solid (205.3 mg, yield: 77%).

$^1$H NMR (300 MHz, CDCl$_3$) δ 7.58 (t, 1H), 7.16 (d, 1H), 7.08 (d, 1H), 5.88 (s, 1H), 4.79 (s, 1H), 4.39 (s, 1H), 4.09-3.97 (m, 1H), 3.91 (s, 1H), 2.53 (s, 3H), 1.58 (s, 1H), 1.45 (s, 9H).

Step B. Preparation of 2-((tert-butoxycarbonyl)amino)-2-(6-methylpyridin-2-yl)ethyl methanesulfonate A solution prepared by adding tert-butyl (2-hydroxy-1-(6-methylpyridin-2-yl)ethyl)carbamate (205.3 mg, 0.81 mmol) obtained in Step A to DCM (2.7 mL) was added with TEA (0.13 mL, 0.97 mmol), and stirred, followed by adding MsCl (68.9 μL, 0.89 mmol) thereto and stirring for 1 hr at room temperature. A saturated NaHCO$_3$ solution was added to the reaction solution and the mixture was extracted with DCM. The organic layer was dried over MgSO$_4$, and concentrated to obtain the title compound as clear oil (279.6 mg, yield: 104%).

$^1$H NMR (300 MHz, CDCl$_3$) δ 7.57 (t, 1H), 7.10 (t, 2H), 5.85 (s, 1H), 5.04 (s, 1H), 4.57 (dd, 1H), 4.45 (d, 1H), 2.89 (s, 3H), 2.54 (s, 3H), 1.47 (s, 9H).

Step C. Preparation of tert-butyl (2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-(6-methylpyridin-2-yl)ethyl)carbamate (34)

The procedure of Example 3 for preparing compound 23 of Example 3 (Step I of Example 3) was repeated using 1-(2-fluoro-6-(trifluoromethyl)benzyl)-1'-((5-(trifluoromethyl)furan-2-yl)methyl)-1H-spiro[furo[3,4-d]pyrimidine-5,4'-piperidine]-2,4(3H,7H)-dione (33) (100 mg, 0.18 mmol) prepared in Step B to obtain the title compound as white foam (137.2 mg, yield: 97%).

Step D. Preparation of 3-(2-amino-2-(6-methylpyridin-2-yl)ethyl)-1-(2-fluoro-6-(trifluoromethyl)benzyl)-1'-((5-(trifluoromethyl)furan-2-yl)methyl)-1H-spiro[furo[3,4-d]pyrimidine-5,4'-piperidine]-2,4(3H,7H)-dione (35)

The procedure of Example 3 for preparing compound 26 of Example 3 (Step L of Example 3) was repeated using tert-butyl (2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-(6-methylpyridin-2-yl)ethyl)carbamate (34) (137.2 mg, 0.175 mmol) prepared in Step C to obtain the title compound as white foam (75.3 mg, yield: 63%).

Step E. Preparation of 4-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidin-5,4'-piperidin]-3(2H,4H,7H)-yl)-1-(6-methylpyridin-2-yl)ethyl)amino)butanoic acid (36)

The procedure of Example 2 for preparing compound 10 (method 1 of Example 2) was repeated using 3-(2-amino-2-(6-methylpyridin-2-yl)ethyl)-1-(2-fluoro-6-(trifluoromethyl)benzyl)-1'-((5-(trifluoromethyl)furan-2-yl)methyl)-1H-spiro[furo[3,4-d]pyrimidine-5,4'-piperidine]-2,4(3H,7H)-dione (35) (65.6 mg, 0.096 mmol) prepared in Step D to obtain the title compound as white foam (46.0 mg, yield: 62%).

MS(ESI) m/z 768.4 (MH+)

Examples 8-1 and 8-2

The compounds of Examples 8-1 and 8-2 were prepared in the same manner as described in Example 8, except for using each compound comprising the corresponding $R_{10}$ group shown in Table 5 below instead of 2-amino-2-(6-methyl(2-pyridyl))ethan-1-ol hydrochloride.

TABLE 5

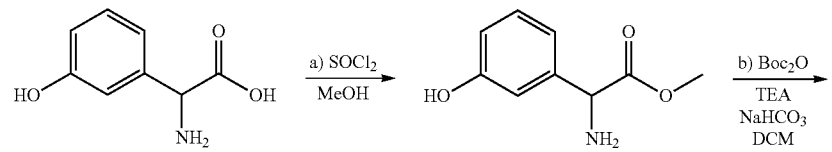

| Example | —$R_{10}$ | M.W. | Mass |
|---|---|---|---|
| 8-1 | (2,5-dimethylthiophene) | 772.73 | 773.0 |
| 8-2 | (2,5-dimethylfuran) | 756.66 | 757.0 |

Example 9

Synthesis of 4-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-(3-hydroxyphenyl)ethyl)amino)butanoic acid (46)

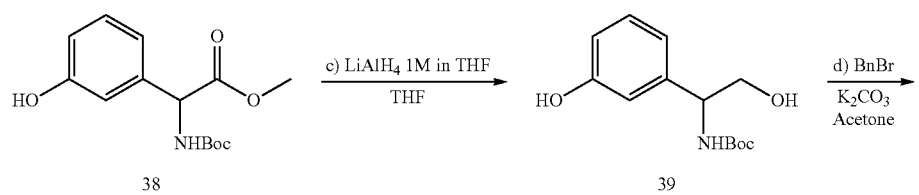

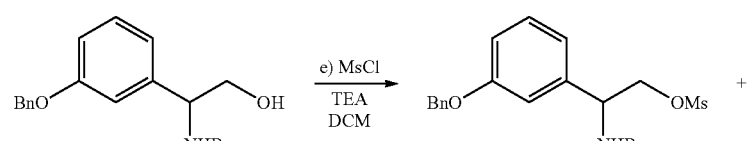

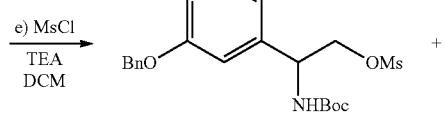

-continued
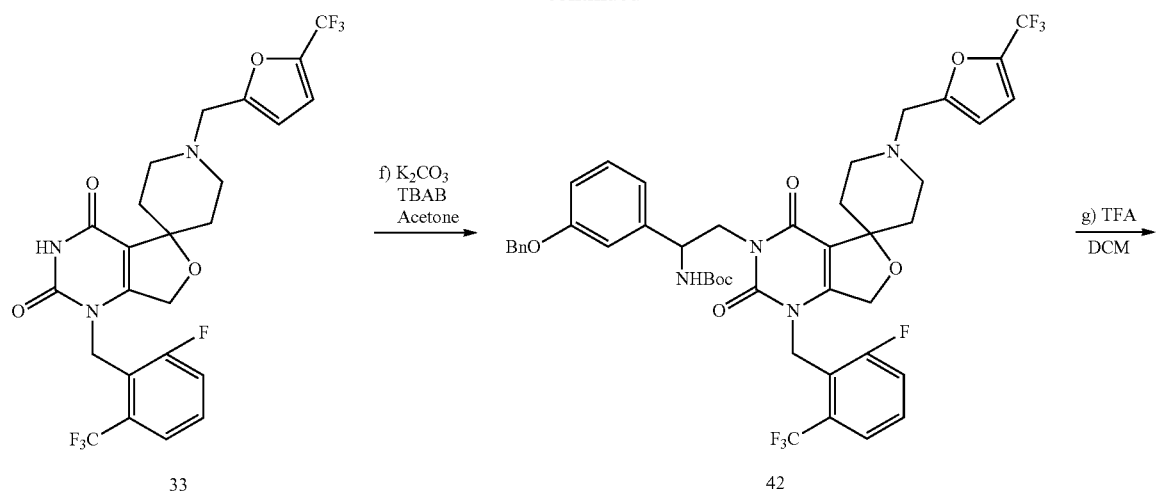
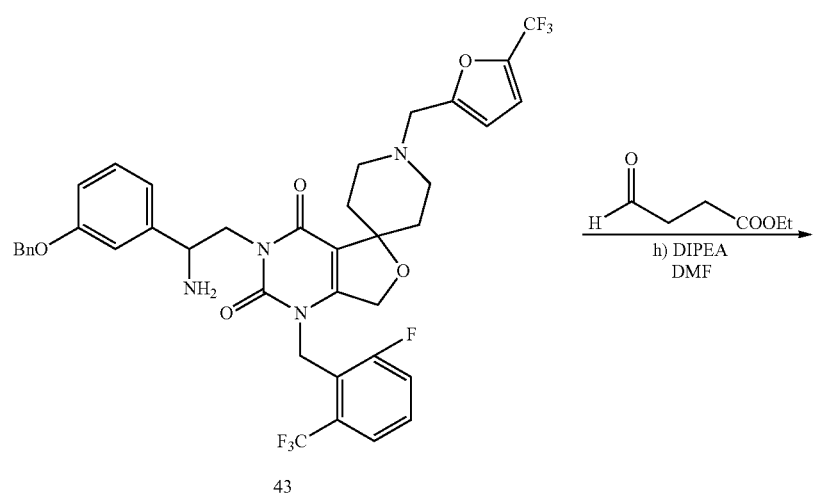
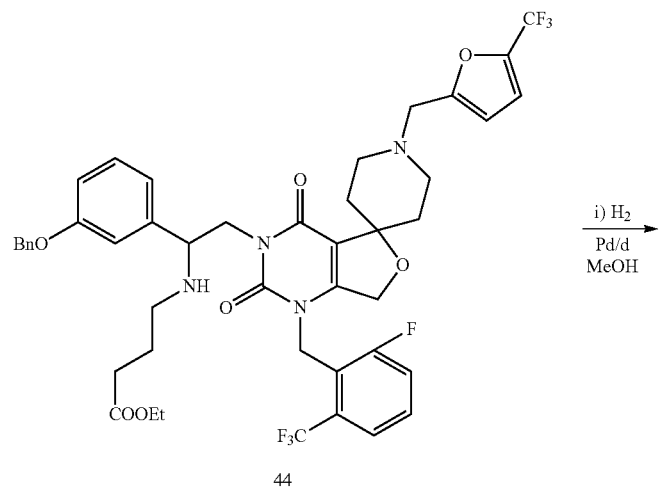

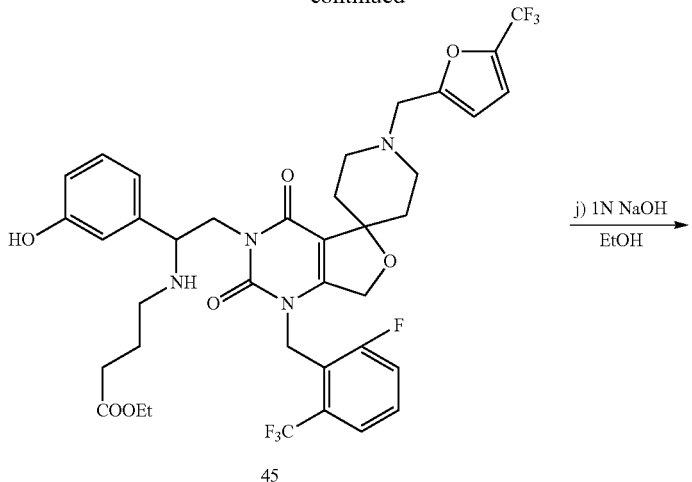

45

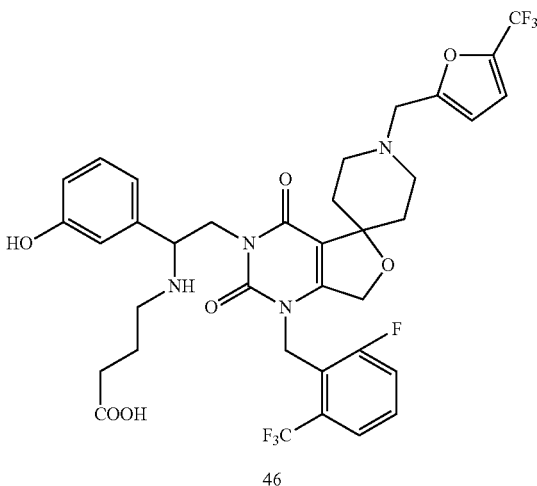

46

Steps A & B. Preparation of methyl 2-((tert-butoxycarbonyl)amino)-2-(3-hydroxyphenyl)acetate (38)

A solution prepared by adding DL-3-hydroxyphenylglycine (1 g, 5.98 mmol) to MeOH (12 mL) was added with thionyl chloride (0.52 mL, 7.18 mmol), followed by stirring for 2 hrs at 80° C. The resulting solution was cooled down to room temperature, and concentrated. The concentrate was diluted with DCM (15 mL), added with NaHCO₃ (753 mg, 8.97 mmol) and TEA (0.92 mL, 6.58 mmol) and stirred, followed by adding Boc₂O (1.44 g, 6.58 mmol) thereto and stirring for 21 hrs at room temperature. The reaction solution was neutralized with a saturated NH₄Cl solution and extracted with DCM. The organic layer was dried over MgSO₄, concentrated, and purified by MPLC (methanol/DCM=1/191~1/24) to obtain the title compound as ivory foam (1.4 g, yield: 83%).

$^1$H NMR (300 MHz, CDCl₃) δ 7.21 (t, 1H), 6.92 (d, 1H), 6.84 (d, 1H), 6.81-6.74 (m, 1H), 5.55 (s, 1H), 5.33-5.20 (m, 1H), 5.16 (s, 1H), 3.72 (s, 3H), 1.45 (d, 9H).

Step C. Preparation of tert-butyl (2-hydroxy-1-(3-hydroxyphenyl)ethyl)carbamate (39)

A solution prepared by adding methyl 2-((tert-butoxycarbonyl)amino)-2-(3-hydroxyphenyl)acetate (38) (1.4 g, 4.98 mmol) obtained above to THF (12 mL) was cooled in an ice bath, and 1M LAH (lithium aluminium hydride) in THF (4.98 mL) was slowly added thereto. The mixture was warmed to room temperature, and stirred for 1 hr. The resulting solution was cooled in an ice bath and then a saturated NH₄Cl solution was slowly added thereto until no more gas was evolved. The reaction solution was filtered through a Celite pad, added with 2N HCl to adjust pH 1, and extracted with DCM. The organic layer was dried over MgSO₄, concentrated, and purified by MPLC (methanol/DCM=1/191~1/24) to obtain the title compound as white foam (1.29 g, yield: 102%).

$^1$H NMR (300 MHz, CDCl₃) δ 7.23-7.14 (m, 1H), 6.82 (d, 1H), 6.77-6.67 (m, 2H), 6.12 (s, 1H), 5.32 (d, 1H), 4.74 (d, 1H), 3.85 (dd, 2H), 2.48 (s, 1H), 1.44 (s, 9H).

Step D. Preparation of tert-butyl (1-(3-(benzyloxy)phenyl)-2-hydroxyethyl)carbamate (40)

A solution prepared by adding tert-butyl(2-hydroxy-1-(3-hydroxyphenyl)ethyl)carbamate (500 mg, 1.97 mmol) obtained in Step C to acetone (19.7 mL) was added with K₂CO₃ (407.7 mg, 2.95 mmol), followed by stirring. Benzyl bromide (0.23 mL, 1.97 mmol) was added thereto, followed by stirring for 19 hrs at room temperature. The resulting solution was heated to 60° C., stirred for 1 hr and cooled down to room temperature. Then, the solution was filtered, washed with acetone, concentrated, and purified by MPLC (methanol/DCM=1/191~1/24) to obtain the title compound as white foam (225.1 mg, yield: 33.3%).

$^1$H NMR (300 MHz, CDCl$_3$) δ 7.46-7.40 (m, 2H), 7.38 (d, 1H), 7.37-7.33 (m, 1H), 7.31 (d, 1H), 7.27 (s, 1H), 6.94-6.89 (m, 2H), 6.88 (d, 1H), 5.19 (s, 1H), 5.06 (s, 2H), 4.75 (s, 1H), 3.90-3.73 (m, 2H), 2.19 (d, 1H), 1.43 (s, 9H).

Step E. Preparation of 2-(3-(benzyloxy)phenyl)-2-((tert-butoxycarbonyl)amino)ethyl methanesulfonate (41)

The procedure of Step A of Example 4 was repeated using tert-butyl (1-(3-(benzyloxy)phenyl)-2-hydroxyethyl)carbamate (40) (112.5 mg, 0.33 mmol) prepared in Step D to obtain the title compound as a crude product.

Step F. Preparation of tert-butyl (1-(3-(benzyloxy)phenyl)-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)carbamate (42)

The procedure of Step I of Example 3 was repeated using 2-(3-(benzyloxy)phenyl)-2-((tert-butoxycarbonyl)amino)ethyl methanesulfonate (41) (120.4 mg, 0.22 mmol) prepared in Step E to obtain the title compound as white foam (158 mg, yield: 82%).

Step G. Preparation of 3-(2-amino-2-(3-(benzyloxy)phenyl)ethyl)-1-(2-fluoro-6-(trifluoromethyl)benzyl)-1'-((5-(trifluoromethyl)furan-2-yl)methyl)-1H-spiro[furo[3,4-d]pyrimidine-5,4'-piperidine]-2,4(3H,7H)-dione (43)

The procedure of Step L of Example 3 was repeated using tert-butyl (1-(3-(benzyloxy)phenyl)-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)carbamate (42) (158.2 mg, 0.18 mmol) prepared in Step F to obtain the title compound as white foam (99.1 mg, yield: 71%).

Step H. Preparation of ethyl 4-((1-(3-(benzyloxy)phenyl)-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)amino)butanoate (44)

The procedure of Step A in Method 2 of Example 2 was repeated using 3-(2-amino-2-(3-(benzyloxy)phenyl)ethyl)-1-(2-fluoro-6-(trifluoromethyl)benzyl)-1'-((5-(trifluoromethyl)furan-2-yl)methyl)-1H-spiro[furo[3,4-d]pyrimidine-5,4'-piperidine]-2,4(3H,7H)-dione (45) (50.1 mg, 0.065 mmol) prepared in Step G to obtain the title compound as white foam (33.0 mg, yield: 57%).

Step I. Preparation of ethyl 4-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-(3-hydroxyphenyl)ethyl)amino)butanoate (45)

A solution prepared by adding ethyl 4-((1-(3-(benzyloxy)phenyl)-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)amino)butanoate (44) (33.0 mg, 0.037 mmol) prepared in Step H to methanol (1 mL) was added with Pd/C (degussa type, 4.95 mg, 15% wt), and subjected hydrogen gas bubbling for 10 min. A balloon filled with hydrogen gas was attached to the container, and the solution was stirred for 1.5 hrs at room temperature. The resulting solution was filtered through a Celite pad, concentrated, and purified by MPLC (methanol/DCM=1/99~1/19) to obtain the title compound as white foam (25.3 mg, yield: 86%).

$^1$H NMR (300 MHz, CDCl$_3$) δ 7.54 (d, 1H), 7.45 (dd, 1H), 7.30 (d, 1H), 7.17 (t, 1H), 6.86 (d, 2H), 6.75-6.65 (m, 2H), 6.30 (d, 1H), 5.14 (d, 1H), 5.00 (d, 1H), 4.74-4.59 (m, 2H), 4.06 (d, 2H), 3.61 (s, 2H), 2.77 (s, 2H), 2.53-2.29 (m, 6H), 2.25 (t, 2H), 1.64 (d, 2H), 1.60-1.45 (m, 2H), 1.19 (t, 3H).

Step J. Preparation of 4-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-(3-hydroxyphenyl)ethyl)amino)butanoic acid (46)

The procedure of Step B in Method 2 of Example 2 was repeated using ethyl 4-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-(3-hydroxyphenyl)ethyl)amino)butanoate (25.3 mg, 0.032 mmol) prepared in Step I to obtain the title compound as white foam (14.3 mg, yield: 58%).

MS(ESI) m/z 769.2 (MH$^+$)

Example 10

Synthesis of (R)-4-((2-(1'-((5-bromofuran-2-yl)methyl)-1-(2-fluoro-6-(trifluoromethyl)benzyl)-2,4-dioxo-1H-spiro[furo[3,4-d]pyrimidine-5,4'-piperidin]-3(2H,4H,7H)-yl)-1-phenylethyl)amino)butanoic acid (49)

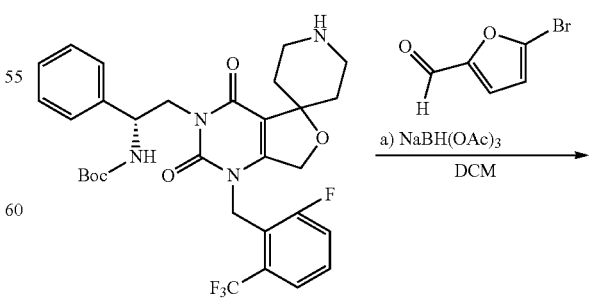

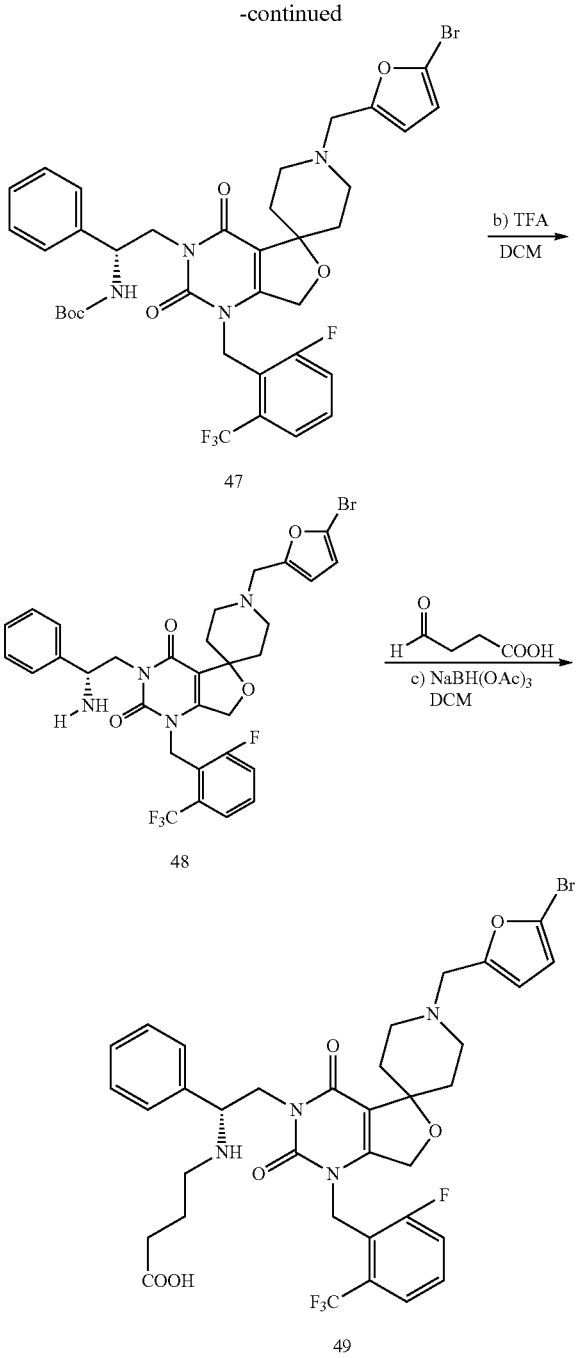

with a saturated NaHCO₃ solution, and extracted with DCM. The organic layer was dried over MgSO₄, concentrated, and purified by MPLC (methanol/DCM=1/191~1/24) to obtain the title compound as light reddish-white foam (62.5 mg, yield: 50%).

¹H NMR (300 MHz, CDCl₃) δ 7.56 (d, 1H), 7.47 (dd, 1H), 7.40-7.33 (m, 2H), 7.31 (d, 2H), 7.27 (s, 1H), 7.24 (s, 1H), 6.23 (d, 1H), 6.19 (d, 1H), 5.64 (s, 1H), 5.25 (d, 1H), 5.05 (d, 1H), 4.69 (d, 2H), 4.26 (d, 1H), 4.01 (d, 1H), 3.56 (s, 2H), 2.80 (d, 2H), 2.39 (t, 4H), 1.55 (d, 3H), 1.37 (s, 9H).

Step B. Preparation of (R)-3-(2-amino-2-phenylethyl)-1'-((5-bromofuran-2-yl)methyl)-1-(2-fluoro-6-(trifluoromethyl)benzyl)-1H-spiro[furo[3,4-d]pyrimidine-5,4'-piperidine]-2,4(3H,7H)-dione (48)

The procedure of Example 3 for preparing compound 26 of Example 3 was repeated using (R)-tert-butyl(2-(1'-((5-bromofuran-2-yl)methyl)-1-(2-fluoro-6-(trifluoromethyl)benzyl)-2,4-dioxo-1H-spiro[furo[3,4-d]pyrimidine-5,4'-piperidin]-3(2H,4H,7H)-yl)-1-phenylethyl)carbamate (47) (62.5 mg, 0.08 mmol) to obtain the title compound as white foam (34.8 mg, yield: 64.2%).

Step C. Preparation of (R)-4-((2-(1'-((5-bromofuran-2-yl)methyl)-1-(2-fluoro-6-(trifluoromethyl)benzyl)-2,4-dioxo-1H-spiro[furo[3,4-d]pyrimidine-5,4'-piperidin]-3(2H,4H,7H)-yl)-1-phenylethyl)amino)butanoic acid (49)

The procedure of Example 2 for preparing compound 10 (Method 1 of Example) 2 was repeated using (R)-3-(2-amino-2-phenylethyl)-1'-((5-bromofuran-2-yl)methyl)-1-(2-fluoro-6-(trifluoromethyl)benzyl)-1H-spiro[furo[3,4-d]pyrimidine-5,4'-piperidine]-2,4(3H,7H)-dione (48) (34.8 mg, 0.051 mmol) to obtain the title compound as white foam (16.4 mg, yield: 42%).

MS(ESI) m/z 763.1 (MH⁺)

Examples 10-1 and 10-2

The compounds of Examples 10-1 and 10-2 were prepared in the same manner as described in Example 10, except for using each aldehyde compound comprising the corresponding R₄ group shown in Table 6 below instead of 5-bromo-2-furaldehyde.

Step A. Preparation of (R)-tert-butyl (2-(1'-((5-bromofuran-2-yl)methyl)-1-(2-fluoro-6-(trifluoromethyl)benzyl)-2,4-dioxo-1H-spiro[furo[3,4-d]pyrimidine-5,4'-piperidin]-3(2H,4H,7H)-yl)-1-phenylethyl)carbamate (47)

A solution prepared by adding (R)-tert-butyl (2-(1-(2-fluoro-6-(trifluoromethyl)benzyl)-2,4-dioxo-1H-spiro[furo[3,4-d]pyrimidine-5,4'-piperidin]-3(2H,4H,7H)-yl)-1-phenylethyl)carbamate (100 mg, 0.16 mmol) to MeOH (1 mL) was added with 5-bromo-2-furaldehyde and NaBH(OAc)₃ sequentially, followed by stirring for 15 hrs at room temperature. The resulting solution was concentrated, added

TABLE 6

| Example | —R₄ | M.W. | Mass |
|---|---|---|---|
| 10-1 | | 708.70 | 709.1 |
| 10-2 | | 734.74 | 735.3 |

Example 11
Synthesis of (R)-4-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-phenylethyl)amino)-N-hydroxybutanamide (52)
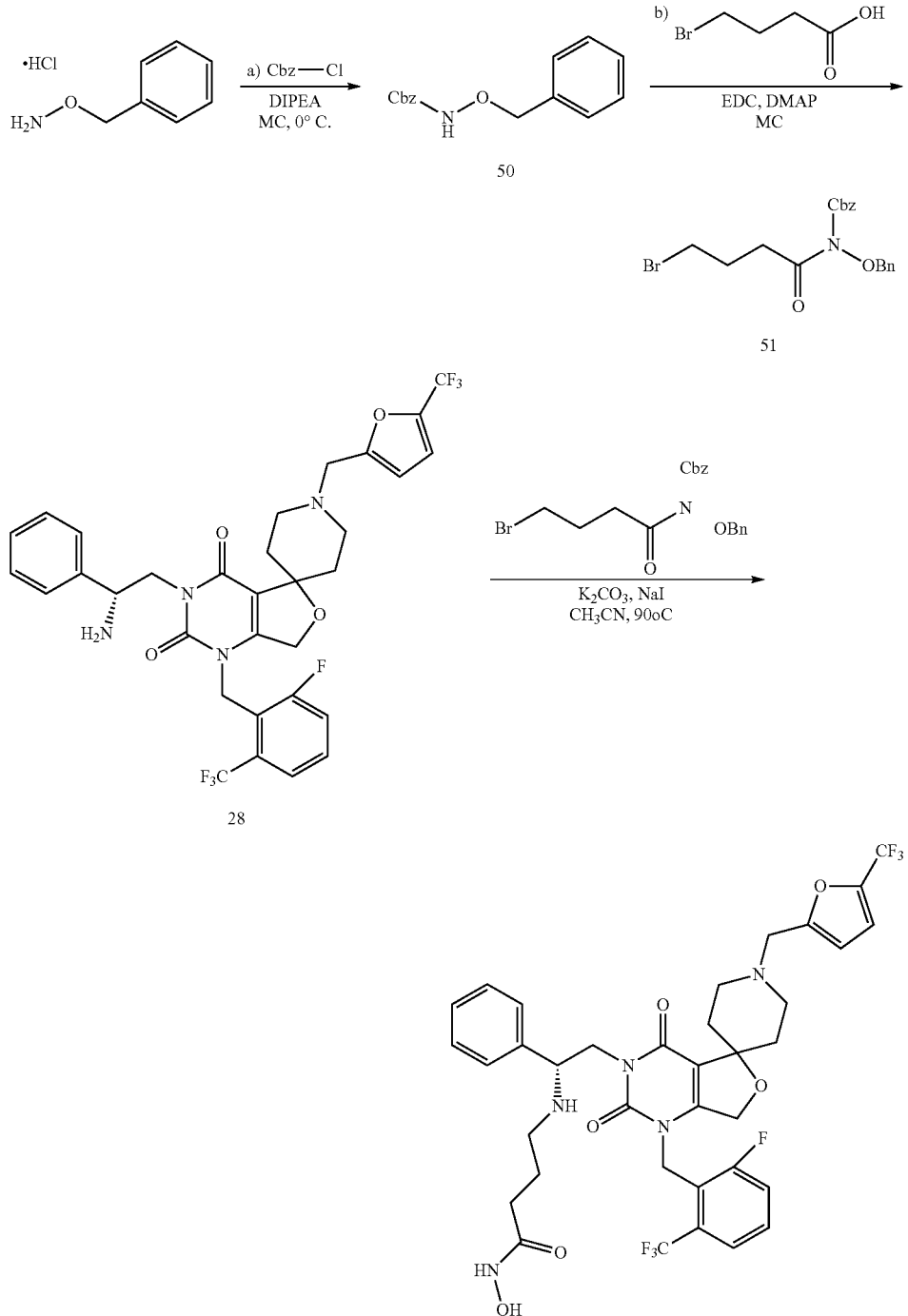

Step A. Preparation of benzyloxyl carbamic acid benzyl ester (50)

A solution prepared by adding O-benzyl-hydroxylamine hydrochloride (1.0 g, 6.27 mmol) and DIPEA (2.7 mL, 15.7 mmol) to $CH_2Cl_2$ (15 mL) was added with benzyl chloroformate (1.0 mL, 7.52 mol) at 0° C. The resulting solution was stirred for 1 hr, diluted with water, and extracted with $CH_2Cl_2$. The organic layer was collected, dried over $MgSO_4$, filtered, and concentrated under reduced pressure to obtain the title compound as liquid (1.93 g, yield: >100%).

$^1$H NMR (600 MHz, $CDCl_3$) δ 4.87 (2H, s), 5.18 (2H, s), 7.29-7.41 (10H, m)

Step B. Preparation of N-(benzyloxyl)-(4-bromo-butanoyl)-carbamic acid benzyl ester (51)

A solution prepared by adding benzyloxyl carbamic acid benzyl ester (50) (463 mg, 1.80 mmol) obtained in Step A, 4-bromobutanoic acid (300 mg, 1.80 mmol) and 4-dimethylaminopyridine (DMAP, 22 mg, 0.18 mmol) to $CH_2Cl_2$ (12 mL) was added with EDC (345 mg, 1.80 mmol). The resulting solution was stirred for 2.5 days, diluted with water and extracted with $CH_2Cl_2$. The organic layer was collected, washed with saline, dried over $MgSO_4$, filtered, and concentrated under reduced pressure to obtain the title compound as liquid (250.6 mg, yield: 34%).

$^1$H NMR (600 MHz, $CDCl_3$) δ 2.21 (2H, m), 2.97 (2H, t), 3.48 (2H, t), 4.91 (2H, s), 5.28 (2H, s), 7.29-7.41 (10H, m)

Step C. Preparation of (R)-4-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-phenylethyl)amino)-N-hydroxybutanamide (52)

N-(benzyloxyl)-(4-bromo-butanoyl)-carbamic acid benzyl ester (51) (148.2 mg, 0.22 mmol) was dissolved in acetonitrile (2.5 mL), and then NaI (82.4 mg, 0.55 mmol), $K_2CO_3$ (76.0 mg, 0.55 mmol) and N-(benzyloxyl)-(4-bromo-butanoyl)-carbamic acid benzyl ester (108.4 mg, 0.27 mmol) were added thereto in sequence. The mixture was stirred under a reflux condition for 17 hrs, cooled down to room temperature, diluted with a saturated aqueous solution of ammonium chloride, and extracted with $CH_2Cl_2$. The organic layer was dried over $MgSO_4$, filtered, and concentrated under reduced pressure. The residue was purified by silica gel chromatography (eluent: dichloromethane/methanol=98/2~95/5), and dried under vacuum to yield the title compound as white foam (57.2 mg, yield: 34%).

$^1$H NMR (300 MHz, $CDCl_3$) δ 1.38-1.51 (4H, m), 1.77 (1H, bs), 2.03 (2H, m), 2.06-2.70 (7H, m), 2.73 (2H, m), 3.58 (2H, s), 4.13 (2H, m), 4.22 (1H, dd), 4.60 (2H, s), 5.09 (2H, m), 5.20 (1H, m), 6.26 (1H, d), 6.71 (1H, d), 7.25-7.42 (7H, m), 7.53 (1H, d)

Example 12

Synthesis of (R)-2-(4-(1-amino-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)phenoxy)acetic acid (60)

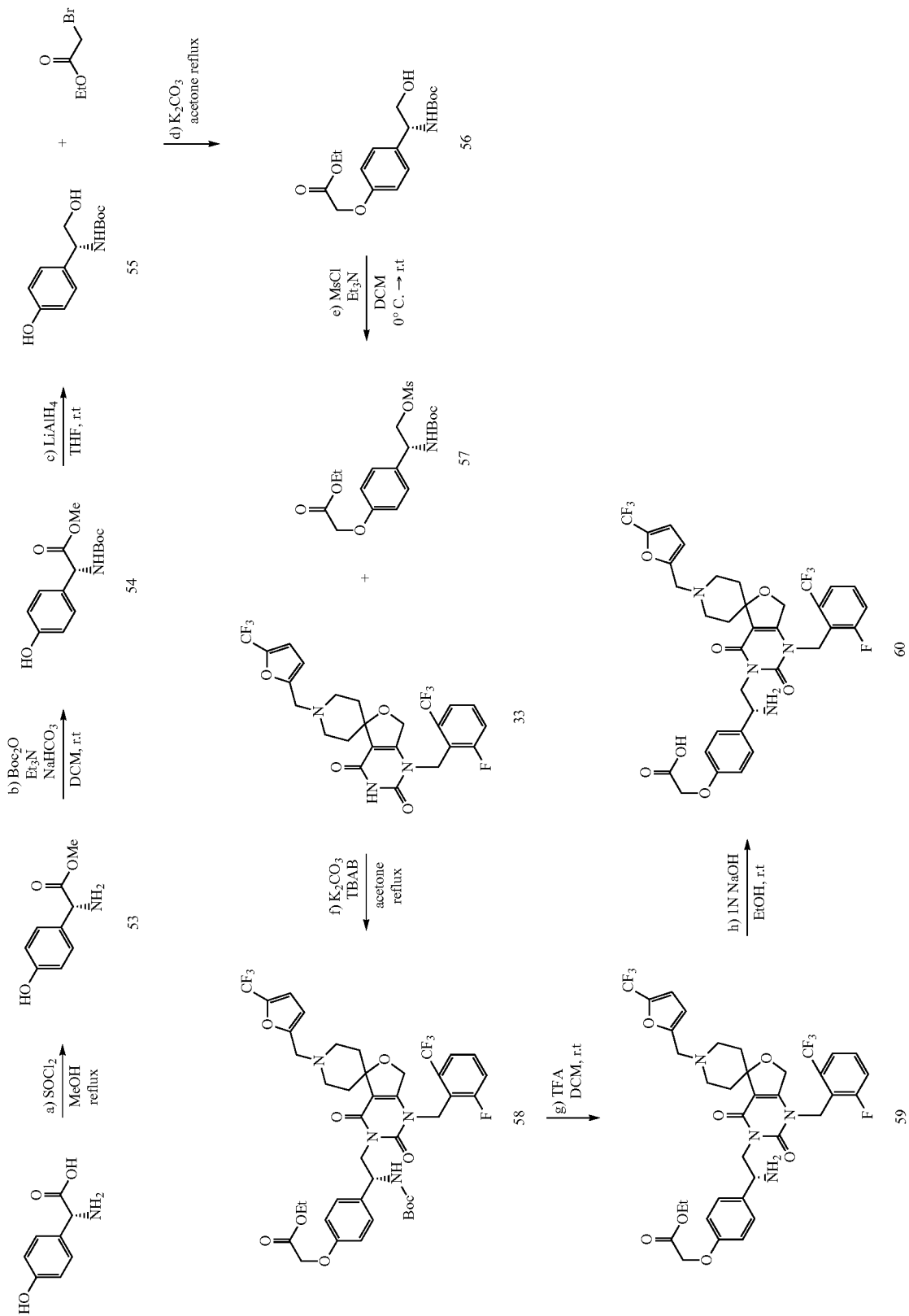

Step A. Preparation of (R)-methyl 2-amino-2-(4-hydroxyphenyl)acetate (53)

(R)-2-amino-2-(4-hydroxyphenyl)acetic acid (7.10 g, 42.5 mmol) was dissolved in methanol (85 mL), stirred for 10 min in an ice bath, and thionyl chloride (3.72 mL, 51.0 mmol) was slowly added thereto. The resulting mixture was refluxed under a nitrogen atmosphere for 2 hrs, followed by cooling down to room temperature. The reaction solution was concentrated under reduced pressure and the residue obtained was used in the next step without further purification.

$^1$H NMR (600 MHz, DMSO-$d_6$) δ 2.18 (2H, br), 3.53 (3H, s), 4.36 (1H, s), 6.66 (2H, d), 7.12 (2H, d), 9.33 (1H, s)

Step B. Preparation of (R)-methyl 2-((tert-butoxycarbonyl)amino)-2-(4-hydroxyphenyl)acetate (54)

(R)-methyl 2-amino-2-(4-hydroxyphenyl)acetate (53) obtained in Step A was diluted with dichloromethane (100 mL) and methanol (3 mL), and slowly added with sodium bicarbonate (5.36 g, 63.8 mmol), triethylamine (6.60 mL, 46.7 mmol), and di-tert-butyl dicarbonate (10.2 g, 46.7 mmol) at room temperature in sequence. The reaction solution was stirred for 2 hrs at the same temperature, and slowly added with a saturated aqueous solution of ammonium chloride (100 mL). The aqueous layer was extracted twice with ethyl acetate. The organic layer was collected, dried over MgSO$_4$, filtered, and concentrated under reduced pressure. The concentrate was recrystallized (Hex:EA=5:1), and dried under vacuum to obtain ivory solid (11.1 g, yield: 93%).

$^1$H NMR (600 MHz, DMSO-$d_6$) δ 1.42 (9H, s), 3.70 (3H, s), 5.21-5.57 (1H, m), 6.04 (1H, s), 6.71 (2H, d), 7.16 (2H, d)

Step C. Preparation of (R)-tert-butyl (2-hydroxy-1-(4-hydroxyphenyl)ethyl)carbamate (55)

(R)-methyl 2-((tert-butoxycarbonyl)amino)-2-(4-hydroxyphenyl)acetate (54) (2.10 g, 7.47 mol) obtained in Step B was added to anhydrous tetrahydrofuran (100 mL), and lithium aluminum tetrahydride (850 mg, 22.4 mmol) was slowly added thereto in small portion at room temperature. The resulting mixture was stirred for 1 hr at room temperature, and distilled water (0.85 mL), an aqueous solution of 2N NaOH (1.70 mL), and distilled water (2.55 mL) were added thereto in sequence. The reaction solution was filtered, and concentrated under reduced pressure. The residue was purified by silica gel chromatography (eluent: dichloromethane/methanol=99/1~90/10), and dried under vacuum to yield the title compound as ivory solid (1.00 g, yield: 53%).

$^1$H NMR (600 MHz, DMSO-$d_6$) δ 1.36 (9H, s), 3.41-3.43 (2H, m), 4.41 (1H, br), 4.69 (1H, t), 6.67 (2H, d), 7.06 (2H, d), 9.21 (1H, s)

Step D. Preparation of (R)-ethyl 2-(4-(1-((tert-butoxycarbonyl)amino)-2-hydroxyethyl)phenoxy)acetate (56)

(R)-tert-butyl (2-hydroxy-1-(4-hydroxyphenyl)ethyl)carbamate (55) (300 mg, 1.18 mmol) obtained in Step C was added to acetone (12 mL), and potassium carbonate (246 mg, 1.48 mmol) and ethyl bromoacetate (0.197 mL, 1.78 mmol) were added thereto at room temperature. The resulting solution was heated to 80° C. and stirred for 15 hrs. The solution was cooled down to room temperature and concentrated under reduced pressure to remove acetone. The residue was diluted with dichloromethane (15 mL), and a saturated aqueous solution of ammonium chloride (15 mL) was added thereto. The aqueous layer was extracted twice with dichloromethane. The organic layer was collected, dried over Na$_2$SO$_4$, filtered, and concentrated under reduced pressure. The residue was purified by silica gel chromatography (eluent: dichloromethane/methanol=99/1~9/1), and dried under vacuum to yield the title compound as ivory solid (380 mg, yield: 95%).

$^1$H NMR (600 MHz, CDCl$_3$) δ 1.30 (3H, t), 1.43 (9H, s), 1.38 (1H, br), 3.81 (2H, s), 4.26 (2H, q), 4.60 (2H, s), 4.72 (1H, s), 5.18 (1H, d), 6.87-6.90 (2H, m), 7.21-7.23 (2H, m)

Step E. Preparation of (R)-2-((tert-butoxycarbonyl)amino)-2-(4-(2-ethylacetoxy)phenyl)ethyl methanesulfonate (57)

(R)-ethyl 2-(4-(1-((tert-butoxycarbonyl)amino)-2-hydroxyethyl)phenoxy)acetate (56) (360 mg, 1.06 mmol) obtained in Step D was added to dichloromethane (5 ml), and then triethylamine (177 µl, 1.17 mmol) and methanesulfonyl chloride (91 µl, 1.27 mmol) were added thereto in sequence. The resulting solution was stirred for 30 min at room temperature, and a saturated aqueous solution of sodium bicarbonate was added thereto. The aqueous layer was extracted twice with dichloromethane. The organic layer was collected, dried over MgSO$_4$, filtered, and concentrated under reduced pressure. The residue obtained was used in the next step without further purification.

Step F. Preparation of (R)-ethyl 2-(4-(1-((tert-butoxycarbonyl)amino)-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)phenoxy)acetate (58)

(R)-2-((tert-butoxycarbonyl)amino)-2-(4-(2-ethylacetoxy)phenyl)ethyl methanesulfonate (57) (crude, 1.06 mmol) obtained in Step E, 1-(2-fluoro-6-(trifluoromethyl)benzyl)-1'-((5-(trifluoromethyl)furan-2-yl)methyl)-1H-spiro[furo[3,4-d]pyrimidine-5,4'-piperidine]-2,4(3H,7H)-dione (33) (387 mg, 0.707 mmol), potassium carbonate (293 mg, 2.12 mmol) and tetrabutylammonium bromide (23 mg, 0.071 mmol) were suspended in acetone (10 ml), heated to 70° C., and stirred for 15 hrs. The reaction solution was cooled down to room temperature, and solids were removed by filtration. The filtrate was concentrated under reduced pressure to remove acetone and diluted with ethyl acetate (20 mL). The resulting solution was washed once with a saturated sodium bicarbonate solution (20 mL), dried over MgSO$_4$, and concentrated under reduced pressure. The residue was purified by silica gel chromatography (eluent: hexane/ethyl acetate=9/1~1/1), and dried under vacuum to yield the title compound as ivory foam (480 mg, yield: 78%).

$^1$H NMR (600 MHz, CDCl$_3$) δ 1.28 (3H, t), 1.34 (9H, s), 1.53-1.59 (2H, m), 2.34-2.43 (4H, m), 2.76-2.80 (2H, m), 3.61 (2H, s), 3.97 (1H, d), 4.24 (1H, q), 4.57 (2H, s), 4.64-4.72 (2H, m), 4.93-4.97 (1H, m), 5.03 (1H, d), 5.22 (1H, d), 5.60 (1H, d), 6.28 (1H, d), 6.71 (1H, d), 6.83-6.86 (2H, m), 7.24-7.28 (3H, m), 7.43-7.47 (1H, m), 7.54 (1H, d)

Step G. Preparation of (R)-ethyl 2-(4-(1-amino-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)phenoxy)acetate (59)

(R)-ethyl 2-(4-(1-((tert-butoxycarbonyl)amino)-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)phenoxy)acetate (58) (470 mg, 0.541 mmol) obtained in Step F was added to dichloromethane (8 mL) and stirred for 3 hrs at room temperature. The reaction solution was neutralized with an aqueous solution of 0.5N HCl, and extracted three times with dichloromethane. The organic layer was dried over $Na_2SO_4$, concentrated, purified by MPLC (eluent: dichloromethane/methanol=99/1~9/1), and dried under vacuum to obtain the title compound as ivory foam (360 mg, yield: 87%).

$^1$H NMR (600 MHz, $CDCl_3$) δ 1.30 (3H, t), 1.52-1.60 (4H, m), 2.32-2.43 (4H, m), 2.76-2.79 (2H, m), 3.60 (2H, s), 4.01 (1H, dd), 4.13 (1H, dd), 4.25-4.31 (3H, m), 4.60 (2H, s), 4.65-4.71 (2H, m), 5.10-5.16 (2H, m), 6.29 (1H, d), 6.71-6.72 (1H, m), 6.84-6.87 (2H, m), 7.27-7.31 (3H, m), 7.45-7.48 (1H, m), 7.56 (1H, d)

Step H. Preparation of (R)-2-(4-(1-amino-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)phenoxy)acetic acid (R)-ethyl 2-(4-(1-amino-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)phenoxy)acetate (59) (100 mg, 0.130 mmol) obtained in Step G was added to ethanol (0.39 mL) together with an aqueous 1N NaOH solution (0.39 mL, 0.39 mmol), followed by stirring for 2 hrs at room temperature. The reaction solution was neutralized using an aqueous solution of 1N HCl (0.3 mL), and concentrated under reduced pressure to remove ethanol therefrom. The aqueous layer was extracted three times with dichloromethane. The organic layer was collected, dried over $Na_2SO_4$, filtered, and concentrated under reduced pressure. The residue was recrystallized, and dried under vacuum to obtain the title compound as ivory solid (70 mg, yield: 73%).

$^1$H NMR (600 MHz, $CDCl_3$) δ 1.42-1.52 (2H, m), 2.02-2.07 (1H, m), 2.11-2.17 (1H, m), 2.24-2.29 (2H, m), 2.68-2.70 (2H, m), 3.36 (2H, br), 3.57-3.63 (2H, m), 3.92 (2H, d), 4.13 (1H, t), 4.30 (2H, s), 4.87-4.92 (2H, m), 4.95-5.01 (2H, m), 6.54 (1H, d), 6.71 (2H, d), 7.12 (2H, d), 7.15-7.16 (1H, m), 7.54-7.60 (2H, m), 7.62-7.64 (1H, m)

MS (ESI) m/z 741.2 (MH$^+$)

Examples 12-1 to 12-3

The compounds of Examples 12-1 to 12-3 were prepared in the same manner as described in Example 12 above, except for using each compound comprising the corresponding $R_5$ group shown in Table 7 below instead of (R)-2-((tert-butoxycarbonyl)amino)-2-(4-(2-ethylacetoxy)phenyl)ethyl methanesulfonate in Step F of Example 12.

TABLE 7

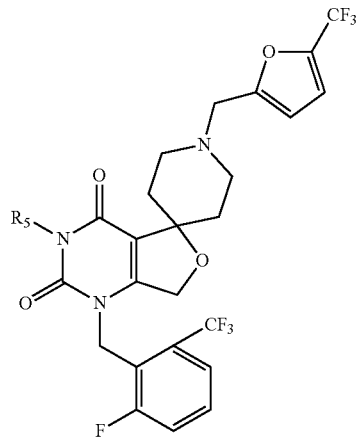

| Example | —$R_5$ | M.W. | Mass |
|---|---|---|---|
| 12-1 | (structure with OH, O, phenyl, $NH_2$) | 768.7 | 769.3 |
| 12-2 | (HO, O, O, phenyl, $NH_2$) | 740.6 | 741.3 |
| 12-3 | (HO, O, O, phenyl, $NH_2$) | 768.7 | 769.1 |

Example 13

Synthesis of 3-((3-(1-amino-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)phenyl)amino)propanoic acid (61)

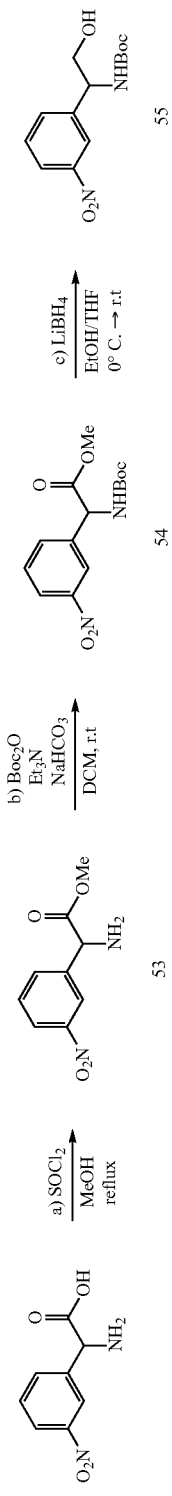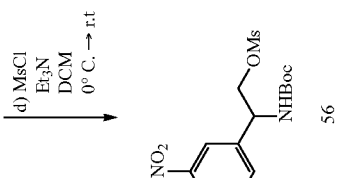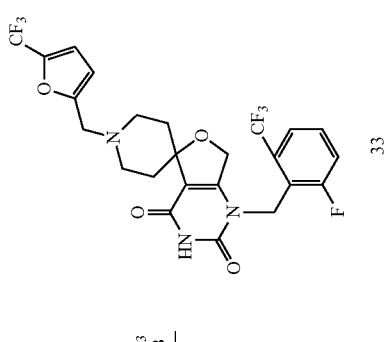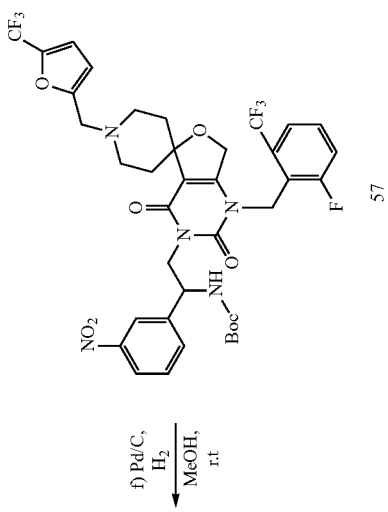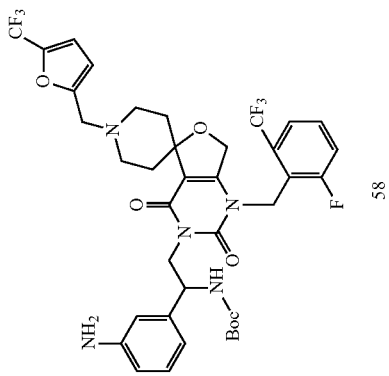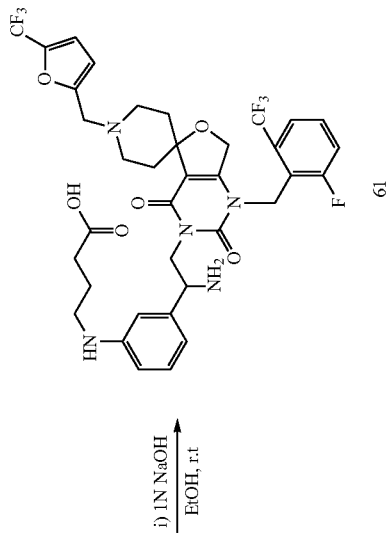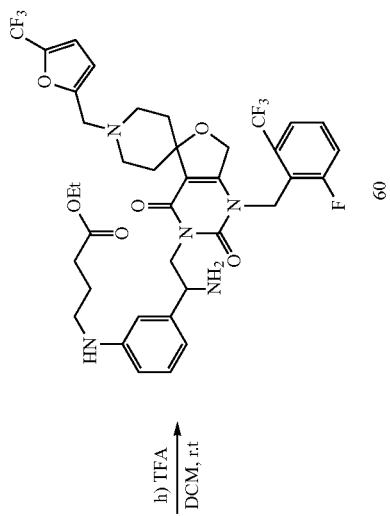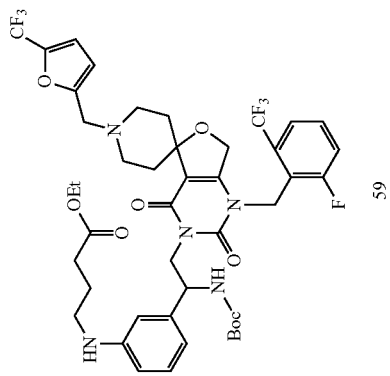

Step A. Preparation of methyl 2-amino-2-(3-nitrophenyl)acetate (53)

2-amino-2-(3-nitrophenyl)acetic acid (1.50 g, 7.65 mmol) was added to methanol (8 mL) and stirred for 10 min in an ice bath, followed by slowly adding thionyl chloride (0.91 mL, 12.5 mmol) thereto at the same temperature. The resulting solution was refluxed under a nitrogen atmosphere for 2 hrs, and cooled down to room temperature. The reaction solution was concentrated under reduced pressure and the residue obtained was used in the next step without further purification.

Step B. Preparation of methyl 2-((tert-butoxycarbonyl)amino)-2-(3-nitrophenyl)acetate (54)

Methyl 2-amino-2-(3-nitrophenyl)acetate (53) (crude, 7.65 mmol) obtained in Step A was diluted with dichloromethane (20 mL), and then sodium bicarbonate (964 mg, 11.5 mmol), triethylamine (2.13 mL, 15.3 mmol) and ditert-butyl dicarbonate (3.34 g, 15.3 mmol) were slowly added thereto in sequence at room temperature. The reaction solution was stirred for 2 hrs at the same temperature, and a saturated aqueous solution of ammonium chloride (25 mL) was added thereto. The aqueous layer was extracted twice with ethyl acetate. The organic layer was collected, dried over $Na_2SO_4$, filtered, and concentrated under reduced pressure. The residue was purified by silica gel chromatography (eluent: hexane/ethyl acetate=90/10~75/25), and dried under vacuum to yield the title compound as ivory solid (830 mg, yield: 35%).

Step C. Preparation of tert-butyl (2-hydroxy-1-(3-nitrophenyl)ethyl)carbamate (55)

Methyl 2-((tert-butoxycarbonyl)amino)-2-(3-nitrophenyl)acetate (54) (830 mg, 2.67 mmol) obtained in Step B was added to anhydrous tetrahydrofuran (100 mL), stirred for 10 min in an ice bath, and then lithium boron tetrahydride ($LiBH_4$, 850 mg, 22.4 mmol) was slowly added thereto in small portion at room temperature. The reaction solution was stirred for 2 hrs at the same temperature, cooled in an ice bath, and added with a saturated ammonium chloride solution. The aqueous layer was extracted three times with dichloromethane. The organic layer was collected, dried over $Na_2SO_4$, filtered, and concentrated under reduced pressure. The residue was purified by silica gel chromatography (eluent: dichloromethane/methanol=99/1~95/5), and dried under vacuum to yield the title compound as pale yellow foam (470 mg, yield: 62%).

Step D. Preparation of 2-((tert-butoxycarbonyl)amino)-2-(3-nitrophenyl)ethyl methanesulfonate (56)

tert-butyl (2-hydroxy-1-(3-nitrophenyl)ethyl)carbamate (55) (460 mg, 1.63 mmol) obtained in Step C above was added to dichloromethane (5 ml), and then triethylamine (271 μl, 2.00 mmol) and methanesulfonyl chloride (139 μl, 1.79 mmol) were added thereto in sequence. The resulting solution was stirred for 30 min at the same temperature, and a saturated sodium bicarbonate solution was added thereto. The aqueous layer was extracted twice with dichloromethane. The organic layer was collected, dried over $MgSO_4$, filtered, and concentrated under reduced pressure. The residue obtained was used in the next step without further purification.

Step E. Preparation of tert-butyl (2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-(3-nitrophenyl)ethyl)carbamate (57)

2-((tert-butoxycarbonyl)amino)-2-(3-nitrophenyl)ethyl methanesulfonate (56) (crude, 1.63 mmol) obtained in Step D, 1-(2-fluoro-6-(trifluoromethyl)benzyl)-1'-((5-(trifluoromethyl)furan-2-yl)methyl)-1H-spiro[furo[3,4-d]pyrimidine-5,4'-piperidine]-2,4(3H,7H)-dione (33) (595 mg, 1.08 mmol), potassium carbonate (450 mg, 3.26 mmol) and tetrabutylammonium bromide (35 mg, 0.11 mmol) were suspended in acetone (25 ml), heated to 70° C., and stirred for 15 hrs. The solution was cooled down to room temperature, and the resulting solid was removed by filtration. The filtrate was concentrated under reduced pressure to remove acetone, and diluted with ethyl acetate (25 mL). The resulting solution was washed once with a saturated sodium bicarbonate solution (25 mL), dried over $MgSO_4$, and concentrated under reduced pressure. The residue was purified by silica gel chromatography (eluent: hexane/ethyl acetate=9/1~1/1), and dried under vacuum to obtain the title compound as ivory foam (680 mg, yield: 78%).

$^1$H NMR (600 MHz, $CDCl_3$) δ 1.38 (9H, s), 1.53-1.63 (2H, m), 2.36-2.40 (4H, m), 2.78-2.81 (2H, m), 3.63 (2H, s), 4.04-4.07 (1H, m), 4.29-4.34 (1H, m), 4.66-4.74 (2H, m), 5.03-5.27 (2H, m), 5.99 (1G, d), 6.30 (1H, d), 6.72-6.73 (1H, m), 6.69-6.76 (3H, m), 7.26-7.31 (1H, m), 7.48-7.51 (2H, m), 7.57 (1H, d), 7.72-7.74 (1H, m), 8.11-8.12 (1H, m), 8.20-8.21 (1H, m)

Step F. Preparation of tert-butyl (1-(3-aminophenyl)-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)carbamate (58)

Tert-butyl (2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-(3-nitrophenyl)ethyl)carbamate (57) (660 mg, 0.813 mmol) obtained in Step E was dissolved in methanol (8 ml), and added with Pd/C (70 mg, 10% w/w). The mixture was filled with hydrogen gas and stirred for 15 hrs. The resulting solution was filtered using a Celite pad. The filtrate was concentrated under reduced pressure, and dried under vacuum to obtain the title compound as ivory foam (430 mg, yield: 68%).

$^1$H NMR (600 MHz, $CDCl_3$) δ 1.36 (9H, s), 1.55-1.63 (2H, m), 2.36-2.46 (4H, m), 2.78-2.82 (2H, m), 3.62 (2H, s), 3.66 (2H, br), 3.98-4.01 (1H, m), 4.23-4.25 (1H, m), 4.65-4.74 (2H, m), 4.90-5.55 (4H, m), 6.30 (1H, d), 6.56-6.58 (1H, m), 6.69-6.76 (3H, m), 7.11 (1H, t), 7.26-7.29 (2H, m), 7.45-7.49 (1H, m), 7.55-7.57 (1H, m)

Step G. Preparation of ethyl 4-((3-(1-((tert-butoxycarbonyl)amino)-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)phenyl)amino)butanoate (59)

Tert-butyl (1-(3-aminophenyl)-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)carbamate (58) (100 mg, 0.128 mmol) obtained in Step F was added to acetonitrile (3.0 mL) together with ethyl 4-bromobutyrate (20 µL, 0.141 mmol) and diisopropyl ethylamine (45 µL, 0.256 mmol), and the mixture was heated to 60° C., followed by stirring at the same temperature for 48 hrs. A saturated ammonium chloride solution was added thereto, and the aqueous layer was extracted three times with dichloromethane. The organic layer was collected, dried over $MgSO_4$, concentrated, purified by MPLC (eluent: hexane/ethyl acetate=1/1~1/99), and dried under vacuum to obtain the title compound as ivory foam (33 mg, yield: 29%).

$^1$H NMR (600 MHz, $CDCl_3$) δ 1.30 (3H, t), 1.52-1.60 (4H, m), 2.32-2.43 (4H, m), 2.76-2.79 (2H, m), 3.60 (2H, s), 4.01 (1H, dd), 4.13 (1H, dd), 4.25-4.31 (3H, m), 4.60 (2H, s), 4.65-4.71 (2H, m), 5.10-5.16 (2H, m), 6.29 (1H, d), 6.71-6.72 (1H, m), 6.84-6.87 (2H, m), 7.27-7.31 (3H, m), 7.45-7.48 (1H, m), 7.56 (1H, d)

Step H. Preparation of ethyl 4-((3-(1-amino-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)phenyl)amino)butanoate (60)

Ethyl 4-((3-(1-((tert-butoxycarbonyl)amino)-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidin-5,4'-piperidine]-3(2H,4H,7H)-yl)ethyl)phenyl)amino)butanoate (59) (30 mg, 0.038 mmol) obtained in Step G was added to dichloromethane (1 mL) together with trifluoroacetic acid (100 µL), followed by stirring for 2 hrs at room temperature. The reaction solution was neutralized with a saturated sodium bicarbonate solution, and extracted three times with dichloromethane. The organic layer was collected, dried over $Na_2SO_4$, concentrated, purified by MPLC (eluent: dichloromethane/methanol=99/1~9/1), and dried under vacuum to obtain the title compound as ivory foam (22 mg, yield: 73%).

$^1$H NMR (600 MHz, $CDCl_3$) δ 1.24 (3H, t), 1.57-1.59 (2H, m), 1.86-1.94 (3H, m), 2.37-2.41 (5H, m), 2.80 (2H, s), 3.15 (2H, t), 4.26-4.30 (2H, m), 4.65-4.71 (2H, m), 5.07-5.20 (2H, m), 6.34 (1H, s), 4.48-4.49 (1H, m), 6.67-6.72 (3H, m), 7.11 (1H, t), 7.27-7.29 (1H, m), 7.42-7.46 (1H, m), 7.53-7.54 (1H, d)

Step I. Preparation of 4-((3-(1-amino-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)phenyl)amino)butanoic acid (61)

Ethyl 4-((3-(1-amino-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)phenyl)amino)butanoate (60) (20 mg, 0.025 mmol) obtained in Step H was added to ethanol (1.0 mL) together with an aqueous solution of 1N NaOH (75 µL, 0.075 mmol), followed by stirring for 2 hrs at room temperature. The resulting solution was neutralized by adding an aqueous solution of 1N HCl, and concentrated under reduced pressure to remove ethanol. The aqueous layer was extracted three times with dichloromethane. The organic layer was collected, dried over $Na_2SO_4$, concentrated, purified by MPLC (eluent: dichloromethane/methanol=80/20~70/30), and dried under vacuum to obtain the title compound as ivory foam (10 mg, yield: 52%).

$^1$H NMR (600 MHz, DMSO-$d_6$) δ 1.43-1.50 (2H, m), 1.67-1.72 (2H, m), 1.87-2.27 (6H, m), 2.65-2.68 (2H, m), 2.91-2.94 (2H, m), 3.57 (2H, s), 3.68-3.90 (3H, m), 4.86 (2H, s), 4.98 (2H, s), 6.33-6.37 (2H, m), 6.44-6.45 (1H, m), 6.51 (1H, d), 6.91 (1H, t), 7.12-7.13 (1H, m), 7.49-7.61 (3H, m)

MS (ESI) m/z 768.2 ($MH^+$)

Examples 13-1 and 13-2

The compounds of Examples 13-1 and 13-2 were prepared in the same manner as described in Example 13, except for using ethyl 2-bromoacetate and ethyl 3-bromopropanoate, respectively, for introducing the corresponding $R_5$ group shown in Table 8 below instead of ethyl 4-bromobutyrate in Step G of Example 13.

TABLE 8

| Example | —$R_5$ | M.W. | Mass |
|---|---|---|---|
| 13-1 | (HN-CH2-C(O)-OH attached to phenyl with NH2) | 739.2 | 740.1 |
| 13-2 | (HN-CH2-CH2-C(O)-OH attached to phenyl with NH2) | 753.3 | 754.2 |

Examples 13-3 to 13-8

The compounds of Examples 13-3 and 13-4 were prepared in the same manner as described in Step H of Example 13 via deprotection reaction, except for using compounds 57 and 58, respectively, and each compound comprising the corresponding moiety shown in Table 9 below.

Also, the compounds of Examples 13-5 to 13-8 were prepared in the same manner as described in Example 13 for preparing the compounds 57 and 58, except for using 2-amino-2-(2-nitrophenyl)acetic acid and 2-amino-2-(4-nitrophenyl) acetic acid instead of 2-amino-2-(3-nitrophenyl) acetic acid as a starting material of Example 13, followed by the same deprotection reaction as described in Step H of Example 13.

Example 14

Synthesis of tert-butyl (2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-(3-(3-methoxyureido)phenyl)ethyl)carbamate (63)

TABLE 9

| Example | —R₅ | M.W. | Mass |
|---------|-----|------|------|
| 13-3 | 3-nitrophenyl, 1-amino | 711.6 | 712.3 |
| 13-4 | 3-aminophenyl, 1-amino | 681.6 | 682.3 |
| 13-5 | 2-nitrophenyl, 1-amino | 711.6 | 712.5 |
| 13-6 | 2-aminophenyl, 1-amino | 681.6 | 682.2 |
| 13-7 | 4-nitrophenyl, 1-amino | 711.5 | 712.2 |
| 13-8 | 4-aminophenyl, 1-amino | 681.6 | 681.9 |

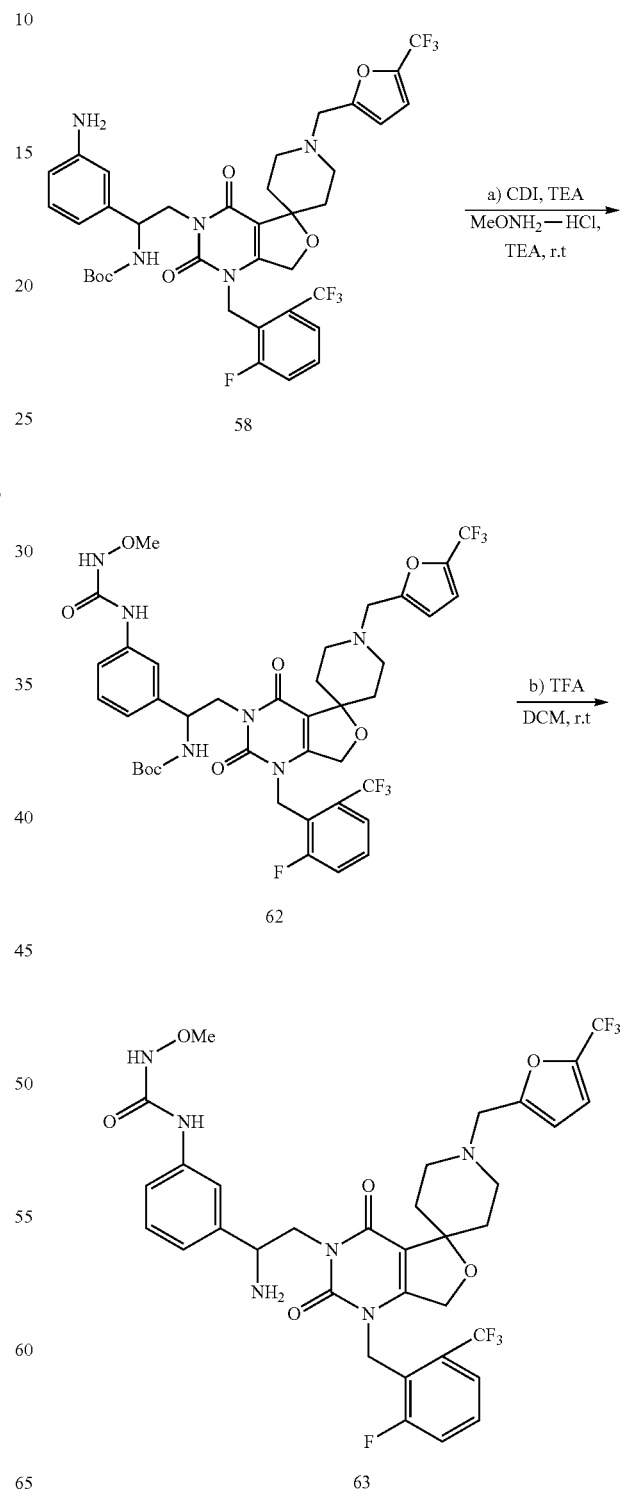

Step A. Preparation of tert-butyl (2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-(3-(3-methoxyureido)phenyl)ethyl)carbamate (62)

Tert-butyl (1-(3-aminophenyl)-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)carbamate (58) (158 mg, 0.202 mmol) obtained in Example 13 was added to dichloromethane (3 mL), stirred for 10 mins in an ice bath, and added with CDI (66 mg, 0.404 mmol) and triethylamine (56 μL, 0.404 mmol) at the same temperature. The resulting solution was heated to room temperature, and stirred for 48 hrs. The reaction solution was stirred for 10 mins in an ice bath again, added with MeONH$_2$—HCl (169 mg, 2.02 mmol) and triethylamine (280 μL, 2.02 mmol), and the mixture was heated to room temperature and stirred for 4 hrs. The reaction solution was neutralized with a saturated sodium bicarbonate solution, and extracted twice with dichloromethane. The organic layer was collected, dried over Na$_2$SO$_4$, concentrated, purified by MPLC (eluent: n-hexane/ethyl acetate=75/15~10/90), and dried under vacuum to obtain the title compound as ivory foam (122 mg, yield: 71%).

$^1$H NMR (300 MHz, CDCl$_3$) δ 7.67 (1H, d), 7.59-7.52 (2H, m), 7.47 (1H, dd), 7.33-7.25 (2H, m), 7.20 (1H, s), 7.11-7.09 (2H, t), 6.72 (1H, dd), 6.29 (1H, d), 5.72-4.94 (3H, m), 4.76-4.64 (2H, m), 4.33-4.25 (1H, m), 3.80 (3H, s), 3.62 (2H, s), 2.80 (2H, d), 2.40 (4H, d), 1.58 (2H, t), 1.37-1.24 (9H, m).

Step B. Preparation of tert-butyl (2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-(3-(3-methoxyureido)phenyl)ethyl)carbamate (63)

The procedure of Step H of Example 13 was repeated except for using tert-butyl (2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-(3-(3-methoxyureido)phenyl)ethyl)carbamate (62) (122 mg, 0.142 mmol) to obtain the title compound as ivory foam (87 mg, yield: 81%).

$^1$H NMR (300 MHz, CDCl$_3$) δ 7.61-7.54 (3H, m), 7.49-7.42 (1H, m), 7.31-7.26 (m, 3H), 7.14-7.10 (2H, m), 6.72 (1H, dd), 6.28 (1H, d), 5.13 (2H, s), 4.68 (2H, s), 4.34 (1H, dd), 4.20-4.12 (1H, m), 4.04 (1H, dd), 3.80 (3H, s), 3.60 (2H, s), 3.49 (1H, s), 2.77 (2H, d), 2.48-2.26 (4H, m), 1.74-1.41 (3H, m).

Example 15

Synthesis of 1-(3-(1-amino-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)phenyl)-3-methylurea (65)

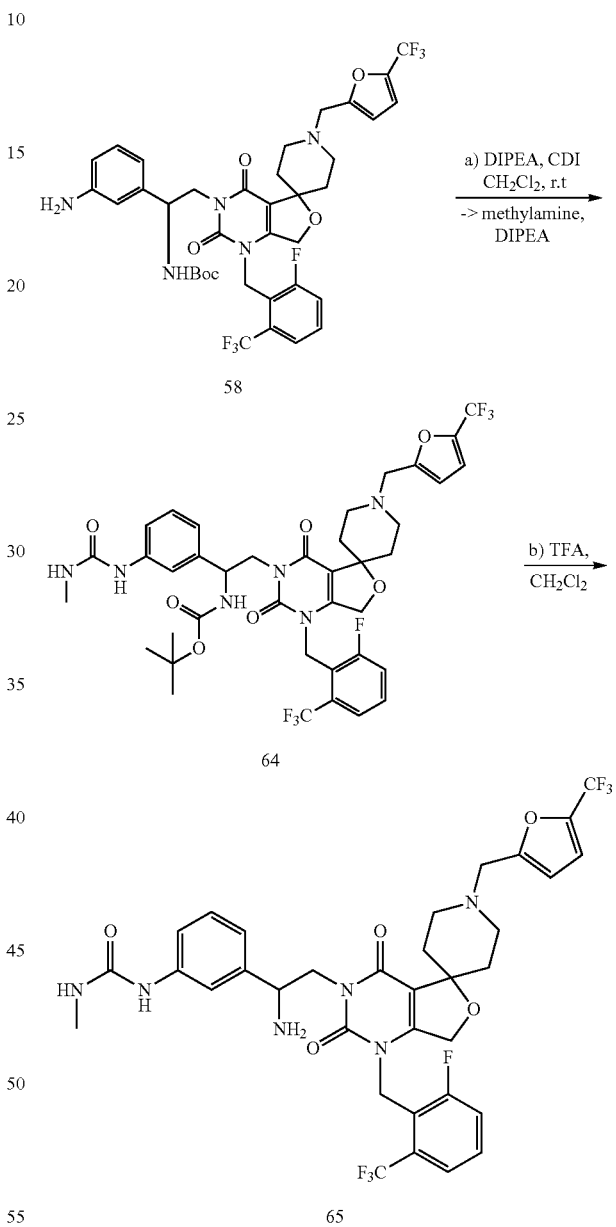

Step A. Preparation of tert-butyl (2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-(3-(3-methylureido)phenyl)ethyl)carbamate (64)

A solution prepared by adding tert-butyl (1-(3-aminophenyl)-2-(1-(2-fluoro-6-(trifluoromethyl)benzyl)-2,4-dioxo-1'-((5-(trifluoromethyl)furan-2-yl)methyl)-1H-spiro[furo[3, 4-d]pyrimidin-5,4'-piperidine]-3(2H,4H,7H)-yl)ethyl) carbamate (58) (33 mg, 0.0512 mmol) and DIPEA (18 L, 0.102 mmol) to CH$_2$Cl$_2$ (1 mL) was added with CDI (17 mg, 0.102 mol) at 0° C. The mixture was stirred for 1 hr at room temperature, cooled down to 0° C., and 2M N-methylamine dissolved in THF (0.1 ml, 0.204 mmol) and DIPEA (36 μL, 0.204 mmol) were added thereto. The mixture was stirred for 2 hrs at room temperature, and 2M N-methylamine dissolved in THF (0.2 ml, 0.408 mmol) was added thereto, followed by stirring for 1 hr. The reaction solution was diluted with CH$_2$Cl$_2$, washed with a saturated NaHCO$_3$ solution, and then washed with brine. The organic layer was dried over Na$_2$SO$_4$, filtered, concentrated under reduced pressure, purified by MPLC (eluent: dichloromethane/methanol=98/2~97/3), and dried under vacuum to obtain white solid (21.5 mg, yield: 50%).

$^1$H NMR (300 MHz, CDCl$_3$) δ 7.55 (d, 1H), 7.50-7.42 (m, 2H), 7.30-7.17 (m, 3H), 7.10-7.06 (m, 1H), 6.97 (d, 1H), 6.77 (bs, 1H), 6.72 (dd, 1H), 6.28 (d, 1H), 5.78 (d, 1H), 5.24-5.03 (dd, 2H), 4.94 (m, 1H), 4.69 (dd, 2H), 4.27 (t, 1H), 4.19 (m, 1H), 4.00 (dd, 1H), 3.61 (s, 2H), 2.77 (m, 5H), 2.42-2.28 (m, 4H), 1.54 (m, 2H), 1.36-1.23 (m, 9H)

Step B. Preparation of 1-(3-(1-amino-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl) ethyl)phenyl)-3-methylurea (65)

Tert-butyl (2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-(3-(3-methylureido)phenyl)ethyl)carbamate (64) (21.5 mg, 0.0291 mmol) obtained in Step B above was added to dichloromethane (0.7 mL) together with trifluoroacetic acid (0.07 mL), and stirred for 3 hrs at room temperature. The reaction solution was neutralized with a saturated NaHCO$_3$ (aq) solution, and extracted with dichloromethane. The resulting solution was concentrated, and purified by MPLC (10% methanol/dichloromethane) to obtain white amorphous foam (10 mg, yield: 47%).

MS (ESI) m/z 739.40 (MH$^+$)

Example 16

Synthesis of N-(3-(1-amino-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)phenyl)acetamide (67)

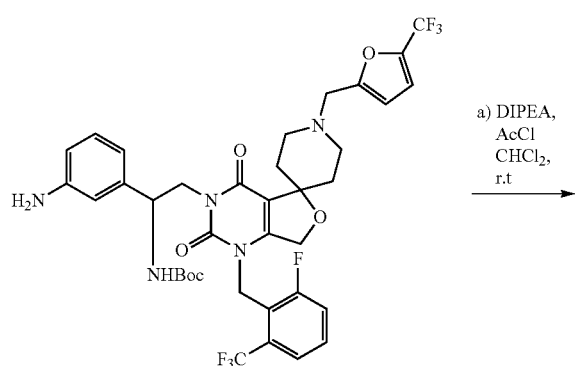

58

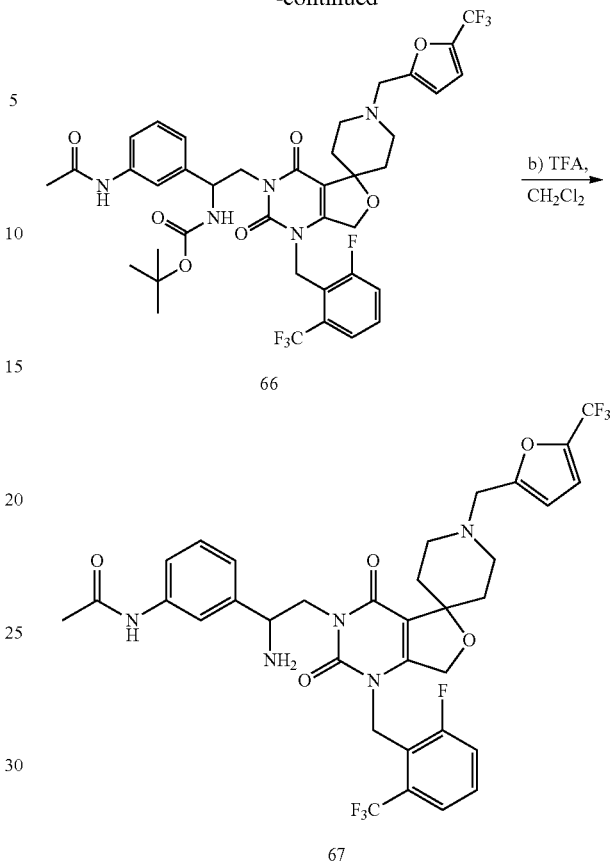

66

67

Step A. Preparation of tert-butyl (1-(3-acetamidophenyl)-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3 (2H,4H,7H)-yl)ethyl)carbamate (66)

A solution prepared by adding tert-butyl (1-(3-aminophenyl)-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl) carbamate (58) (30 mg, 0.0383 mmol) and DIPEA (36 μL, 0.204 mmol) to CH$_2$Cl$_2$ (1 mL) was added with acetyl chloride (5.4 μL, 0.0768 mol) at 0° C. The resulting mixture was stirred for 1 hr at room temperature. The reaction solution was diluted with CH$_2$Cl$_2$, and washed with a saturated NaHCO$_3$ and brine. The organic layer was dried over Na$_2$SO$_4$, filtered, and concentrated under reduced pressure. The residue was purified by MPLC (eluent: dichloromethane/methanol=98/2), and dried under vacuum to obtain white solid (28 mg, yield: 88%).

$^1$H NMR (300 MHz, CDCl$_3$) δ 7.64 (m, 1H), 7.55 (dd, 1H), 7.50-7.42 (m, 1H), 7.26 (m, 1H), 7.30-7.24 (m, 2H), 7.20 (m, 1H), 7.08 (d, 1H), 6.72 (dd, 1H), 6.29 (d, 1H), 5.71 (d, 1H), 5.27-5.02 (dd, 2H), 4.95 (m, 1H), 4.75-4.62 (dd, 2H), 4.26 (t, 1H), 3.98 (dd, 1H), 3.62 (s, 2H), 2.80 (m, 2H), 2.45-2.22 (m, 4H), 2.14 (s, 3H), 1.61-1.52 (t, 2H), 1.36-1.22 (m, 9H)

Step B. Preparation of N-(3-(1-amino-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)phenyl)acetamide (67)

Tert-butyl (1-(3-acetamidophenyl)-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)carbamate (66) (28 mg, 0.0339 mmol) obtained in Step A was added to dichloromethane (0.7 mL) together with trifluoroacetic acid (0.07 mL), followed by stirring for 3 hrs at room temperature. The reaction solution was neutralized with a saturated NaHCO$_3$ (aq) solution, and extracted with dichloromethane. The resulting solution was concentrated, and purified by MPLC (10% methanol/dichloromethane) to obtain white amorphous foam (18 mg, yield: 73%).

MS (ESI) m/z 724.20 (MH$^+$)

Test Example 1

GnRH Receptor-Membrane Binding Assay

A GnRH receptor membrane binding assay was carried out for the compounds of the present invention by employing a membrane substrate (PerkinElmer) isolated from CHO-K1 cells (ATCC CCL-61) stably transfected with a GnRH receptor.

A reaction was initiated by the addition of a 0.2 nM [$^{125}$I]-labeled D-Trp$^6$-LHRH peptide and the GnRH receptor membrane substrate at a density of 1 μg/250 μL/well, together with the inventive compounds at various concentrations ranging from 0.1 nM to 100 nM, to a binding buffer composed of 25 mM Hepes (pH 7.4), 10 mM MgCl$_2$, 1 mM CaCl$_2$ and 0.5% BSA (pH 7.4). The reaction mixture was incubated at 27° C. for 1 hr and subjected to vacuum suction for binding to a filter (Fitermat A, PerkinElmer). The filter was washed several times with 50 mM tris-HCl buffer to terminate the reaction. The radioactivity binding to the filter was measured using MicroBeta2 TriLux (PerkinElmer). The binding inhibition rate (%) of the inventive compounds were analyzed on the basis of the measured radioactivity, and IC$_{50}$ value was calculated using a non-linear least square regression method with Prism (GraphPad, Inc.). The results of GnRH binding inhibition (%) are shown in Table 10 below.

Test Example 2

Screening of Gene Expression for Evaluating Antagonistic Effect on GnRH Receptor For evaluation of antagonistic effect on GnRH receptor, double-transformed cell line, HEK293 (ATCC CRL-1573) which is transformed with pcDNA3.1/GnRH receptor and pGL4/NFAT promoter, was employed.

To conduct a GnRH receptor assay, the HEK293 (ATCC CRL-1573) cell line was diluted at a density of 3×10$^4$ cells/well in a DMEM medium supplemented with 10% FBS, 1% Penicillin-Streptomycin, and plated into polylysine-coated 96-well plates having a white-clear bottom, followed by incubating the cells at 37° C. for 24 hrs. Then, the medium was changed with a serum-free DMEM medium (1% Penicillin-Streptomycin), and the cells were incubated for an additional 16 hrs before use.

Test compounds were added to the wells in an amount of 1 μM to 0.01 nM, respectively, and further incubated for 1 hr. Then, leuprolide acetate as a ligand (Sigma) was added to the wells in an amount of 1 nM or 20 nM and subjected to an additional incubation for 6 hrs. The reagent of Luciferase assay system (Promega, Cat. No. E1500) was added to the wells and luminescence was measured using a luminometer (PerkinElmer, VICTOR3™, 1420 Multilabel Counter). The compound of formula 10b described in J. Med. Chem. 2008, 51, 7478 was used as a comparative compound.

Each sample was analyzed at a 6-dose level and the NFAT reporter inhibitory rate (%) of the inventive compounds was calculated according to the following equation based on the measured luminescence.

Inhibition (%)={1−(compound−negative control)/(positive control−negative control)}×100   [Equation]

wherein, positive control is GnRH treated group; and negative control is non-treated group.

The results of NFAT reporter activity inhibition (%) are shown in Table 10 below.

TABLE 10

| Example No. | GnRH binding inhibition (%) at 10 nM | NFAT reporter activity inhibition (%) at 100 nM |
|---|---|---|
| 1-2 | 50.8 | Not tested |
| 1-3 | Not tested | 15 |
| 1-14 | 96.0 | 34 |
| 1-15 | 91.3 | 67 |
| 1-19 | 97.5 | 89 |
| 1-25 | 91.3 | 56 |
| 1-26 | 102 | 22 |
| 1-29 | 104 | 58 |
| 1-42 | 93.9 | 82 |
| 1-50 | 96.3 | 17 |
| 1-51 | 95.6 | 30 |
| 1-63 | 88.6 | 18 |
| 3-5 | 101 (at 10 nM) | 99 |
| 13-5 | 75.6 (at 10 nM) | 99 |
| 13-8 | 84.7 (at 10 nM) | 87 |
| 36 | 88 (at 10 nM) | 88.2 (at 10 nM) |
| 63 | 89.8 (at 10 nM) | 100 |
| Comparative compond 1* | 90% (at 1 nM) | 6.2 nM (IC$_{50}$) |

*the compound of formula 10b in J. Med. Chem. 2008, 51, 7478

As can be seen in Table 10, the inventive compounds inhibit the GnRH binding to the GnRH receptor and also inhibit the activity of NFAT receptor. Further, the inventive compounds (Examples 1-15 and 1-19) which comprises benzyl group as a substituent at spiro-piperidine moiety exhibit the improved inhibitory effect compared with those of the inventive compounds comprising alkyl group (Examples 1-2 and 1-3).

What is claimed is:

1. A compound of formula (I), or a stereoisomer, or a pharmaceutically acceptable salt thereof:

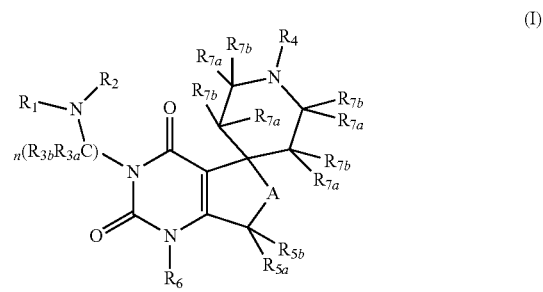

(I)

wherein,

A is $CR_{8a}R_{8b}$, O, S or $NR_9$;

$R_1$ and $R_2$, which may be the same or different, being each independently hydrogen, $(C_1$-$C_{10})$alkyl, substituted $(C_1$-$C_{10})$alkyl, $(C_3$-$C_{10})$cycloalkyl, substituted $(C_3$-$C_{10})$cycloalkyl, $(C_6$-$C_{12})$aryl, substituted $(C_6$-$C_{10})$aryl, $(C_6$-$C_{12})$aryl, $(C_1$-$C_{10})$alkyl, substituted $(C_6$-$C_{12})$aryl $(C_1$-$C_{10})$alkyl, $(C_1$-$C_{20})$heteroaryl, substituted $(C_1$-$C_{20})$heteroaryl, $(C_1$-$C_{20})$heteroaryl$(C_1$-$C_{10})$alkyl, substituted $(C_1$-$C_{20})$heteroaryl$(C_1$-$C_{10})$alkyl, $(C_1$-$C_{20})$heterocycle, substituted $(C_1$-$C_{20})$heterocycle, $(C_1$-$C_{20})$heterocyclyl$(C_1$-$C_{10})$alkyl, substituted $(C_1$-$C_{20})$heterocyclyl$(C_1$-$C_{10})$alkyl, or —$(CR_{1a}R_{1b})_s$—$R_{12}$;

$R_{3a}$ and $R_{3b}$, which may be the same or different, being each independently hydrogen, $(C_1$-$C_{10})$alkyl, substituted $(C_1$-$C_{10})$alkyl, $(C_3$-$C_{10})$cycloalkyl, substituted $(C_3$-$C_{10})$cycloalkyl, $(C_1$-$C_{10})$alkoxy, $(C_1$-$C_{10})$alkylthio, $(C_1$-$C_{10})$alkylamino, $(C_6$-$C_{12})$aryl, substituted $(C_6$-$C_{12})$aryl, $(C_6$-$C_{12})$aryl$(C_1$-$C_{10})$alkyl, substituted $(C_6$-$C_{12})$aryl$(C_1$-$C_{10})$alkyl, $(C_1$-$C_{20})$heteroaryl, substituted $(C_1$-$C_{20})$heteroaryl, $(C_1$-$C_{20})$heteroaryl$(C_1$-$C_{10})$alkyl, substituted $(C_1$-$C_{20})$heteroaryl$(C_1$-$C_{10})$alkyl, $(C_1$-$C_{20})$heterocycle, substituted $(C_1$-$C_{20})$heterocycle, $(C_1$-$C_{20})$heterocyclyl$(C_1$-$C_{10})$alkyl, substituted $(C_1$-$C_{20})$heterocyclyl$(C_1$-$C_{10})$alkyl, —$COOR_{13}$ or —$CONR_{13}R_{14}$ or;

$R_{3a}$ and $R_{3b}$, together with the carbon atom attached thereto form a homocyclic ring, a substituted homocyclic ring, a heterocyclic ring, or a substituted heterocyclic ring; or $R_{3a}$ and a carbon bonded thereto, together with $R_1$ and a nitrogen atom bonded thereto, form a heterocyclic ring or a substituted heterocyclic ring;

$R_4$ is —$(CR_{9a}R_{9b})_r$—Z—Y;

n is an integer of 2, 3 or 4;

s is an integer of 1, 2, 3 or 4;

r is an integer of 0, 1 or 2;

Z represents a direct bond, or —O—, —S—, —$NR_{11}$—, —SO—, —$SO_2$—, —$OSO_2$—, —$SO_2O$—, —$SO_2NR_{11}$—, —$NR_{11}SO_2$—, —CO—, —COO—, —OCO—, —$CONR_{11}$—, —$NR_{11}CO$—, —$NR_{11}CONR_{11a}$—, —$OCONR_{11}$— or —$NR_{11}COO$—;

Y is hydrogen, halogen, $(C_1$-$C_{10})$alkyl, substituted $(C_1$-$C_{10})$alkyl, $(C_3$-$C_{10})$cycloalkyl, substituted $(C_3$-$C_{10})$cycloalkyl, $(C_6$-$C_{12})$aryl, substituted $(C_6$-$C_{12})$aryl, $(C_6$-$C_{12})$aryl$(C_1$-$C_{10})$alkyl, substituted $(C_6$-$C_{12})$aryl, $(C_1$-$C_{10})$alkyl, $(C_1$-$C_{20})$heteroaryl, substituted $(C_1$-$C_{20})$heteroaryl, $(C_1$-$C_{20})$heteroaryl$(C_1$-$C_{10})$alkyl or substituted $(C_1$-$C_{20})$heteroaryl$(C_1$-$C_{10})$alkyl;

$R_6$ is hydrogen, $(C_1$-$C_{10})$alkyl, substituted $(C_1$-$C_{10})$alkyl, $(C_3$-$C_{10})$cycloalkyl, substituted $(C_3$-$C_{10})$cycloalkyl, $(C_6$-$C_{12})$aryl, substituted $(C_6$-$C_{12})$aryl, $(C_6$-$C_{12})$aryl$(C_1$-$C_{10})$alkyl, substituted $(C_6$-$C_{12})$aryl$(C_1$-$C_{10})$alkyl, $(C_1$-$C_{20})$heteroaryl, substituted $(C_1$-$C_{20})$heteroaryl, $(C_1$-$C_{20})$heteroaryl$(C_1$-$C_{10})$alkyl or substituted $(C_1$-$C_{20})$heteroaryl$(C_1$-$C_{10})$alkyl;

$R_9$ is hydrogen, $(C_1$-$C_{10})$alkyl or $(C_1$-$C_{10})$acyl;

$R_{12}$ is —$CO_2R_{13}$, —COOH or an acid isostere;

$R_{1a}$ and $R_{1b}$, which may be the same or different, being each independently hydrogen, $(C_1$-$C_{10})$acyl, hydroxyl, halogen, cyano, $(C_1$-$C_{10})$alkyl, substituted $(C_1$-$C_{10})$alkyl, $(C_3$-$C_{10})$cycloalkyl, substituted $(C_3$-$C_{10})$cycloalkyl, $(C_1$-$C_{10})$alkoxy, $(C_1$-$C_{10})$alkylthio, $(C_1$-$C_{10})$alkylamino, —$COOR_{13}$— or $CONR_{13}R_{14}$—; or $R_{1a}$ and $R_{1b}$, together with the atom(s) to which they are attached independently from a homocyclic ring, a substituted homocyclic ring, a heterocyclic ring or a substituted heterocyclic ring;

$R_{5a}$, $R_{5b}$, $R_{7a}$, $R_{7b}$, $R_{8a}$ and $R_{8b}$, which may be the same or different, being each independently hydrogen, $(C_1$-$C_{10})$acyl, hydroxyl, amino, halogen, cyano, $(C_1$-$C_{10})$alkyl, substituted $(C_1$-$C_{10})$alkyl, $(C_3$-$C_{10})$cycloalkyl, substituted $(C_3$-$C_{10})$cycloalkyl, $(C_1$-$C_{10})$aryl, substitute $(C_1$-$C_{10})$aryl, $(C_1$-$C_{10})$alkoxy, $(C_1$-$C_{10})$alkylthio, $(C_1$-$C_{10})$alkylamino, —$COOR_{13}$, or —$CONR_{14}R_{15}$; and $R_{9a}$, $R_{9b}$, $R_{11}$, $R_{11a}$, $R_{13}$, $R_{14}$ and $R_{15}$, which may be the same of different, being each independently hydrogen, $(C_1$-$C_{10})$alkyl, $(C_6$-$C_{12})$aryl or $(C_6$-$C_{12})$aryl, $(C_1$-$C_{10})$alkyl;

wherein, the heterocyclic ring, the heterocycle, the heterocyclylalkyl, heteroaryl and heteroarylalkyl contain at least one heteroatoms selected from the group consisting of N, O and S; and "substituted" means a replacement with at least one substituent selected from the group consisting of halogen, acetylene, vinyl, hydroxy, cyano, nitro, amino, $(C_1$-$C_{10})$alkylamino, di$(C_1$-$C_{10})$alkylamino, $(C_1$-$C_{10})$alkyl, $(C_3$-$C_{10})$cycloalkyl, $(C_1$-$C_{10})$alkoxy, $(C_1$-$C_{10})$alkylthio, halo$(C_1$-$C_{10})$alkyl, $(C_6$-$C_{12})$aryl, $(C_6$-$C_{12})$aryl$(C_1$-$C_{10})$alkyl, $(C_1$-$C_{20})$heteroaryl, $(C_1$-$C_{20})$heteroaryl$(C_1$-$C_{10})$alkyl, $(C_1$-$C_{20})$heterocycle, $(C_1$-$C_{20})$heterocyclyl$(C_1$-$C_{10})$alkyl, —$NR_aR_b$, —$NR_aC(=O)R_b$, —$NR_aC(=O)NR_aOR_b$, —$NR_aC(=O)NR_aR_b$, —$NR_aC(=O)OR_b$, —$NR_aSO_2R_b$, —$C(=O)R_a$, —$C(=O)OR_a$, —$OC(=O)R_a$, —$C(=O)NR_aR_b$, —$OC(=O)NR_aR_b$, —$OR_a$, —$SR_a$, —$S(=O)_2R_a$, —$OS(=O)_2R_a$ and —$S(=O)_2OR_a$, wherein $R_a$ and $R_b$, which may be the same or different, being each independently hydrogen, $(C_1$-$C_{10})$alkyl, halo$(C_1$-$C_{10})$alkyl, $(C_3$-$C_{10})$cycloalkyl, $(C_6$-$C_{12})$aryl, $(C_6$-$C_{12})$aryl$(C_1$-$C_{10})$alkyl, $(C_1$-$C_{20})$heteroaryl, $(C_1$-$C_{20})$heteroaryl$(C_1$-$C_{10})$alkyl, $(C_1$-$C_{20})$heterocycle, $(C_1$-$C_{20})$heterocyclyl$(C_1$-$C_{10})$alkyl or —$(CH_2)_zC(=O)R_c$, z is an integer of 1, 2, 3 or 4, and $R_c$ is hydroxyl, $(C_1$-$C_{10})$alkyl, $(C_3$-$C_{10})$cycloalkyl or $(C_1$-$C_{10})$alkoxy.

2. The compound of claim 1, wherein,

A is $CH_2$, O, S or $NR_9$ wherein $R_9$ is hydrogen or methyl;

n is an integer of 2;

$R_1$ and $R_2$ being each independently hydrogen, $(C_6$-$C_{12})$aryl$(C_1$-$C_{10})$alkyl, substituted $(C_6$-$C_{12})$aryl$(C_1$-$C_{10})$alkyl, $(C_1$-$C_{20})$heteroaryl$(C_1$-$C_{10})$alkyl, substituted $(C_1$-$C_{20})$heteroaryl$(C_1$-$C_{10})$alkyl or —$(CH_2)_s$—$R_{12}$;

s is an integer of 1, 2, 3 or 4;

$R_{3a}$ and $R_{3b}$ being each independently hydrogen, $(C_6$-$C_{12})$aryl, substituted $(C_6$-$C_{12})$aryl, $(C_1$-$C_{20})$heteroaryl or substituted $(C_1$-$C_{20})$heteroaryl;

$R_4$ is hydrogen, $(C_6$-$C_{12})$aryl, substituted $(C_6$-$C_{12})$aryl, $(C_1$-$C_{20})$heteroaryl, substituted $(C_1$-$C_{10})$heteroaryl, $(C_6$-$C_{12})$aryl$(C_1$-$C_{10})$alkyl, substituted $(C_6$-$C_{12})$aryl, $(C_1$-$C_{10})$alkyl, $(C_1$-$C_{20})$heteroaryl$(C_1$-$C_{10})$alkyl, substituted $(C_1$-$C_{20})$heteroaryl$(C_1$-$C_{10})$alkyl, $(C_1$-$C_{10})$alkyl, substituted $(C_1$-$C_{10})$alkyl, —$C(=O)R_{11}$, —$SO_2R_{11}$ or —$C(=O)OR_{11}$;

$R_6$ is $(C_6$-$C_{12})$aryl$(C_1$-$C_{10})$alkyl, substituted $(C_6$-$C_{12})$aryl, $(C_1$-$C_{10})$alkyl, $(C_1$-$C_{20})$heteroaryl$(C_1$-$C_{10})$alkyl or substituted $(C_1$-$C_{20})$heteroaryl$(C_1$-$C_{10})$alkyl;

$R_{5a}$, $R_{5b}$, $R_{7a}$, $R_{7b}$, $R_{8a}$ and $R_{8b}$ being each independently hydrogen;

$R_{11}$ is hydrogen, $(C_1$-$C_{10})$alkyl, $(C_6$-$C_{12})$aryl, or $(C_6$-$C_{12})$aryl$(C_1$-$C_{10})$alkyl; and R$_{12}$ is —COOH or an acid isostere selected from the group consisting of:

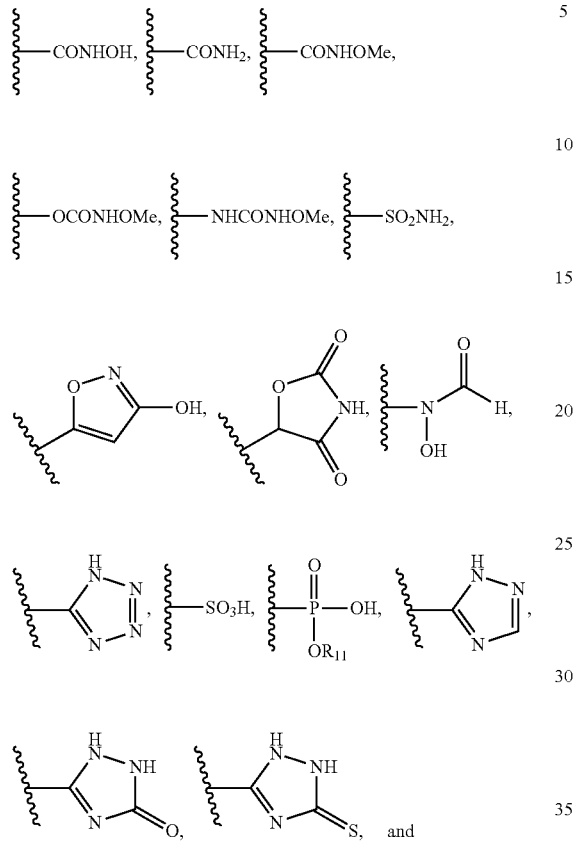

wherein, "substituted" means a replacement with at least one substituent selected from the group consisting of halogen, acetylene, vinyl, hydroxy, cyano, nitro, amino, $(C_1\text{-}C_{10})$alkylamino, di$(C_1\text{-}C_{10})$alkylamino, $(C_1\text{-}C_{10})$alkyl, $(C_3\text{-}C_{10})$cycloalkyl, $(C_1\text{-}C_{10})$alkoxy, $(C_1\text{-}C_{10})$alkylthio, halo$(C_1\text{-}C_{10})$alkyl, —NR$_a$R$_b$, —NR$_a$C(=O)R$_b$, —NR$_a$C(=O)NR$_a$OR$_b$, —NR$_a$C(=O)NR$_a$R$_b$, —NR$_a$C(=O)OR$_b$, —NR$_a$SO$_2$R$_b$, —C(=O)R$_a$, —C(=O)OR$_a$, —OC(=O)R$_a$, —C(=O)NR$_a$R$_b$, —OC(=O)NR$_a$R$_b$, —OR$_a$, —SR$_a$, and —S(=O)$_2$R$_a$, and wherein R$_a$ and R$_b$ being each independently hydrogen, $(C_1\text{-}C_{10})$alkyl, halo$(C_1\text{-}C_{10})$alkyl, $(C_3\text{-}C_{10})$cycloalkyl, $(C_6\text{-}C_{12})$aryl, $(C_6\text{-}C_{12})$aryl$(C_1\text{-}C_{10})$alkyl, $(C_1\text{-}C_{20})$heteroaryl, $(C_1\text{-}C_{20})$heteroaryl$(C_1\text{-}C_{10})$alkyl, $(C_1\text{-}C_{20})$heterocycle, $(C_1\text{-}C_{20})$heterocyclyl$(C_1\text{-}C_{10})$alkyl or —(CH$_2$)$_z$C(=O)R$_c$, z is an integer of 1, 2, 3 or 4, and R$_c$ is hydroxyl, $(C_1\text{-}C_{10})$alkyl, $(C_3\text{-}C_{10})$cycloalkyl or $(C_1\text{-}C_{10})$alkoxy.

3. The compound of claim 1, which is selected from the group consisting of formulas (II), (III), (IV), (V) and (VI):

-continued (VI)

wherein,
R₁, R₂, R_{3a}, R_{3b} and R₄ have the same meanings as defined in claim 1;
X is at least one substituent selected from the group consisting of halogen, acetylene, vinyl, hydroxy, cyano, nitro, amino, $(C_1-C_{10})$alkylamino, di$(C_1-C_{10})$alkylamino, $(C_1-C_{10})$alkyl, $(C_3-C_{10})$cycloalkyl, $(C_1-C_{10})$alkoxy, $(C_1-C_{10})$alkylthio, halo$(C_1-C_{10})$alkyl, $(C_6-C_{12})$aryl, $(C_6-C_{12})$aryl$(C_1-C_{10})$alkyl, $(C_1-C_{20})$heteroaryl, $(C_1-C_{20})$heteroaryl$(C_1-C_{10})$alkyl, $(C_1-C_{20})$heterocycle, $(C_1-C_{20})$heterocyclyl$(C_1-C_{10})$alkyl, —NR_aR_b—, —NR_aC(=O)R_b, —NR_aC(=O)NR_aOR_b, —NR_aC(=O)NR_aR_b, —NR_aC(=O)OR_b, —NR_aSO_2R_b, —C(=O)R—, —C(=O)OR_a, —OC(=O)R_a, —C(=O)NR_aR_b, —OC(=O)NR_aR_b, —OR_a, —SR_a, —SOR_a, —S(=O)_2R_a, —OS(=O)_2R_a and —S(=O)_2OR_a;
wherein R_a and R_b, which may be the same or different, are each independently hydrogen, $(C_1-C_{10})$alkyl, halo$(C_1-C_{10})$alkyl, $(C_3-C_{10})$cycloalkyl, $(C_6-C_{12})$aryl, $(C_6-C_{12})$aryl$(C_1-C_{10})$alkyl, $(C_1-C_{20})$heteroaryl, $(C_1-C_{20})$heteroaryl$(C_1-C_{10})$alkyl, $(C_1-C_{20})$heterocycle, $(C_1-C_{20})$heterocyclyl$(C_1-C_{10})$alkyl or —(CH_2)_zC(=O)R_c, z is an integer of 1, 2, 3 or 4, and R_c is hydroxyl, $(C_1-C_{10})$alkyl, $(C_3-C_{10})$cycloalkyl or $(C_1-C_{10})$alkoxy,
or a stereoisomer, or a pharmaceutically acceptable salt thereof.

4. The compound of claim 1, which is selected from the group consisting of:
(R)-3-(2-amino-2-phenylethyl)-1-(2-fluoro-6-(trifluoromethyl)benzyl)-1'-((5-(trifluoromethyl)furan-2-yl)methyl)-1H-spiro[furo[3,4-d]pyrimidine-5,4'-piperidine]-2,4(3H,7H)-dione;
(R)-3-(2-amino-2-phenylethyl)-1-(2-fluoro-6-(trifluoromethyl)benzyl)-1'-(3-fluorobenzyl)-1H-spiro[furo[3,4-d]pyrimidine-5,4'-piperidine]-2,4(3H,7H)-dione;
(R)-4-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-phenylethyl)amino)butanoic acid;
(R)-3-(2-amino-2-phenylethyl)-1-(2-fluoro-6-(trifluoromethyl)benzyl)-1'-methyl-1H-spiro[furo[3,4-d]pyrimidine-5,4'-piperidine]-2,4(3H,7H)-dione;
(R)-3-(2-amino-2-phenylethyl)-1-(2-fluoro-6-(trifluoromethyl)benzyl)-1'-(2-methoxyethyl)-1H-spiro[furo[3,4-d]pyrimidine-5,4'-piperidine]-2,4(3H,7H)-dione;
(R)-3-(2-amino-2-phenylethyl)-1-(2-fluoro-6-(trifluoromethyl)benzyl)-1'-neopentyl-1H-spiro[furo[3,4-d]pyrimidine-5,4'-piperidine]-2,4(3H,7H)-dione;
3-((R)-2-amino-2-phenylethyl)-1-(2-fluoro-6-(trifluoromethyl)benzyl)-1'-(2-(1-methylpyrrolidin-2-yl)ethyl)-1H-spiro[furo[3,4-d]pyrimidine-5,4'-piperidine]-2,4(3H,7H)-dione;
(R)-3-(2-amino-2-phenylethyl)-1-(2-fluoro-6-(trifluoromethyl)benzyl)-1'-(pyridin-2-ylmethyl)-1H-spiro[furo[3,4-d]pyrimidine-5,4'-piperidine]-2,4(3H,7H)-dione;
(R)-3-(2-amino-2-phenylethyl)-1-(2-fluoro-6-(trifluoromethyl)benzyl)-1'-(pyridin-3-ylmethyl)-1H-spiro[furo[3,4-d]pyrimidine-5,4'-piperidine]-2,4(3H,7H)-dione;
(R)-3-(2-amino-2-phenylethyl)-1-(2-fluoro-6-(trifluoromethyl)benzyl)-1'-(pyridin-4-ylmethyl)-1H-spiro[furo[3,4-d]pyrimidine-5,4'-piperidine]-2,4(3H,7H)-dione;
(R)-3-(2-amino-2-phenylethyl)-1-(2-fluoro-6-(trifluoromethyl)benzyl)-1'-((5-fluoropyridin-3-yl)methyl)-1H-spiro[furo[3,4-d]pyrimidine-5,4'-piperidine]-2,4(3H,7H)-dione;
(R)-3-(2-amino-2-phenylethyl)-1'-((2-chloropyridin-3-yl)methyl)-1-(2-fluoro-6-(trifluoromethyl)benzyl)-1H-spiro[furo[3,4-d]pyrimidine-5,4'-piperidine]-2,4(3H,7H)-dione;
(R)-3-(2-amino-2-phenylethyl)-1'-((6-chloropyridin-3-yl)methyl)-1-(2-fluoro-6-(trifluoromethyl)benzyl)-1H-spiro[furo[3,4-d]pyrimidine-5,4'-piperidine]-2,4(3H,7H)-dione;
(R)-3-(2-amino-2-phenylethyl)-1-(2-fluoro-6-(trifluoromethyl)benzyl)-1'-((5-methylpyridin-3-yl)methyl)-1H-spiro[furo[3,4-d]pyrimidine-5,4'-piperidine]-2,4(3H,7H)-dione;
(R)-3-(2-amino-2-phenylethyl)-1-(2-fluoro-6-(trifluoromethyl)benzyl)-1'-((6-(trifluoromethyl)pyridin-2-yl)methyl)-1H-spiro[furo[3,4-d]pyrimidine-5,4'-piperidine]-2,4(3H,7H)-dione;
(R)-3-(2-amino-2-phenylethyl)-1-(2-fluoro-6-(trifluoromethyl)benzyl)-1'-(3-methylbenzyl)-1H-spiro[furo[3,4-d]pyrimidine-5,4'-piperidine]-2,4(3H,7H)-dione;
(R)-3-(2-amino-2-phenylethyl)-1-(2-fluoro-6-(trifluoromethyl)benzyl)-1'-(3-methoxybenzyl)-1H-spiro[furo[3,4-d]pyrimidine-5,4'-piperidine]-2,4(3H,7H)-dione;
(R)-3-((3-(2-amino-2-phenylethyl)-1-(2-fluoro-6-(trifluoromethyl)benzyl)-2,4-dioxo-2,3,4,7-tetrahydro-1H-spiro[furo[3,4-d]pyrimidine-5,4'-piperidin]-1'-yl)methyl)benzonitrile;
(R)-3-(2-amino-2-phenylethyl)-1'-(3-chlorobenzyl)-1-(2-fluoro-6-(trifluoromethyl)benzyl)-1H-spiro[furo[3,4-d]pyrimidine-5,4'-piperidine]-2,4(3H,7H)-dione;
(R)-3-(2-amino-2-phenylethyl)-1-(2-fluoro-6-(trifluoromethyl)benzyl)-1'-(3-(trifluoromethyl)benzyl)-1H-spiro[furo[3,4-d]pyrimidine-5,4'-piperidine]-2,4(3H,7H)-dione;
(R)-3-(2-amino-2-phenylethyl)-1-(2-fluoro-6-(trifluoromethyl)benzyl)-1'-(3-(trifluoromethoxy)benzyl)-1H-spiro[furo[3,4-d]pyrimidine-5,4'-piperidine]-2,4(3H,7H)-dione;
(R)-methyl 3-((3-(2-amino-2-phenylethyl)-1-(2-fluoro-6-(trifluoromethyl)benzyl)-2,4-dioxo-2,3,4,7-tetrahydro-1H-spiro[furo[3,4-d]pyrimidine-5,4'-piperidin]-1'-yl)methyl)benzoate;
(R)-3-((3-(2-amino-2-phenylethyl)-1-(2-fluoro-6-(trifluoromethyl)benzyl)-2,4-dioxo-2,3,4,7-tetrahydro-1H-spiro[furo[3,4-d]pyrimidine-5,4'-piperidin]-1'-yl)methyl)-N-methylbenzamide;

(R)-3-(2-amino-2-phenylethyl)-1-(2-fluoro-6-(trifluoromethyl)benzyl)-1'-(3-(methylthio)benzyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(3-hydroxybenzyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(3-(methylsulfonyl)benzyl)-1H-spiro[furo[3,4-d]pyrimidine-5,4'-piperidine]-2,4(3H,7H)-dione;

(R)-3-(2-amino-2-phenylethyl)-1'-(benzo[b]thiophen-7-ylmethyl)-1-(2-fluoro-6-(trifluoromethyl)benzyl)-1H-spiro[furo[3,4-d]pyrimidine-5,4'-piperidine]-2,4(3H,7H)-dione;

(R)-3-(2-amino-2-phenylethyl)-1'-(benzo[c][1,2,5]oxadiazol-4-ylmethyl)-1-(2-fluoro-6-(trifluoromethyl)benzyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(2-methylbenzyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(2-methoxybenzyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(2-hydroxybenzyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(2-fluorobenzyl)-1H-spiro[furo[3,4-d]pyrimidine-5,4'-piperidine]-2,4(3H,7H)-dione;

(R)-2-((3-(2-amino-2-phenylethyl)-1-(2-fluoro-6-(trifluoromethyl)benzyl)-2,4-dioxo-2,3,4,7-tetrahydro-1H-spiro[furo[3,4-d]pyrimidine-5,4'-piperidin]-1'-yl)methyl)benzonitrile;

(R)-3-(2-amino-2-phenylethyl)-1'-(2,3-difluorobenzyl)-1-(2-fluoro-6-(trifluoromethyl)benzyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(2-(trifluoromethyl)benzyl)-1H-Spiro[furo[3,4-d]pyrimidine-5,4'-piperidine]-2,4(3H,7H)-dione;

(R)-2-((3-(2-amino-2-phenylethyl)-1-(2-fluoro-6-(trifluoromethyl)benzyl)-2,4-dioxo-2,3,4,7-tetrahydro-1H-spiro[furo[3,4-d]pyrimidine-5,4'-piperidin]-1'-yl)methyl)-6-fluorobenzonitrile;

(R)-3-((3-(2-amino-2-phenylethyl)-1-(2-fluoro-6-(trifluoromethyl)benzyl)-2,4-dioxo-2,3,4,7-tetrahydro-1H-spiro[furo[3,4-d]pyrimidine-5,4'-piperidine]-1'-yl)methyl)-2-fluorobenzonitrile;

(R)-3-(2-amino-2-phenylethyl)-1-(2,6-difluorobenzyl)-1'-(3-(trifluoromethyl)benzyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(2-(trifluoromethoxy)benzyl)-1H-Spiro[furo[3,4-d]pyrimidine-5,4'-piperidine]-2,4(3H,7H)-dione;

(R)-methyl 2-((3-(2-amino-2-phenylethyl)-1-(2-fluoro-6-(trifluoromethyl)benzyl)-2,4-dioxo-2,3,4,7-tetrahydro-1H-spiro[furo[3,4-d]pyrimidine-5,4'-piperidin]-1'-yl)methyl)benzoate;

(R)-3-(2-amino-2-phenylethyl)-1'-(2-chlorobenzyl)-1-(2-fluoro-6-(trifluoromethyl)benzyl)-1H-Spiro[furo[3,4-d]pyrimidine-5,4'-piperidine]-2,4(3H,7H)-dione;

(R)-3-(2-amino-2-phenylethyl)-1'-(2-fluoro-3-methoxybenzyl)-1-(2-fluoro-6-(trifluoromethyl)benzyl)-1H-Spiro[furo[3,4-d]pyrimidine-5,4'-piperidine]-2,4(3H,7H)-dione;

(R)-5-((3-(2-amino-2-phenylethyl)-1-(2-fluoro-6-(trifluoromethyl)benzyl)-2,4-dioxo-2,3,4,7-tetrahydro-1H-spiro[furo[3,4-d]pyrimidine-5,4'-piperidine]-1'-yl)methyl)furan-2-carboxamide;

(R)-5-((3-(2-amino-2-phenylethyl)-1-(2-fluoro-6-(trifluoromethyl)benzyl)-2,4-dioxo-2,3,4,7-tetrahydro-1H-spiro[furo[3,4-d]pyrimidine-5,4'-piperidin]-1'-yl)methyl)-N-methylfuran-2-carboxamide;

(R)-3-(2-amino-2-phenylethyl)-1-(2,6-difluorobenzyl)-1'-((5-(trifluoromethyl)furan-2-yl)methyl)-1H-spiro[furo[3,4-d]pyrimidine-5,4'-piperidine]-2,4(3H,7H)-dione;

(R)-3-(2-amino-2-phenylethyl)-1'-(3-chlorobenzyl)-1-(2,6-difluorobenzyl)-1H-spiro[furo[3,4-d]pyrimidine-5,4'-piperidine]-2,4(3H,7H)-dione;

(R)-3-((3-(2-amino-2-phenylethyl)-1-(2,6-difluorobenzyl)-2,4-dioxo-2,3,4,7-tetrahydro-1H-spiro[furo[3,4-d]pyrimidine-5,4'-piperidin]-1'-yl)methyl)benzonitrile;

(R)-3-(2-amino-2-phenylethyl)-1-(2-fluoro-6-(trifluoromethyl)benzyl)-1'-phenethyl-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(furan-2-ylmethyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-((5-methylfuran-2-yl)methyl)-1H-spiro[furo[3,4-d]pyrimidine-5,4'-piperidine]-2,4(3H,7H)-dione;

(R)-3-(2-amino-2-phenylethyl)-1'-((5-chlorofuran-2-yl)methyl)-1-(2-fluoro-6-(trifluoromethyl)benzyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-((6-hydroxypyridine-3-yl)methyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(4-methylbenzyl)-1H-spiro[furo[3,4-d]pyrimidine-5,4'-piperidine]-2,4(3H,7H)-dione;

(R)-3-(2-amino-2-phenylethyl)-1'-(4-chlorobenzyl)-1-(2-fluoro-6-(trifluoromethyl)benzyl)-1H-spiro[furo[3,4-d]pyrimidine-5,4'-piperidine]-2,4(3H,7H)-dione;

(R)-4-((3-(2-amino-2-phenylethyl)-1-(2-fluoro-6-(trifluoromethyl)benzyl)-2,4-dioxo-2,3,4,7-tetrahydro-1H-spiro[furo[3,4-d]pyrimidine-5,4'-piperidin]-1'-yl)methyl)benzonitrile (R)-3-(2-amino-2-phenylethyl)-1-(2-fluoro-6-(trifluoromethyl)benzyl)-1'-(4-(trifluoromethyl)benzyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(4-fluorobenzyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(4-hydroxybenzyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(4-methoxybenzyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(pyrazin-2-ylmethyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-((1-methyl-1H-pyrazol-5-yl)methyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(thiazol-4-ylmethyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(thiazol-5-ylmethyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(thiazol-2-ylmethyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(oxazol-4-ylmethyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(isooxazol-3-ylmethyl)-1H-spiro[furo[3,4-d]pyrimidine-5,4'-piperidine]-2,4(3H,7H)-dione;

(R)-1'-acetyl-3-(2-amino-2-phenylethyl)-1-(2-fluoro-6-(trifluoromethyl)benzyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-isobutyryl-1H-spiro[furo[3,4-d]pyrimidine-5,4'-piperidine]-2,4(3H,7H)-dione;

(R)-ethyl 3-(2-amino-2-phenylethyl)-1-(2-fluoro-6-(trifluoromethyl)benzyl)-2,4-dioxo-2,3,4,7-tetrahydro-1H-spiro[furo[3,4-d]pyrimidine-5,4'-piperidine]-1'-carboxylate;

(R)-3-(2-amino-2-phenylethyl)-1-(2-fluoro-6-(trifluoromethyl)benzyl)-1'-(methylsulfonyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1H-spiro[furo[3,4-d]pyrimidine-5,4'-piperidine]-2,4(3H,7H)-dione;

(R)-3-(2-amino-2-phenylethyl)-1-(2-fluoro-6-(trifluoromethyl)benzyl)-1'-(2-(methylsulfonyl)ethyl)-1H-spiro[furo[3,4-d]pyrimidine-5,4'-piperidine]-2,4(3H,7H)-dione;

(R)-3-((3-(2-amino-2-phenylethyl)-1-(2-fluoro-6-(trifluoromethyl)benzyl)-2,4-dioxo-2,3,4,7-tetrahydro-1H-spiro[furo[3,4-d]pyrimidine-5,4'-piperidin]-1'-yl)methyl)benzamide;

(R)-4-((3-(2-amino-2-phenylethyl)-1-(2-fluoro-6-(trifluoromethyl)benzyl)-2,4-dioxo-2,3,4,7-tetrahydro-1H-spiro[furo[3,4-d]pyrimidine-5,4'-piperidin]-1'-yl)methyl)benzamide;

(R)—N-(2-(3-(2-amino-2-phenylethyl)-1-(2-fluoro-6-(trifluoromethyl)benzyl)-2,4-dioxo-2,3,4,7-tetrahydro-1H-spiro[furo[3,4-d]pyrimidine-5,4'-piperidin]-1'-yl)ethyl)-N-methylmethanesulfonamide;

(R)-3-(2-amino-2-phenylethyl)-1-(2-fluoro-6-(trifluoromethyl)benzyl)-1'-(2-morpholinoethyl)-1H-spiro[furo[3,4-d]pyrimidine-5,4'-piperidine]-2,4(3H,7H)-dione;

(R)-4-((2-(1'-(3-chlorobenzyl)-1-(2-fluoro-6-(trifluoromethyl)benzyl)-2,4-dioxo-1H-spiro[furo[3,4-d]pyrimidine-5,4'-piperidin]-3(2H,4H,7H)-yl)-1-phenylethyl)amino)butanoic acid;

(R)-4-((2-(1-(2-fluoro-6-(trifluoromethyl)benzyl)-2,4-dioxo-1'-(3-(trifluoromethyl)benzyl)-1H-spiro[furo[3,4-d]pyrimidine-5,4'-piperidin]-3(2H,4H,7H)-yl)-1-phenylethyl)amino)butanoic acid;

(R)-4-((2-(1-(2,6-difluorobenzyl)-2,4-dioxo-1'-(3-(trifluoromethyl)benzyl)-1H-spiro[furo[3,4-d]pyrimidine-5,4'-piperidin]-3(2H,4H,7H)-yl)-1-phenylethyl)amino)butanoic acid;

(R)-4-((2-(1-(2-fluoro-6-(trifluoromethyl)benzyl)-1'-((5-methylfuran-2-yl)methyl)-2,4-dioxo-1H-spiro[furo[3,4-d]pyrimidine-5,4'-piperidin]-3(2H,4H,7H)-yl)-1-phenylethyl)amino)butanoic acid;

(R)-4-((2-(1'-((5-chlorofuran-2-yl)methyl)-1-(2-fluoro-6-(trifluoromethyl)benzyl)-2,4-dioxo-1H-spiro[furo[3,4-d]pyrimidine-5,4'-piperidin]-3(2H,4H,7H)-yl)-1-phenylethyl)amino)butanoic acid;

(R)-4-((2-(1'-(3-cyano-2-fluorobenzyl)-1-(2-fluoro-6-(trifluoromethyl)benzyl)-2,4-dioxo-1H-spiro[furo[3,4-d]pyrimidine-5,4'-piperidin]-3(2H,4H,7H)-yl)-1-phenylethyl)amino)butanoic acid;

(R)-4-((2-(1-(2,6-difluorobenzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-phenylethyl)amino)butanoic acid;

(R)-4-((2-(1'-(3-chlorobenzyl)-1-(2,6-difluorobenzyl)-2,4-dioxo-1H-spiro[furo[3,4-d]pyrimidine-5,4'-piperidin]-3(2H,4H,7H)-yl)-1-phenylethyl)amino)butanoic acid;

(R)-4-((2-(1'-(3-cyanobenzyl)-1-(2,6-difluorobenzyl)-2,4-dioxo-1H-spiro[furo[3,4-d]pyrimidine-5,4'-piperidin]-3(2H,4H,7H)-yl)-1-phenylethyl)amino)butanoic acid;

(R)-4-((2-(1'-(3-cyanobenzyl)-1-(2-fluoro-6-(trifluoromethyl)benzyl)-2,4-dioxo-1H-spiro[furo[3,4-d]pyrimidine-5,4'-piperidin]-3(2H,4H,7H)-yl)-1-phenylethyl)amino)butanoic acid;

(R)-4-((2-(1-(2-fluoro-6-(trifluoromethyl)benzyl)-1'-(3-(methylcarbamoyl)benzyl)-2,4-dioxo-1H-spiro[furo[3,4-d]pyrimidine-5,4'-piperidin]-3(2H,4H,7H)-yl)-1-phenylethyl)amino)butanoic acid;

(R)-4-((2-(1-(2-fluoro-6-(trifluoromethyl)benzyl)-1'-(3-(methylthio)benzyl)-2,4-dioxo-1H-spiro[furo[3,4-d]pyrimidine-5,4'-piperidin]-3(2H,4H,7H)-yl)-1-phenylethyl)amino)butanoic acid;

(R)-4-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-phenylethyl)amino)butanamide;

(R)-4-((2-(1-(2-fluoro-6-(trifluoromethyl)benzyl)-2,4-dioxo-1'-((5-(trifluoromethyl)furan-2-yl)methyl)-1,2,6,7-tetrahydrospiro[cyclopenta[d]pyrimidine-5,4'-piperidin]-3(4H)-yl)-1-phenylethyl)amino)butanoic acid;

(R)-3-(2-amino-2-phenylethyl)-1-(2-fluoro-6-(trifluoromethyl)benzyl)-1'-((5-(trifluoromethyl)furan-2-yl)methyl)-6,7-dihydrospiro[cyclopenta[d]pyrimidine-5,4'-piperidine]-2,4(1H,3H)-dione;

(R)-3-(2-amino-2-phenylethyl)-1'-(3-chlorobenzyl)-1-(2-fluoro-6-(trifluoromethyl)benzyl)-6,7-dihydrospiro[cyclopenta[d]pyrimidine-5,4'-piperidine]-2,4(1H,3H)-dione;

(R)-4-((2-(1'-(3-chlorobenzyl)-1-(2-fluoro-6-(trifluoromethyl)benzyl)-2,4-dioxo-1,2,6,7-tetrahydrospiro[cyclopenta[d]pyrimidine-5,4'-piperidin]-3(4H)-yl)-1-phenylethyl)amino)butanoic acid;

(R)-3-(2-amino-2-phenylethyl)-1-(2-fluoro-6-(trifluoromethyl)benzyl)-1'-(3-(methylthio)benzyl)-6,7-dihydrospiro[cyclopenta[d]pyrimidine-5,4'-piperidine]-2,4(1H,3H)-dione;

(R)-3-(2-amino-2-phenylethyl)-1'-benzyl-1-(2-fluoro-6-(trifluoromethyl)benzyl)-6,7-dihydrospiro[cyclopenta[d]pyrimidine-5,4'-piperidine]-2,4(1H,3H)-dione;

(R)-3-(2-amino-2-phenylethyl)-1-(2-fluoro-6-(trifluoromethyl)benzyl)-1'-(3-fluorobenzyl)-6,7-dihydrospiro[cyclopenta[d]pyrimidine-5,4'-piperidine]-2,4(1H,3H)-dione;

(R)-3-(2-amino-2-phenylethyl)-1-(2-fluoro-6-(trifluoromethyl)benzyl)-1'-(3-(trifluoromethyl)benzyl)-6,7-dihydrospiro[cyclopenta[d]pyrimidine-5,4'-piperidine]-2,4(1H,3H)-dione;

(R)-3-(2-amino-2-phenylethyl)-1'-((5-chlorofuran-2-yl)methyl)-1-(2-fluoro-6-(trifluoromethyl)benzyl)-6,7-dihydrospiro[cyclopenta[d]pyrimidine-5,4'-piperidine]-2,4(1H,3H)-dione;

(R)-3-(2-amino-2-phenylethyl)-1-(2-fluoro-6-(trifluoromethyl)benzyl)-1'-((5-(trifluoromethyl)furan-2-yl)methyl)-6,7-dihydrospiro[cyclopenta[d]pyrimidine-5,4'-piperidine]-2,4(1H,3H)-dione;

(R)-4-((2-(1-(2-fluoro-6-(trifluoromethyl)benzyl)-1'-(3-(methylthio)benzyl)-2,4-dioxo-1,2,6,7-tetrahydrospiro[cyclopenta[d]pyrimidine-5,4'-piperidin]-3(4H)-yl)-1-phenylethyl)amino)butanoic acid;

(R)-4-((2-(1'-benzyl-1-(2-fluoro-6-(trifluoromethyl)benzyl)-2,4-dioxo-1,2,6,7-tetrahydrospiro[cyclopenta[d]pyrimidine-5,4'-piperidin]-3(4H)-yl)-1-phenylethyl)amino)butanoic acid;

(R)-4-((2-(1-(2-fluoro-6-(trifluoromethyl)benzyl)-1'-(3-fluorobenzyl)-2,4-dioxo-1,2,6,7-tetrahydrospiro[cyclopenta[d]pyrimidine-5,4'-piperidin]-3(4H)-yl)-1-phenylethyl)amino)butanoic acid;

(R)-4-((2-(1-(2-fluoro-6-(trifluoromethyl)benzyl)-2,4-dioxo-1'-(3-(trifluoromethyl)benzyl)-1,2,6,7-tetrahydrospiro[cyclopenta[d]pyrimidine-5,4'-piperidin]-3(4H)-yl)-1-phenylethyl)amino)butanoic acid;

(R)-4-((2-(1'-((5-chlorofuran-2-yl)methyl)-1-(2-fluoro-6-(trifluoromethyl)benzyl)-2,4-dioxo-1,2,6,7-tetrahydrospiro[cyclopenta[d]pyrimidine-5,4'-piperidin]-3(4H)-yl)-1-phenylethyl)amino)butanoic acid;

(R)-4-((2-(1-(2-fluoro-6-(trifluoromethyl)benzyl)-2,4-dioxo-1'-((5-(trifluoromethyl)furan-2-yl)methyl)-1,2,6,7-tetrahydrospiro[cyclopenta[d]pyrimidine-5,4'-piperidin]-3(4H)-yl)-1-phenylethyl)amino)butanoic acid;

(R)-4-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-phenylethyl)amino)butanoic acid;

(S)-4-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-phenylethyl)amino)butanoic acid;

(S)-4-((2-(1'-(3-chlorobenzyl)-1-(2-fluoro-6-(trifluoromethyl)benzyl)-2,4-dioxo-1H-spiro[furo[3,4-d]pyrimidine-5,4'-piperidin]-3(2H,4H,7H)-yl)-1-phenylethyl)amino)butanoic acid;

(R)-3-(2-((3-(2H-tetrazol-5-yl)propyl)amino)-2-phenylethyl)-1-(2-fluoro-6-(trifluoromethyl)benzyl)-1'-((5-(trifluoromethyl)furan-2-yl)methyl)-1H-spiro[furo[3,4-d]pyrimidine-5,4'-piperidine]-2,4(3H,7H)-dione;

(R)-2-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-phenylethyl)amino)ethyl methoxycarbamate;

(R)—N-(3-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-phenylethyl)amino)propyl)-N-hydroxyformamide;

4-((2-(1-(2-fluoro-6-(trifluoromethyl)benzyl)-2,4-dioxo-1'-((5-(trifluoromethyl) furan-2-yl)methyl)-1H-spiro[furo[3,4-d]pyrimidine-5,4'-piperidin]-3(2H,4H,7H)-yl)-1-(6-methylpyridin-2-yl)ethyl)amino)butanoic acid;

4-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-(5-methylthiophen-2-yl)ethyl)amino)butanoic acid;

4-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-(5-methylfuran-2-yl)ethyl)amino)butanoic acid;

4-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-(3-hydroxyphenyl)ethyl)amino)butanoic acid;

(R)-4-((2-(1'-((5-bromofuran-2-yl)methyl)-1-(2-fluoro-6-(trifluoromethyl)benzyl)-2,4-dioxo-1H-spiro[furo[3,4-d]pyrimidine-5,4'-piperidin]-3(2H,4H,7H)-yl)-1-phenylethyl)amino)butanoic acid;

4-((2-(1'-((5-ethenylfuran-2-yl)methyl)-1-(2-fluoro-6-(trifluoromethyl)benzyl)-2,4-dioxo-1H-spiro[furo[3,4-d]pyrimidine-5,4'-piperidin]-3(2H,4H,7H)-yl)-1-(5-methylfuran-2-yl)ethyl)amino)butanoic acid;

4-((2-(1'-(benzofuran-2-ylmethyl)-1-(2-fluoro-6-(trifluoromethyl)benzyl)-2,4-dioxo-1H-spiro[furo[3,4-d]pyrimidine-5,4'-piperidin]-3(2H,4H,7H)-yl)-1-(5-methylfuran-2-yl)ethyl)amino)butanoic acid;

(R)-4-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-phenylethyl)amino)-N-hydroxybutanamide;

(R)-2-(4-(1-amino-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)phenoxy)acetic acid;

4-(3-(1-amino-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)phenoxy)butanoic acid;

2-(3-(1-amino-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)phenoxy)acetic acid;

(R)-4-(4-(1-amino-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)phenoxy)butanoic acid;

3-((3-(1-amino-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)phenyl)amino)propionic acid;

2-((3-(1-amino-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)phenyl)amino)acetic acid;

3-((3-(1-amino-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)phenyl)amino)propionic acid;

3-(2-amino-2-(3-aminophenyl)ethyl)-1-(2-fluoro-6-(trifluoromethyl)benzyl)-1'-((5-(trifluoromethyl)furan-2-yl)methyl)-1H-spiro[furo[3,4-d]pyrimidine-5,4'-piperidine]-2,4(3H,7H)-dione;

3-(2-amino-2-(3-nitrophenyl)ethyl)-1-(2-fluoro-6-(trifluoromethyl)benzyl)-1'-((5-(trifluoromethyl)furan-2-yl)methyl)-1H-spiro[furo[3,4-d]pyrimidine-5,4'-piperidine]-2,4(3H,7H)-dione;

3-(2-amino-2-(4-nitrophenyl)ethyl)-1-(2-fluoro-6-(trifluoromethyl)benzyl)-1'-((5-(trifluoromethyl)furan-2-yl)methyl)-1H-spiro[furo[3,4-d]pyrimidine-5,4'-piperidine]-2,4(3H,7H)-dione;

3-(2-amino-2-(4-aminophenyl)ethyl)-1-(2-fluoro-6-(trifluoromethyl)benzyl)-1'-((5-(trifluoromethyl)furan-2-yl)methyl)-1H-spiro[furo[3,4-d]pyrimidine-5,4'-piperidine]-2,4(3H,7H)-dione;

3-(2-amino-2-(2-aminophenyl)ethyl)-1-(2-fluoro-6-(trifluoromethyl)benzyl)-1'-((5-(trifluoromethyl)furan-2-yl)methyl)-1H-spiro[furo[3,4-d]pyrimidine-5,4'-piperidine]-2,4(3H,7H)-dione;

3-(2-amino-2-(2-nitrophenyl)ethyl)-1-(2-fluoro-6-(trifluoromethyl)benzyl)-1'-((5-(trifluoromethyl)furan-2-yl)methyl)-1H-spiro[furo[3,4-d]pyrimidine-5,4'-piperidine]-2,4(3H,7H)-dione;

tert-butyl(2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)-1-(3-(3-methoxyureido)phenyl)ethyl)carbamate;

1-(3-(1-amino-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)phenyl)-3-methylurea; and N-(3-(1-amino-2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3(2H,4H,7H)-yl)ethyl)phenyl)aceteamide.

5. A pharmaceutical composition comprising the compound of claim 1, or a stereoisomer, or a pharmaceutically acceptable salt thereof.

6. A method of treating a sex hormone-related disease or condition comprising the step of administering to a subject in need thereof an effective amount of the compound, or a stereoisomer, or a pharmaceutically acceptable salt of claim 1, wherein the sex hormone-related disease or condition is selected from the group consisting of endometriosis, uterine fibroids, precocious puberty, amennorrhea, contraception and infertility in females, uterine myoma, irregular menstruation, gonadotropin-producing pituitary adenoma, premenstrual syndrome, and prostate cancer.

7. A method of treating a sex hormone-related disease or condition comprising the step of administering to a subject in need thereof an effective amount of the compound, or a stereoisomer, or a pharmaceutically acceptable salt of claim 2, wherein the sex hormone-related disease or condition is selected from the group consisting of endometriosis, uterine fibroids, precocious puberty, amennorrhea, contraception and infertility in females, uterine myoma, irregular menstruation, gonadotropin-producing pituitary adenoma, premenstrual syndrome, and prostate cancer.

8. A method of treating a sex hormone-related disease or condition comprising the step of administering to a subject in need thereof an effective amount of the compound, or a stereoisomer, or a pharmaceutically acceptable salt of claim 3, wherein the sex hormone-related disease or condition is selected from the group consisting of endometriosis, uterine fibroids, precocious puberty, amennorrhea, contraception and infertility in females, uterine myoma, irregular menstruation, gonadotropin-producing pituitary adenoma, premenstrual syndrome, and prostate cancer.

9. A method of treating a sex hormone-related disease or condition comprising the step of administering to a subject in need thereof an effective amount of the compound, or a stereoisomer, or a pharmaceutically acceptable salt of claim 4, wherein the sex hormone-related disease or condition is selected from the group consisting of endometriosis, uterine fibroids, precocious puberty, amennorrhea, contraception and infertility in females, uterine myoma, irregular menstruation, gonadotropin-producing pituitary adenoma, premenstrual syndrome, and prostate cancer.

* * * * *